(12) United States Patent
Klar et al.

(10) Patent No.: US 9,102,701 B2
(45) Date of Patent: Aug. 11, 2015

(54) 17-HYDROXY-17-PENTAFLUOROETHYL-ESTRA-4,9(10)-DIENE-11-ETHYNYLPHENYL DERIVATIVES, METHODS FOR THE PRODUCTION THEREOF AND USE THEREOF FOR TREATING DISEASES

(75) Inventors: Ulrich Klar, Berlin (DE); Wolfgang Schwede, Glienicke (DE); Carsten Möller, Berlin (DE); Andrea Rotgeri, Berlin (DE); Wilhelm Bone, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 473 days.

(21) Appl. No.: 13/386,420

(22) PCT Filed: Jul. 8, 2010

(86) PCT No.: PCT/EP2010/004156
§ 371 (c)(1),
(2), (4) Date: Apr. 5, 2012

(87) PCT Pub. No.: WO2011/009533
PCT Pub. Date: Jan. 27, 2011

(65) Prior Publication Data
US 2012/0190660 A1    Jul. 26, 2012

(30) Foreign Application Priority Data
Jul. 21, 2009 (DE) .......................... 10 2009 034 526

(51) Int. Cl.
*A61K 31/58* (2006.01)
*A61K 31/567* (2006.01)
*C07J 1/00* (2006.01)
*C07J 21/00* (2006.01)
*C07J 41/00* (2006.01)
*C07J 43/00* (2006.01)

(52) U.S. Cl.
CPC .............. *C07J 1/0081* (2013.01); *C07J 1/0037* (2013.01); *C07J 21/006* (2013.01); *C07J 41/0083* (2013.01); *C07J 41/0094* (2013.01); *C07J 43/003* (2013.01)

(58) Field of Classification Search
CPC .. C07J 1/0037; C07J 41/0083; C07J 41/0094; C07J 43/003; A61K 31/567; A61K 31/58
USPC ................... 552/648; 514/176, 179
See application file for complete search history.

(56) References Cited
U.S. PATENT DOCUMENTS

| | | | |
|---|---|---|---|
| 4,386,085 A | 5/1983 | Teutsch et al. |
| 4,609,651 A | 9/1986 | Rohde et al. |
| 4,634,695 A | 1/1987 | Torelli et al. |
| 4,900,725 A | 2/1990 | Nioue et al. |
| 4,921,846 A | 5/1990 | Nedelec et al. |
| 4,954,490 A | 9/1990 | Cook et al. |
| 5,073,548 A | 12/1991 | Cook et al. |
| 5,108,996 A | 4/1992 | Claussner et al. |
| 5,272,140 A | 12/1993 | Loozen |
| 5,407,928 A | 4/1995 | Kasch et al. |
| 5,576,310 A | 11/1996 | Schubert et al. |
| 5,693,628 A | 12/1997 | Schubert et al. |
| 5,712,264 A | 1/1998 | Hamersma et al. |
| 5,739,125 A | 4/1998 | Kasch et al. |
| 5,986,115 A | 11/1999 | Bohlmann et al. |
| 6,020,328 A | 2/2000 | Cook et al. |
| 6,042,324 A | 3/2000 | Aggarwal et al. |
| 6,225,298 B1 | 5/2001 | Spicer et al. |

(Continued)

FOREIGN PATENT DOCUMENTS

| | | |
|---|---|---|
| CA | 2280041 C | 8/1998 |
| DE | 19706061 A1 | 8/1998 |

(Continued)

OTHER PUBLICATIONS

Ulrike Fuhrmann, Holger Hess-Stumpp, Arwed Cleve, Günter Neef, Wolfgang Schwede, Jens Hoffmann, Karl-Heinrich Fritzemeir, Kristof Chwalisz, "Synthesis and Biological Activity of a Novel, highly Potent Progesterone Receptor Antiagonist," J. Med. Chem., vol. 43, pp. 5010-5016 (2000).

(Continued)

*Primary Examiner* — Barbara P Badio
(74) *Attorney, Agent, or Firm* — Karen B. King; Thomas C. Blankinship

(57) ABSTRACT

The invention relates to 17-hydroxy-17-pentafluoroethyl-estra-4,9(10)-diene 11-ethynylphenyl derivatives of the formula I, in which $R^1$ and X are each as defined in the claims and the description,

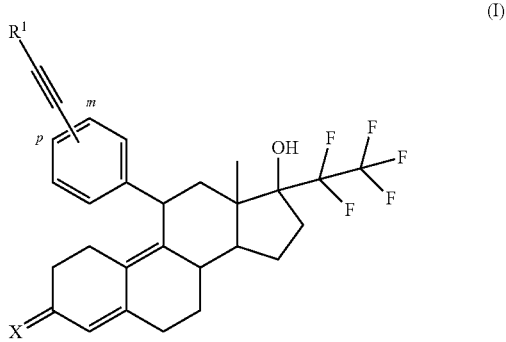

and to a process for preparation thereof and to the use thereof as medicaments.

10 Claims, No Drawings

(56) References Cited

U.S. PATENT DOCUMENTS

| | | | |
|---|---|---|---|
| 6,316,432 B1 | 11/2001 | Schwede et al. |
| 6,476,079 B1 | 11/2002 | Jukarainen et al. |
| 6,503,895 B2 | 1/2003 | Schwede et al. |
| 6,806,263 B2 | 10/2004 | Schwede et al. |
| 6,825,182 B2 | 11/2004 | Ring et al. |
| 6,861,415 B2 | 3/2005 | Kim et al. |
| 7,087,591 B2 | 8/2006 | Kim et al. |
| 7,148,213 B2 | 12/2006 | Schwede et al. |
| 7,192,942 B2 | 3/2007 | Grawe et al. |
| 7,550,451 B2 | 6/2009 | Hillisch et al. |
| 7,799,770 B2 | 9/2010 | Grawe et al. |
| 7,910,573 B2 | 3/2011 | Beckmann et al. |
| 8,053,426 B2 | 11/2011 | Fuhrmann et al. |
| 2001/0016578 A1 | 8/2001 | Spicer et al. |
| 2002/0045774 A1 | 4/2002 | Schwede et al. |
| 2002/0143000 A1 | 10/2002 | Hegele-Hartung |
| 2003/0069434 A1 | 4/2003 | Bohlmann et al. |
| 2003/0191099 A1 | 10/2003 | Bohlmann et al. |
| 2004/0006241 A1 | 1/2004 | Grawe |
| 2004/0048841 A1 | 3/2004 | Hoffmann |
| 2004/0157811 A1 | 8/2004 | Lichtner |
| 2005/0080060 A1 | 4/2005 | Schwede |
| 2005/0277769 A1 | 12/2005 | Burton et al. |
| 2007/0105828 A1 | 5/2007 | Joshi et al. |
| 2009/0075989 A1 | 3/2009 | Schwede et al. |
| 2011/0112057 A1 | 5/2011 | Fuhrmann et al. |
| 2012/0149670 A1 | 6/2012 | Schwede et al. |
| 2012/0184515 A1 | 7/2012 | Klar et al. |
| 2012/0232042 A1 | 9/2012 | Klar et al. |
| 2012/0258941 A1 | 10/2012 | Klar et al. |
| 2012/0316145 A1 | 12/2012 | Klar et al. |
| 2013/0005697 A1 | 1/2013 | Schwede et al. |
| 2013/0072464 A1 | 3/2013 | Schwede et al. |

FOREIGN PATENT DOCUMENTS

| | | |
|---|---|---|
| DE | 10221034 A1 | 11/2003 |
| EP | 0057115 A2 | 4/1982 |
| EP | 0411733 B1 | 2/1991 |
| EP | 0676203 A1 | 10/1995 |
| EP | 909764 A1 | 4/1999 |
| EP | 0970103 B1 | 1/2000 |
| EP | 1862468 | 12/2007 |
| IN | 978/MUM/2005 | 8/2005 |
| JP | H11171774 A | 6/1999 |
| WO | 9603130 A1 | 2/1996 |
| WO | 9615794 | 5/1996 |
| WO | 9623503 A1 | 8/1996 |
| WO | 98/05679 A2 | 2/1998 |
| WO | 9807740 | 2/1998 |
| WO | 98/26783 A1 | 6/1998 |
| WO | 98/34947 A1 | 8/1998 |
| WO | 9933855 | 7/1999 |
| WO | 99/53924 A1 | 10/1999 |
| WO | 01/47490 A1 | 7/2001 |
| WO | 02/32429 A2 | 4/2002 |
| WO | 03045972 A1 | 6/2003 |
| WO | 2004014935 A1 | 2/2004 |
| WO | 2006/010097 A2 | 1/2006 |
| WO | 2008/058767 A1 | 5/2008 |
| WO | 2009138186 A2 | 11/2009 |
| ZA | 977482 | 2/1998 |

OTHER PUBLICATIONS

Jody Steinauer, Elizabeth A. Fritts, Rebecca Jackson, Alison F. Jacoby, "Systematic review of mifepristone for the treatment of uterine leiomyomata," Obstet Gynecol, vol. 103, No. 6, pp. 1331-1336 (Jun. 2004).
Kristof Chwalisz, Lois Larsen, Cynthia Mattia-Goldberg, Anthony Edmonds, Walter Elger, and Craig A. Winkel, "A randomized, controlled trial of asoprisnil, a novel selective progesterone receptor modulator, in women with uterine leiomyomata," Fertil Steril, vol. 87, No. 6, pp. 1399-1412 (Jun. 2007).
L. Michael Kettel, Ana A. Murphy, Joseph F. Mortola, James H. Liu, André Ulmann, and Samuel S.C. Yen, "Endocrine responses to long-term administration of the antiprogesterone RU486 in patients with pelvic endometriosis," Fertil Steril, vol. 56, No. 3, pp. 402-407 (Sep. 1991).
L. Michael Kettel, Ana A. Murphy, Arlene J. Morales, André Ulmann, Etienne E. Baulieu, and Samuel S.C. Yen, "Treatment of endometriosis with the antiprogesterone mifepristone (RU486)," Fertil Steril, vol. 65, No. 1, pp. 23-28 (Jan. 1996).
L. Michael Kettel, Ana A. Murphy, Arlene J. Morales, and Samuel S.C. Yen, "Preliminary report on the treatment of endometriosis with low-dose mifepristone (RU 486),". Am J Obstet Gynecol, vol. 178, No. 6, pp. 1151-1156 (Jun. 1998).
Carsten Möller, Jens Hoffmann, Thomas A Kirkland and Wolfgang Schwede, "Investigational developments for the treatment of progesterone-dependent diseases," Expert Opin. Investig. Drugs., vol. 17, No. 4, pp. 469-479 (2008).
Madhu Bagaria, Amita Suneja, Neelam B. Vaid, Kiran Guleria, and Kiran Mishra, Low-dose mifepristone in treatment of uterine leiomyoma: A randomised double-blind placebo-controlled clinical trial, The Royal Australian and New Zealand College of Obstetricians and Gynaecologists, vol. 49, pp. 77-83 (2009).
Ana A. Murphy, L. Michael Kettel, Arlene J. Morales, Veronica J. Roberts and Samuel S.C. Yen, "Regression of Uterine Leiomyomata in Response to the Antiprogesterone RU 486," J. Clin. Endocrinol. Metab., vol. 76, No. 2, pp. 513-517 (1993).
M. Bohl, G. Schubert, K. Ponsold, G. Reck, E. Höhne, and K. Simon, "Molecular mechanics and X-ray crystal structure investigations on conformations of 11β substituted 4,9-dien-3-one steroids," J. Mol. Graphics, vol. 7, pp. 122-153 (Sep. 1989).
Dario Braga and Joel Bernstein, "3.3 Crystal Polymorphism: Challenges at the Crossroads of Science and Technology," Making Crystals by Design (Dario Braga and Fabrizia Grepioni eds., Wiley-VCH Verlag GmbH & Co. KgaA, Weinheim, Germany), pp. 293-314 (2007).
Walter Cabri, Paolo Ghetti, Giovanni Pozzi, and Marco Alpegiani, "Polymorphisms and Patent, Market, and Legal Battles: Cefdinir Case Study," Organic Process Research & Devel., vol. 11, No. 1, pp. 64-72 (2007).
Mino R. Caira, "Crystalline Polymorphism of Organic Compounds," Topics in Current Chemistry, vol. 198, pp. 164-208 (1998).
R.J. Davey, "Solvent Effects in Crystallization Processes," Current Topics in Material Science, vol. 8, pp. 429-479 (1982).
English Translation of Office Action for European Application No. 06090095.8 dated Jan. 16, 2007.
Braja G. Hazra and Vandana S. Pore, "Mifepristone (RU-486), the recently developed antiprogesterone drug and tis analogues," J. Indian Inst. Sci., vol. 81, pp. 287-298 (May-Jun. 2001).
English Language Abstract of Japanese Patent Publication JP11171774 (corresponding to Japanese Patent Application No. 19970335723 filed Dec. 5, 1997) by Kyowa Hakko Kogyo Co. Ltd., published Jun. 29, 1999.
R. Maibauer, C. Zurth, M. Schultze-Mosgau, B. Rohde, I. Kuss, and W. Sittner, "First human data for ZK 230211 (ZK-PRA), a new progesterone receptor antagonist: a phase I clinical analysis of safety and pharmacokinetics in healthy postmenopausal women," Abstracts-Poster Session IV, 29th Annual San Antonio Breast Cancer Symposium, Dec. 14-17, 2006.
David K. Tellekson, Elizabeth A. Richardson, and Sandra S. Lee, "Strategies for Attacking and Defending Pharmaceutical Patents: A Modern Take on 'The Art of War,'" Int. Property & Techn. Law Journal, vol. 17, No. 12, pp. 5-14 (Dec. 2005).
English Language Translation of EP0411733.
English Language Translation of EP0676203.
English Language Translation of WO1998/026783.
English Language Translation of WO1999/053924.
V.J. Van Geerstein, J.A. Kanters, P. Van Der Sluis, and J. Kroon, "Structure of the n-Butyl Acetate Solvate of 11β-[4-(Dimethylamino)phenyl]-17β-hydroxy-17α-(1-propynyl)estra-4,9-dien-3-one," Acta Cryst., C42, pp. 1521-1523 (1986).
Sudha R. Vippagunta, Harry G. Brittain, David J.W. Grant, "Crystalline Solids," Adv. Drug Delivery Reviews, vol. 48, pp. 3-26 (2001).

(56) References Cited

OTHER PUBLICATIONS

George A. Patani and Edmond J. Lavoie, "Bioisosterism: A Rational Approach in Drug Design," Chem. Rev., vol. 96, pp. 3147-3176 (1996).
Braja, et al., "Mifepristone [RU-486), the recently developed antiprogesterone drug and its analogues," J. Indian Inst. Sci., 2001, 81:287-289.
U.S. Appl. No. 13/384,332, 371(c) date Jun. 4, 2012, published as US 2012-0232042.
U.S. Appl. No. 13/384,765, 371(c) dated Apr. 5, 2012, published as US 2012-0184515.
U.S. Appl. No. 13/386,031, 371(c) date Aug. 28, 2012, punlished as US 2012-0316145.
U.S. Appl. No. 13/386,421, 371(c) date Jun. 25, 2012, published as US 2012-0258941.
U.S. Appl. No. 13/376,512, 371 (c) date Feb. 27, 2012, published as US 2012-0149670.
U.S. Appl. No. 13/577,799, 371(c) date Sep. 21, 2012, published as US 2013-0005697.
U.S. Appl. No. 13/578,500 371(c) date Oct. 1, 2012, published as US 2013-0071464.

17-HYDROXY-17-PENTAFLUOROETHYL-ESTRA-4,9(10)-DIENE-11-ETHYNYLPHENYL DERIVATIVES, METHODS FOR THE PRODUCTION THEREOF AND USE THEREOF FOR TREATING DISEASES

The invention relates to the subject-matter described in the claims, i.e. novel 17-hydroxy-13-methyl-17-pentafluoroethyl-11-ethynylphenyldodecahydrocyclopenta[a]phenanthren-3-one derivatives with progesterone-antagonizing action, to a process for preparation thereof, to the use thereof for treatment and/or prophylaxis of disorders and to the use thereof for production of medicaments for treatment and/or prophylaxis of disorders.

Compounds with antagonistic action on the progesterone receptor (competitive progesterone receptor antagonists) became known for the first time in 1982 (RU 486; EP 057115) and have been studied intensively and described ever since.

Progesterone receptor antagonists with a fluorinated 17 side chain were described by U. Fuhrmann et al., J. Med. Chem. 43, 5010-5016 (2000) and are claimed in WO 98/134947. The compounds with a fluorinated 17 side chain described therein generally have very strong antagonistic activity on the progesterone receptor. Very potent compounds which are therefore preferred in WO 98/34947 are 11β-(4-acetylphenyl)-20,20,21,21,21-pentafluoro-17-hydroxy-19-nor-17α-pregna-4,9-dien-3-ono, 11β-(4-acetylphenyl)-20,20,21,21,21-pentafluoro-17-hydroxy-19-nor-17α-pregna-4-en-3-one and 6'-acetyl-9,11β-dihydro-17β-hydroxy-17α-(1,1,2,2,2-pentafluoroethyl)-4'H-naphth[3',2',1':10,9,11]ester-4-en-3-one. These compounds are converted to various metabolites to a considerable degree in vivo, some of which have strong pharmacological activity, some of them lesser pharmacological activity. The metabolism occurs predominantly at the 4 substituent of the 11β-phenyl radical.

WO 2008/058767 describes compounds of which at least some are metabolites of the compounds described in WO 98/34947.

It is an object of the present invention to provide highly potent competitive progesterone receptor antagonists and hence alternative possible treatments of gynaecological disorders.

It has been found that the inventive compounds are particularly suitable for achieving this object.

The present invention relates to 17-hydroxy-17-pentafluoroethylestra-4,9(10)-diene 11-ethynylphenyl derivatives with the general chemical formula I:

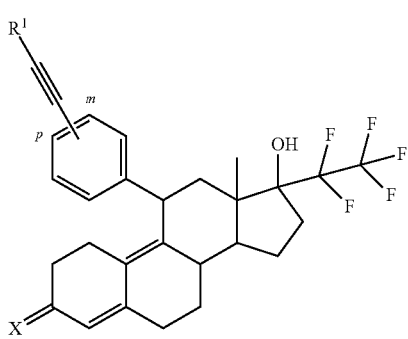

(I)

in which
$R^1$ is joined to the phenyl ring in the m or p position via a C—C triple bond and is a $-(CH=CH)_n-R^2$, $-(CH_2)_q-R^3$ or $-CH=NOR^4$ radical, $R^2$ is hydrogen or an aryl, $C_1$-$C_{10}$-alkyl, $-CO_2R^6$ or $-CN$ group, $R^3$ is hydrogen, $NH_2$, $N_3$ or an $-NHCONHR^4$, $-OCONHR^4$, $-OR^5$ group, $R^4$ is selected from the group comprising hydrogen, $C_1$-$C_{10}$-alkyl, $C_{2-10}$-alkenyl, aryl, $C_7$-$C_{20}$-aralkyl, $(CH_2)_s$—$R^6$, $CH_2$—$CO$—$OR^6$,

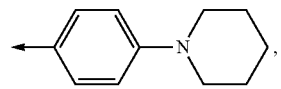

in which
$R^5$ is selected from the group comprising hydrogen, $C_7$-$C_{20}$-aralkyl, $CH_2CO_2R^6$, $CH_2CN$, $CH_2CH_2OH$,

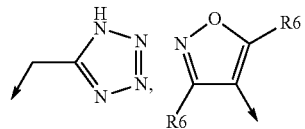

n is 0 to 2,
q is 1 or 2,
s is 1 or 2,
$R^6$ is hydrogen, $C_1$-$C_{10}$-alkyl, aryl, $C_7$-$C_{20}$-aralkyl,
X is oxygen, $NOR^6$ or an $NNHSO_2R^6$ group where $R^6$ is as defined above,
The arrow, for example in the

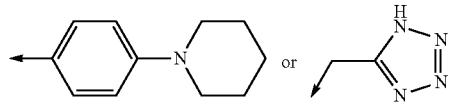

group, indicates the position at which the particular radical is bonded to the adjacent group.

In the context of the present invention, the substituents, unless specified otherwise, are each defined as follows:

Alkyl in $R^2$, $R^4$ and $R^6$ and in other cases is understood to mean straight- or branched-chain alkyl groups with the specified number of carbon atoms or, as the case may be, 1-10 carbon atoms, for example methyl, ethyl, propyl, isopropyl, butyl, isobutyl, tert-butyl, pentyl, isopentyl, neopentyl, hexyl, heptyl, octyl, nonyl or decyl. The alkyl groups $R^2$, $R^4$ and $R^6$ may also be perhalogenated, preferably perfluorinated, or substituted by 1-5 halogen atoms, hydroxyl groups, $C_1$-$C_4$-alkoxy groups, $C_6$-$C_{12}$-aryl groups (which may in turn be substituted by 1-3 halogen atoms). More particularly, alkyl may therefore also be hydroxymethylene (HO—$CH_2$), hydroxyethylene (HO—$C_2H_4$), hydroxypropylene (HO—$C_3H_6$) and hydroxybutylene (HO—$C_4H_8$) and the isomers thereof.

Alkenyl in $R^4$ is understood to mean straight- or branched-chain alkenyl groups having 2-10 carbon atoms, for example vinyl, propenyl, butenyl, pentenyl, isobutenyl or isopentenyl.

The alkenyl group $R^4$ may be substituted by 1-5 halogen atoms, hydroxyl groups, $C_1$-$C_3$-alkoxy groups or $C_6$-$C_{12}$-aryl groups (which may in turn be substituted by 1-3 halogen atoms).

Aryl in $R^2$, $R^4$ and $R^6$ and in other cases is understood to mean aromatic mono- or bicyclic radicals having generally 5 to 10 and up to 5 heteroatoms from the group of S, O and N, for example phenyl, naphthyl, furyl, thienyl, pyridyl, pyrazolyl, pyrimidinyl, oxazolyl, isoxazolyl, pyridazinyl, pyrazinyl, quinolyl, thiazolyl or tetrazolyl, which may be mono- or polysubstituted by halogen, OH, $SO_2$-alkyl, SO-alkyl and S-alkyl, O-alkyl, $CO_2H$, $CO_2$-alkyl, $NH_2$, $NO_2$, $N_3$, CN, $C_1$-$C_{10}$-alkyl, $C_1$-$C_{10}$-acyl or $C_1$-$C_{10}$-acyloxy groups. If aryl is otherwise mentioned as a substituent on alkyl, alkenyl or alkynyl, it is especially aryl groups having 5-12 ring atoms.

Aralkyl in $R^4$, $R^5$ and $R^6$ is understood to mean aralkyl groups. Aralkyl represents aralkyl groups which may contain up to 14 carbon atoms, preferably 6-10 carbon atoms, in the ring and 1-8, preferably 1-4, carbon atoms in the alkyl chain. Useful aralkyl radicals include, for example, benzyl, phenylethyl, naphthylmethyl, naphthylethyl, furylmethyl, thienylethyl, pyridylpropyl. The rings may be mono- or polysubstituted by halogen, OH, O-alkyl, $CO_2H$, $CO_2$-alkyl, $NH_2$, $NH(C_1$-$C_{10}$-alkyl), $N(C_1$-$C_{10}$-alkyl$)_2$, $NO_2$, $N_3$, CN, $C_1$-$C_{20}$-alkyl, $C_1$-$C_{10}$-perfluoroalkyl, $C_1$-$C_{20}$-acyl or $C_1$-$C_{20}$-acyloxy groups.

Possible heteroatoms include sulphur, oxygen or nitrogen, preference being given to nitrogen. One example is the pyridylpropyl radical.

Any mention of alkoxy(O-alkyl) refers to alkoxy groups having 1-4 carbon atoms. Alkoxy may especially be methoxy, ethoxy and propoxy.

Any mention of acyl(CO-alkyl) refers to acyl groups having 1-20 carbon atoms. Acyl may especially be formyl, acetyl, propionyl and butyryl.

Any mention of acyloxy(O—CO-alkyl) refers to acyloxy groups having 1-20 carbon atoms. Acyloxy may especially be formyloxy, acetyloxy, propionyloxy and butyryloxy.

Halogen is fluorine, chlorine or bromine. Among these, preference is given to fluorine or chlorine.

Preference is given in accordance with the invention to derivatives in which the X group is an oxygen atom.

Preference is also given to compounds in which the

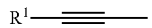

group is joined to the phenyl ring in the para position.

Depending on their structure, the inventive compounds of the general formula I can exist in stereoisomeric forms (enantiomers, diastereomers). The invention therefore encompasses the enantiomers or diastereomers and the particular mixtures thereof, including the racemates. The stereoisomerically homogeneous constituents can be isolated from such mixtures of enantiomers and/or diastereomers in a known manner.

Each of the said substituents on the steroid backbone may be either in an α position or in a β position. In addition, it is also possible for the substituents on the steroid backbone which contain a double bond and in which the double bond bears at least one non-hydrogen substituent on each atom to be present either in E or Z configuration.

When the inventive compounds can occur in tautomeric forms, the present invention encompasses all tautomeric forms.

Moreover, the present invention also encompasses prodrugs of the inventive compounds. The term "prodrugs" encompasses compounds which, during their time of residence in the body, are converted to inventive compounds, for example by enzymatic or hydrolytic processes.

The inventive compounds of the general formula I may also be present in the form of solvates, hydrates and salts, also including different crystal polymorphs, and α-, β- or γ-cyclodextrin clathrates, or compounds of the formula I encapsulated with liposomes.

Solvates in the context of the invention refer to those forms of the inventive compounds which, in the solid or liquid state, exhibit adduct formation with solvent molecules. If the derivatives of the formula I are in solvate form, the solvent present may be present in a stoichiometric or else non-stoichiometric ratio. In the case of stoichiometric solvates, these are also referred to as hemi-, (semi-), mono-, sesqui-, di-, tri-, tetra-, penta-, etc. solvates.

Hydrates are a specific form of the solvates in which the coordination is with water.

Among the solvates, preference is given in accordance with the invention to those with water. These are also referred to as hydrates.

Preferred salts in the context of the invention are physiologically compatible salts of the inventive compounds. Also included, however, are salts which are themselves unsuitable for pharmaceutical applications but can be used, for example, for the isolation or purification of the inventive compounds.

Physiologically compatible salts of the inventive compounds include—when a basic function is present—salts with inorganic or organic acids, especially of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid or benzoic acid. Physiologically compatible salts of the inventive compounds include—when an acid function is present—alkali metal salts, alkaline earth metal salts or ammonium salts, as obtainable by reaction with corresponding inorganic or organic bases. Preferred examples include alkali metal salts (e.g. sodium and potassium salts), alkaline earth metal salts (e.g. calcium and magnesium salts) and ammonium salts derived from ammonia or organic amines having 1 to 16 carbon atoms, preferred examples being ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methyl-glucamine, D-methylglucamine, ethylglucamine, 1,6-hexadiamine, glucosamine, N-methylglycine, 2-amino-1,3-propanediol, tris (hydroxymethyl)aminomethane or 1-amino-2,3,4-butanetriol.

It has been found that the inventive compounds of the formula (I), surprisingly, have good progesterone-antagonizing action, without having the disadvantages of the prior art compounds.

For instance, most of the inventive compounds have a surprisingly high metabolic stability in vitro in liver microsomes of rats and humans. In some of the compounds tested in vivo in rats, low clearance and a surprisingly long half-life in vivo in rats were found. At the same time, it has been possible to distinctly improve the water solubility for some compounds (see Example 61).

These compounds are valuable active pharmaceutical ingredients. They can be used, inter alia, for production of pharmaceutical formulations for treatment of fibroids of the uterus or of endometriosis, heavy menstrual bleeds, meningiomas, hormone-dependent breast cancers and complaints associated with the menopause, or for fertility control and emergency contraception.

For treatment of fibroids of the uterus or of endometriosis, the inventive compounds can be combined simultaneously or sequentially with gestagens or combinations of oestrogens and gestagens.

WO 96/15794 (Spicer et al., Balance Pharm. Inc.), WO 96/03130 (Stöckemann et al., Schering AG) and PCT/EP2009/003249 (Möller et al., Bayer Schering Pharma AG) disclose progesterone receptor antagonist/gestagen regimens. Fibroids of the uterus and endometriosis are very suitably treated by optionally repeating regimens in which the progesterone receptor antagonist is administered over a period of two to four months, followed by the administration of the gestagen over a period of one to four weeks. A particularly suitable administration is the optionally repeating 84-day administration of the progesterone receptor antagonist, followed by the 14-day administration of the gestagen.

For treatment of tumour disorders, it is possible, for example, to either simultaneously or sequentially administer the following active ingredients/active ingredient classes: SERMs, SERDs, antioestrogens, aromatase inhibitors, kinase inhibitors, angiogenesis inhibitors and/or cytostatics.

For treatment of complaints associated with the menopause, one option is a simultaneous or sequential administration of the inventive compounds, for example, with SERMs, SERDs and oestrogens.

SERMs (Selective Estrogen Receptor Modulators) are, in accordance with the invention, those compounds which are tissue-selective and have either antioestrogenic or oestrogenic action, for example inhibit the action of oestrogen in the uterus, but have a neutral or oestrogen-like action in the bone. Examples are clomifene, raloxifene, tamoxifene, torimifene, bazedoxifene, lasofoxifene and ormeloxifene.

Selective oestrogen receptor destabilizers (SERD) are medicaments which fully antagonize the oestrogen receptor and lead to degradation of the receptor.

Antioestrogens are compounds which fully antagonize the oestrogen receptor, for example fulvestrant.

Aromatase inhibitors inhibit the enzyme aromatase and hence the aromatization of androgens in oestrogens. These include anastrozole, letrozole, exemestane, vorozole, formestane and fadrozole.

Kinase inhibitors inhibit enzymes which transfer a phosphate residue from ATP to other substrates, and especially to hydroxyl groups therein, for example sorafenib (Nexavar) or imatinib (Gleevec).

Angiogenesis inhibitors, e.g. avastin, reduce or block new vessel formation and hence the perfusion of a tumour.

Cytostatics, e.g. cis-platin, taxol, Taxotere, sagopilone, ixabepilone, are natural or synthetic substances which drive tumour cells to apoptosis.

Gestagens in the context of the present invention are understood to mean either natural progesterone itself or synthetic derivatives which, like progesterone itself, bind to the progesterone receptor and inhibit ovulation in doses above the ovulation-inhibiting dose. Examples of synthetic derivatives include drospirenone, gestodene, levonorgestrel, cyproterone acetate, desogestrel and 3-ketodesogestrel, norethisterone, norethisterone acetate and dienogest.

Combinations of gestagens and oestrogens are active ingredient combinations present in the oral contraceptive known per se, for example Yasmin, Femovan, Triquilar, Marvelon, YAZ etc.

The efficacy of the inventive compounds as progesterone receptor antagonists was demonstrated in vitro in transactivation tests and in vivo in rats (termination of early pregnancy).

Particular preference is given in accordance with the invention to the following compounds, the preparation of which is described in the examples:

(8S,11R,13S,14S,17S)-17-hydroxy-11-[4-(3-hydroxyprop-1-yn-1-yl)phenyl]-13-methyl-17-pentafluoroethyl-1,2,6,7,8,11,12,13,14,15,16,17-dodecahydrocyclopenta[a]phenanthren-3-one (Example 1)

[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynoic acid (Example 2)

[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynoic acid methyl ester (Example 3)

(E)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]pent-2-en-4-ynenitrile (Example 4)

(Z)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]pent-2-en-4-ynenitrile (Example 5)

(E)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]pent-2-en-4-ynoic acid ethyl ester (Example 6)

7-(2E/Z,4E/Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]hepta-2,4-dien-6-ynoic acid ethyl ester (Example 7)

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxy}acetic acid tert-butyl ester (Example 8)

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxy}acetic acid methyl ester (Example 9)

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxy}acetic acid (Example 10)

(8S,11R,13S,14S,17S)-17-hydroxy-11-{4-[3-(2-hydroxyethoxy)prop-1-yn-1-yl]phenyl}-13-methyl-17-pentafluoroethyl-1,2,6,7,8,11,12,13,14,15,16,17-dodecahydrocyclopenta[a]phenanthren-3-one (Example 11)

3-{(E/Z)-4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]but-1-en-3-ynyl}benzoic acid methyl ester (Example 12)

3-{(E)-4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]but-1-en-3-ynyl}benzoic acid (Example 13A)

3-{(Z)-4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]but-1-en-3-ynyl}benzoic acid (Example 13B)

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxy}acetonitrile (Example 14)

4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid methyl ester (Example 15)

4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid (Example 16)

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid methyl ester (Example 17)

(8S,11R,13S,14S,17S)-17-hydroxy-13-methyl-17-pentafluoroethyl-11-{4-[3-(1H-tetrazol-5-ylmethoxy)prop-1-yn-1-yl]phenyl}-1,2,6,7,8,11,12,13,14,15,16,17-dodecahydrocyclopenta[a]phenanthren-3-one (Example 18)

4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid (Example 19)

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid (Example 20)

(8S,11R,13S,14S,17S)-17-hydroxy-11-[4-(3-hydroxy-3-methylbut-1-ynyl)phenyl]-13-methyl-17-pentafluoroethyl-1,2,6,7,8,11,12,13,14,15,16,17-dodecahydrocyclopenta[a]phenanthren-3-one (Example 21)

(8S,11R,13S,14S,17S)-11-(4-ethynylphenyl)-17-hydroxy-13-methyl-17-pentafluoroethyl-1,2,6,7,8,11,12,13,14,15,16,17-dodecahydrocyclopenta[a]phenanthren-3-one (Example 22)

(8S,11R,13S,14S,17S)-11-[4-(3-azidoprop-1-yn-1-yl)phenyl]-17-hydroxy-13-methyl-17-pentafluoroethyl-1,2,6,7,8,11,12,13,14,15,16,17-dodecahydrocyclopenta[a]phenanthren-3-one (Example 23)

(E)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-benzyl oxime (Example 24A)

and (Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-benzyl oxime (Example 24B)

(E)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-ethyl oxime (Example 25A)

(Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-ethyl oxime (Example 25B)

[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-isobutyl oxime (Example 26)

[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-(3,4-dichlorobenzyl) oxime (Example 27)

1-(3,5-dimethylisoxazol-4-yl)-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}urea (Example 28)

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-isopropylurea (Example 29)

3-(3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}ureido)propionic acid ethyl ester (Example 30)

1-ethyl-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}urea (Example 31)

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-methoxyphenyl)urea (Example 32)

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-tert-butylphenyl)urea (Example 33)

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-phenylurea (Example 34)

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-chlorophenyl)urea (Example 35)

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-fluorophenyl)urea (Example 36)

4-(3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}ureido)benzoic acid ethyl ester (Example 37)

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-methylphenyl)urea (Example 38)

1-benzyl-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}urea (Example 39)

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-tert-butylurea (Example 40)

1-allyl-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}urea (Example 41)

(3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}ureido)acetic acid ethyl ester (Example 42)

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-piperidin-1-yl-phenyl)urea (Example 43)

allylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 44)

ethylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 45)

phenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 46)

4-methylphenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 47)

4-fluorophenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 48)

isopropylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 49)

benzylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 50)

(8S,11R,13S,14S,17S)-17-hydroxy-11-[4-(3-methanesulphonyl-phenylethynyl)phenyl]-13-methyl-17-pentafluoroethyl-1,2,6,7,8,11,12,13,14,15,16,17-dodecahydrocyclopenta[a]phenanthren-3-one (Example 51)

4-methoxyphenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 52)

4-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxycarbonylamino}benzoic acid ethyl ester (Example 53)

(4-piperidin-1-ylphenyl)carbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 54)

4-chlorophenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 55)

(8S,11R,13S,14S,17S)-17-hydroxy-11-[4-(4-methanesulphonylphenylethynyl)phenyl]-13-methyl-17-pentafluoroethyl-1,2,6,7,8,11,12,13,14,15,16,17-dodecahydrocyclopenta[a]phenanthren-3-one (Example 56)

3-pyridylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 57)

tert-butylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 58)

4-tert-butylphenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester (Example 59)

The specific radical definitions given in the particular combinations or preferred combinations of radicals are, irrespective of the particular combinations of radicals specified, also replaced as desired by radical definitions of other combinations.

Very particular preference is given to combinations of two or more of the abovementioned preferred ranges.

The invention further relates to a process for preparing the inventive derivatives of the formula I. Such derivatives can be prepared as shown in Scheme 1, by converting a phenyl sulphonate of the general formula II in which $R^{1'}$ is a perfluorinated $C_1$-$C_{10}$-alkyl group, X' is an oxygen atom, two alkoxy groups $OR^7$, a $C_2$-$C_{10}$-alkylene-, -dioxy group which may be straight-chain or branched, $R^7$ is $C_1$-$C_4$-alkyl, $R^8$ is hydrogen, $R^9$ is a hydroxyl group, or $R^8$, $R^9$ together are a bond, by palladium-catalysed coupling reactions to a compound of the general formula I' in which $R^1$, X', $R^8$ and $R^9$ are each as defined above, and any functionalities present in $R^1$ are converted and/or further conversion reactions are conducted, and the X group when defined as oxygen is optionally released from the X' group and/or a double bond ($R^8$, $R^9$ together are a bond) by elimination of water ($R^8$=hydrogen, $R^9$=hydroxyl group) is obtained and the carbonyl group (X=oxygen) is optionally functionalized further (X=$NOR^6$ or an $NNHSO_2R^6$ group).

Scheme 1

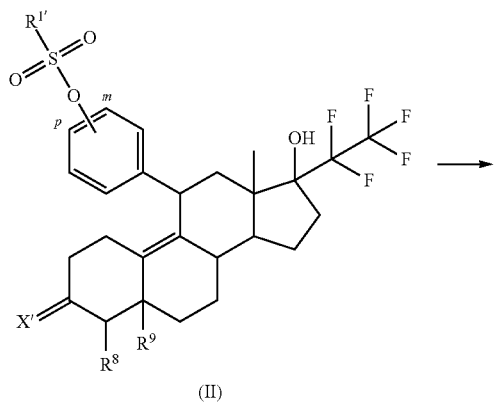

(II)

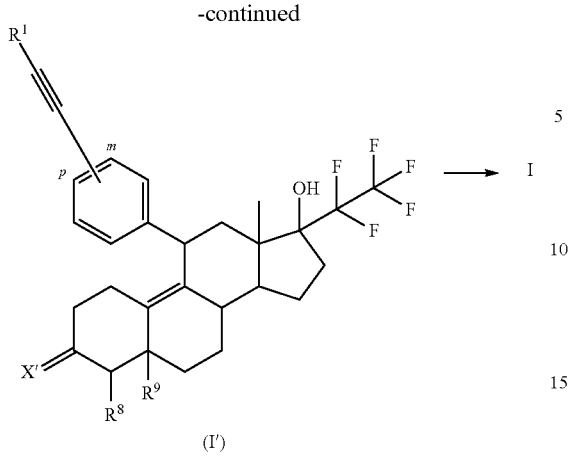

(I′)

If R[8] and R[9] together constitute a bond in the structure of the general formula I′, these represent the three possible double bond isomers I′-A, I′-B and I′-C which can form in a wide variety of different ratios relative to one another during the reactions described.

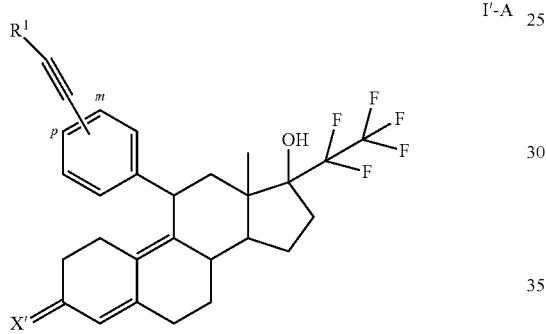

I′-A

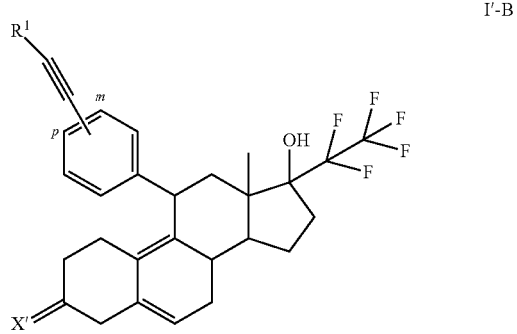

I′-B

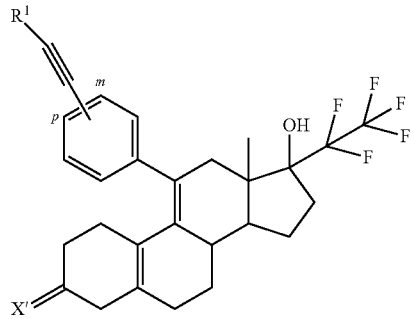

I′-C

Some possible reaction sequences to give compounds of the general formula I′ are shown in detail by way of example in Scheme 2.

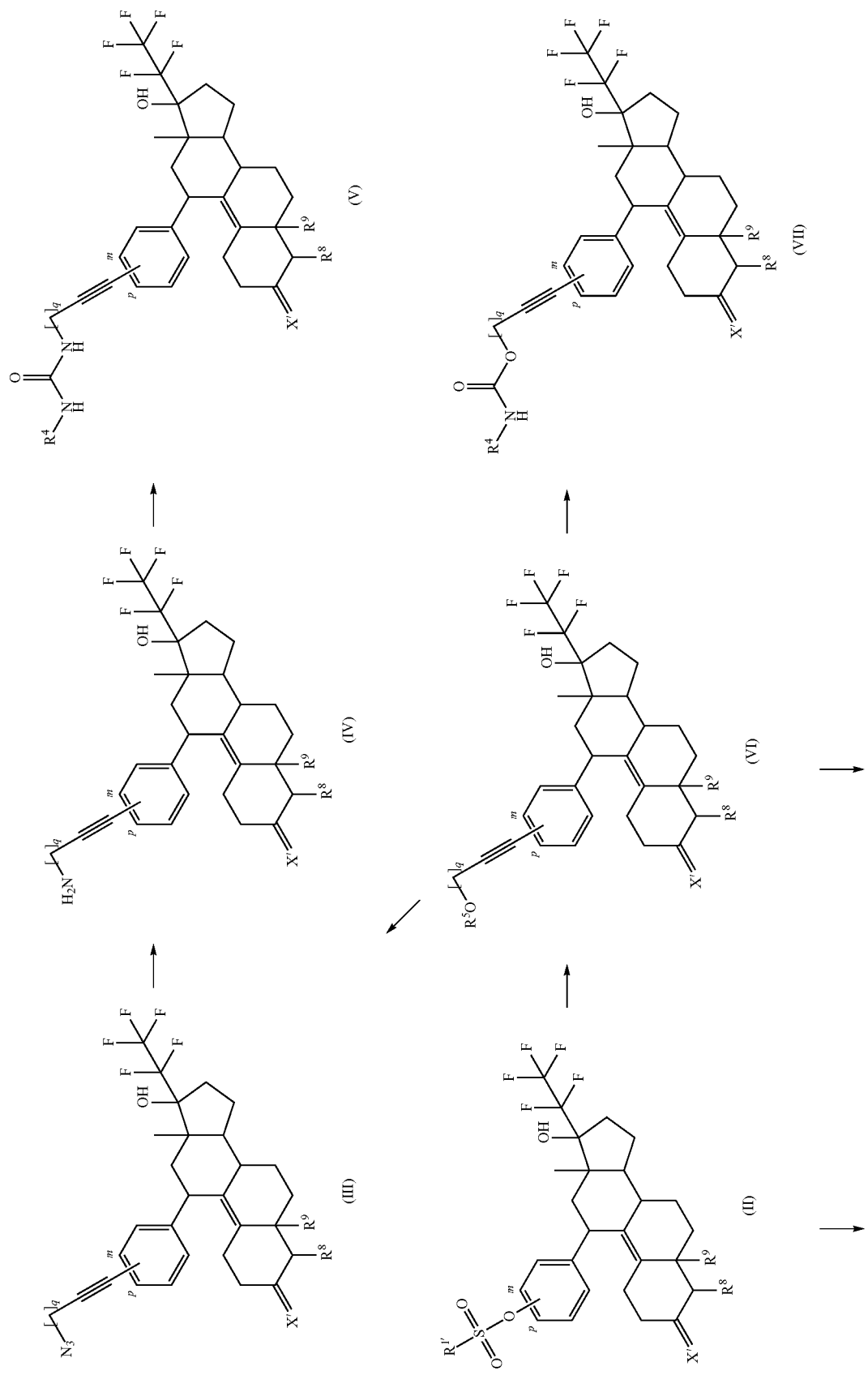

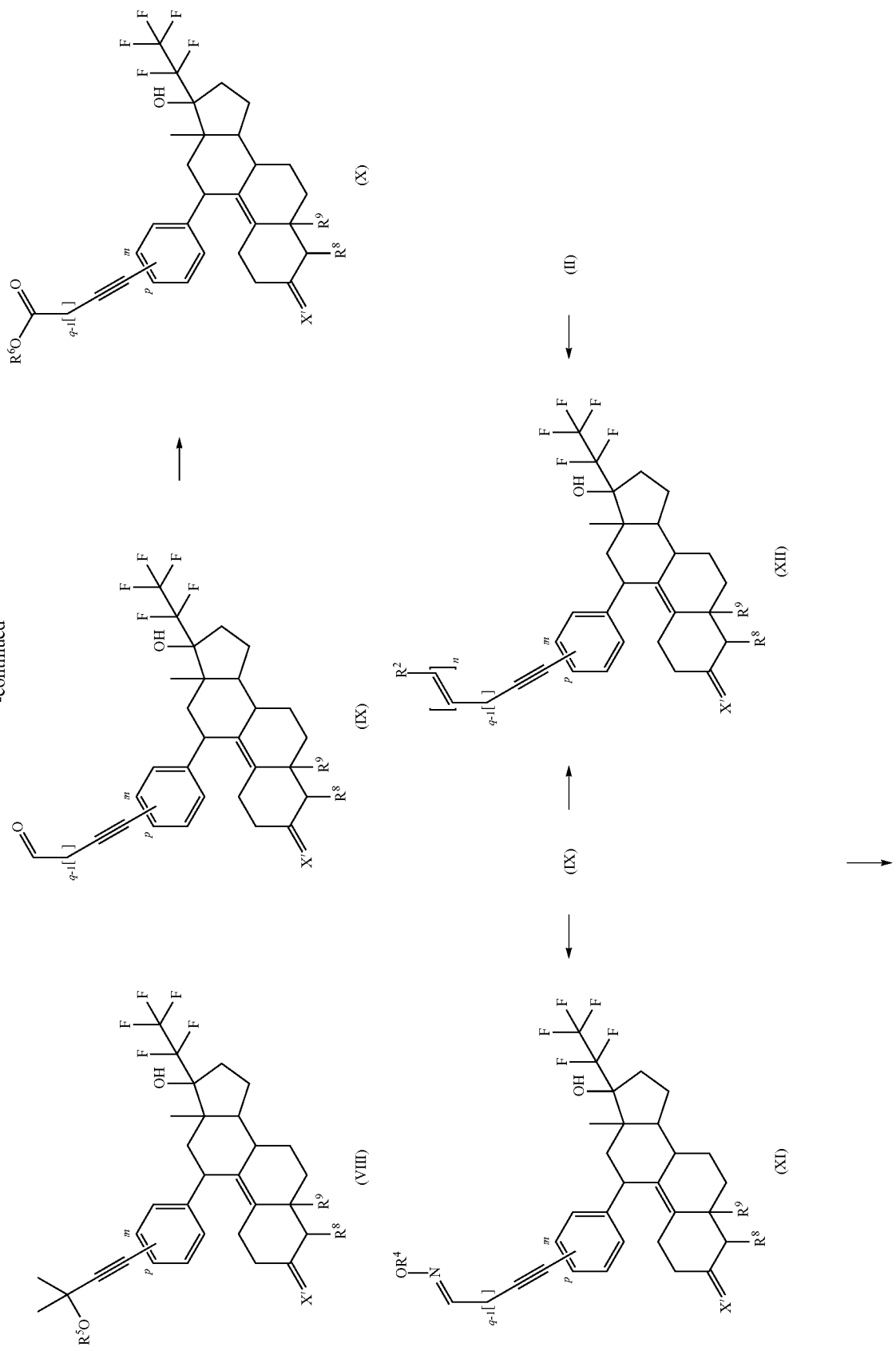

-continued
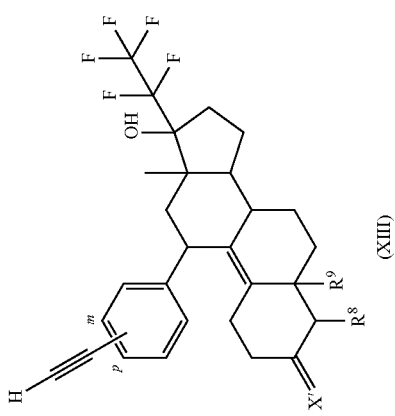
(XIII)
III, IV, V, VI, VII, VIII, X, XI, XII, XIII ⟶ I

Compounds of the general formula II are converted to compounds of the general formulae VI, VIII or XII by palladium-catalysed coupling reactions by the methods known to those skilled in the art. Typical methods can be found in Examples 1a, 15a, 17b and 19.

Compounds of the general formula VI are converted to compounds of the general formula VII (a) by reaction of the alcohol with isocyanates or (b) in two stages by preparing the chloroformic ester and further reaction with amines by the methods known to those skilled in the art. Typical methods for (a) can be found in Examples 44a to 49a, and for (b) in Examples 50, 52-55 and 57-59.

Compounds of the general formula IV are converted to compounds of the general formula V with isocyanates by the methods known to those skilled in the art. Typical methods can be found in Examples 28-43.

Compounds of the general formula VI are converted to compounds of the general formulae X (a) either by direct oxidation or (b) by a two-stage oxidation to form the aldehyde of the general formula IX and subsequent oxidation to give X by the methods known to those skilled in the art. One example is direct oxidation with Jones reagent. Typical methods for (b) can be found in Examples 2a and 2.

Compounds of the general formula IX are converted to compounds of the general formula XI by the methods known to those skilled in the art. Typical methods can be found in Examples 24a-27a.

Compounds of the general formula IX are converted to compounds of the general formula XII by the methods known to those skilled in the art. Typical methods can be found in Examples 4a, 6a, 7a and 12a.

Compounds of the general formula IX are converted to compounds of the general formula XIII by the methods known to those skilled in the art. A typical method can be found in Example 22a.

If not already accomplished by the reactions described, any ketals present in the compounds of the general formulae III, IV, V, VI, VII, VIII, X, XI, XII, XIII are cleaved to give X' and/or, if $R^8$ is defined as hydrogen and $R^9$ is defined as hydroxyl, water is eliminated. A typical method can be found in Examples 1 and 28.

If the preparation of the starting compounds is not described here, they are known to those skilled in the art or can be prepared analogously to known compounds or processes described here (see also Examples 1b to 1e).

The salts are prepared in a customary manner, by admixing a solution of the compounds of the general chemical formula I with the equivalent amount or an excess of a base or acid which may be in solution, optionally removing the precipitate or working up the solution in a customary manner.

The pharmaceutical formulations based on the novel compounds are formulated in a manner known per se, by processing the active ingredient with the pharmaceutical standard carrier substances, fillers, decomposition influencers, binders, humectants, lubricants, absorbents, diluents, taste correctors, colourants, etc., and converted to the desired administration form. Reference should be made to Remington's Pharmaceutical Science, 15th ed. Mack Publishing Company, East Pennsylvania (1980).

The inventive compounds may act systemically and/or locally. For this purpose, they can be administered in a suitable manner, for example by an oral, intrauterine, intravaginal, parenteral, pulmonary, nasal, sublingual, lingual, buccal, rectal, dermal, transdermal, conjunctival or otic route, or as an implant or stent.

"Intrauterine" means especially administration by means of an IUS (intrauterine system) or IUD (intrauterine device). One method of intravaginal administration is by means of an IVR/VRS (intravaginal ring/vaginal ring system).

Intrauterine or intravaginal administration forms (cf., for example, WO 01/47490, especially page 1 line 10 to page 5 line 13 and page 7 line 19 to page 58 line 6, or for vaginal rings: WO 06/010097, especially page 10 line 22 to page 14 line 28) may comprise the inventive compounds and nonsilicone and/or silicone polymers, especially also siloxane-based elastomers (cf. WO 01/47490, especially page 7 line 19-page 15 line 15).

For these administration routes, the inventive compounds can be administered in suitable administration forms.

Suitable administration forms for oral administration are those which release the inventive compounds in a rapid and/or modified manner, work according to the prior art and contain the inventive compounds in crystalline and/or amorphous and/or dissolved form, for example tablets (uncoated or coated tablets, for example with enteric or retarded-dissolution or insoluble coatings which control the release of the inventive compound), tablets or films/wafers which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardial, intraspinal or intralumbar route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilisates or sterile powders.

For the other administration routes, suitable examples are inhalation medicaments (including powder inhalers, nebulizers), nasal drops, solutions or sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (for example patches), milk, pastes, foams, dusting powders, implants or stents.

The inventive compounds can be converted to the administration forms listed. This can be accomplished in a manner known per se by mixing with inert nontoxic pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and taste and/or odour correctors.

The present invention further provides medicaments which comprise at least one inventive compound, typically together with one or more inert nontoxic pharmaceutically suitable excipients, and for the use thereof for the aforementioned purposes.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

The percentages in the tests and examples which follow are percentages by weight unless stated otherwise; parts are parts by weight. Solvent ratios, dilution ratios and concentration figures for liquid/liquid solutions are each based on volume.

The examples which follow serve to illustrate the invention without restricting it in any way.

EXAMPLE 1

(8S,11R,13S,14S,17S)-17-hydroxy-11-[4-(3-hydroxyprop-1-yn-1-yl)phenyl]-13-methyl-17-pentafluoroethyl-1,2,6,7,8,11,12,13,14,15,16,17-dodecahydrocyclopenta[a]phenanthren-3-one

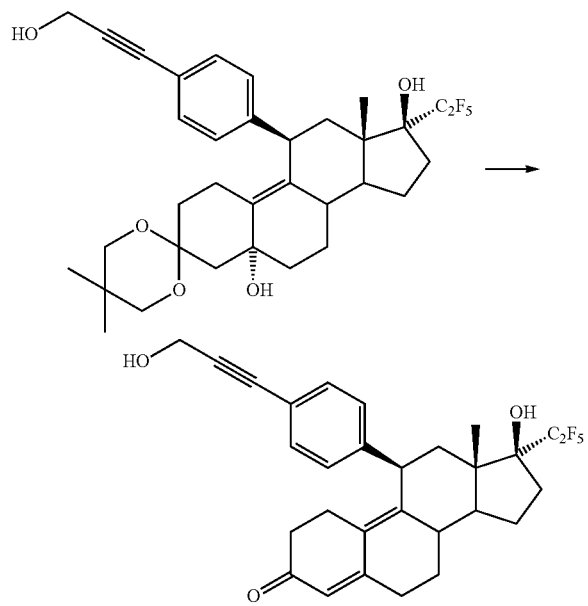

The solution of 200 mg (0.32 mmol) of the compound prepared according to Example 1a in 10.4 ml of acetone was admixed with 480 ml of 4N hydrochloric acid and the mixture was stirred at 23° C. for 20 minutes. The mixture was poured into a saturated sodium hydrogencarbonate solution and extracted repeatedly with ethyl acetate, the combined organic extracts were dried over sodium sulphate and the residue obtained after filtration and removal of solvent was purified by chromatography. 133 mg (80%) of the title compound were isolated as a colourless foam.

$^1$H NMR (CDCl$_3$):=0.58 (3H), 1.40-1.55 (2H), 1.71-1.85 (4H), 2.02-2.63 (11H), 2.72 (1H), 4.43 (1H), 4.49 (2H), 5.79 (1H), 7.13 (2H), 7.36 (2H) ppm.

EXAMPLE 1a (5R,8S,11R,13S,14S,17S)-11-[4-(3-hydroxyprop-1-yn-1-yl)phenyl]-5',5',13-trimethyl-17-(pentafluoroethyl)-1,2,3,4,6,7,8,11,12,13,14,15,16,17-tetradecahydro-spiro[cyclopenta[a]phenanthrene-3,2'-[1,3]dioxane]-5,17-diol

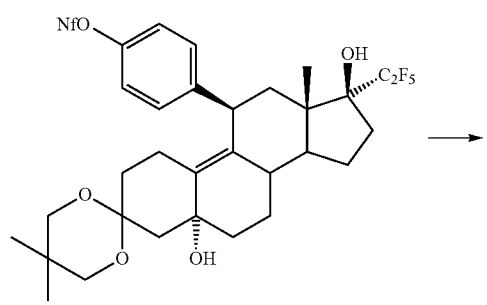

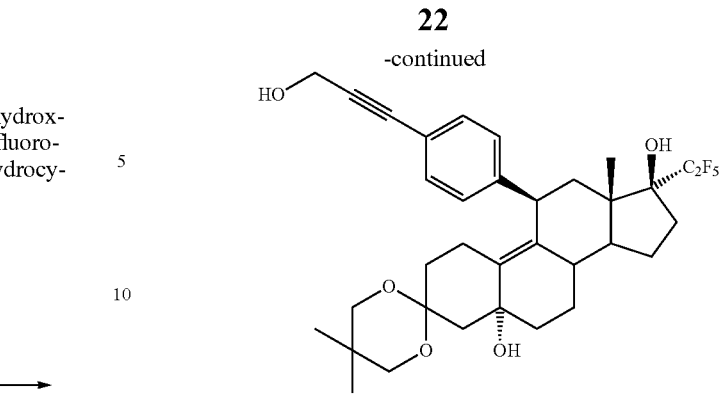

The solution of 34.4 g (39.6 mmol) of the compound prepared according to Example 1b in 435 ml of tetrahydrofuran was admixed with 19.6 ml of piperidine, 4.58 g of tetrakis(triphenylphosphine)palladium(0), 11.7 ml of propargyl alcohol, and the mixture was heated to 80° C. for 1 hour. The mixture was poured into a saturated ammonium chloride solution and extracted repeatedly with ethyl acetate, and the combined organic extracts were washed with saturated ammonium chloride and sodium chloride solution and dried over sodium sulphate. The residue obtained after filtration and removal of solvent was purified by chromatography. 4.53 g (18%) of the title compound were isolated as a colourless foam.

EXAMPLE 1b 1,1,2,2,3,3,4,4,4-nonafluorobutane-1-sulphonic acid 4-((5R,8S,11R,13S,14S,17S)-5,17-dihydroxy-5',5',13-trimethyl-17-(pentafluoroethyl)-1,2,3,4,6,7,8,11,12,13,14,15,16,17-tetradecahydrospiro[cyclopenta[a]phenanthrene-3,2'-[1,3]dioxane]-11-yl)phenyl ester

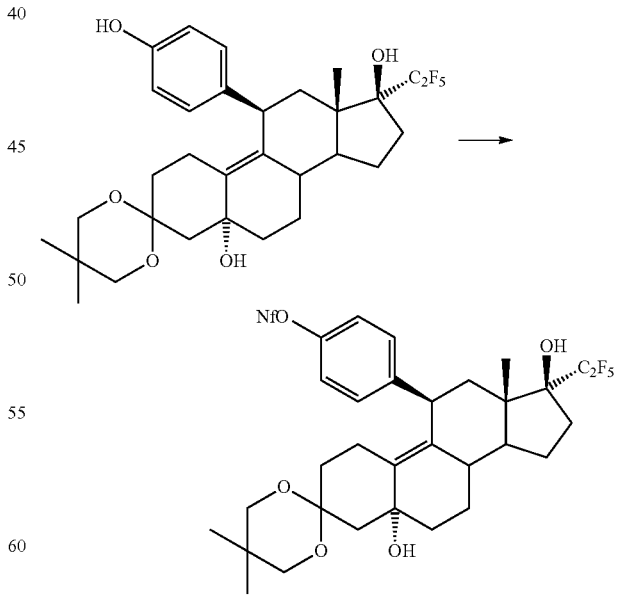

To a solution of 25 g (43 mmol) of the compound prepared according to Example 1c in 590 ml of tetrahydrofuran were added, at −10° C., 26.4 ml of a 1.6 molar solution of n-butyllithium in hexane. The mixture was left to stir at 0° C. for a further 30 minutes, 15.5 ml of perfluorobutane-1-sulphonyl fluoride were added and the mixture was left to stir at 0° C. for a further 1.5 hours. 10 ml of triethylamine were added, the mixture was poured into a saturated sodium hydrogencarbonate solution and the mixture was stirred at 23° C. for 16 hours. Another 10 ml of triethylamine were added and the mixture was extracted repeatedly with diethyl ether. The combined organic extracts were washed with saturated sodium chloride solution and dried over sodium sulphate, and the residue obtained after filtration and removal of solvent was purified by chromatography. 31.8 g (82%) of the title compound were isolated as a pale yellow foam.

EXAMPLE 1c ((5R,8S,11R,13S,14S,17S)-11-(4-hydroxyphenyl)-5, 17-dihydroxy-5',5',13-trimethyl-17-(pentafluoroethyl)-1,2,3,4,6,7,8,11,12,13,14,15,16,17-tetradecahydro-spiro[cyclopenta[a]phenanthrene-3,2'-[1,3]dioxane]

and removal of solvent was purified by crystallization. 53.3 g (95%) of the title compound were isolated as a colourless solid.

EXAMPLE 1d ((5R,8S,11R,13S,14S,17S)-11-[4-(phenylmethoxy)phenyl]-5,17-dihydroxy-5',5',13-trimethyl-17-(pentafluoroethyl)-1,2,3,4,6,7,8,11,12,13,14,15,16,17-tetradecahydro-spiro[cyclopenta[a]phenanthrene-3, 2'-[1,3]dioxane]

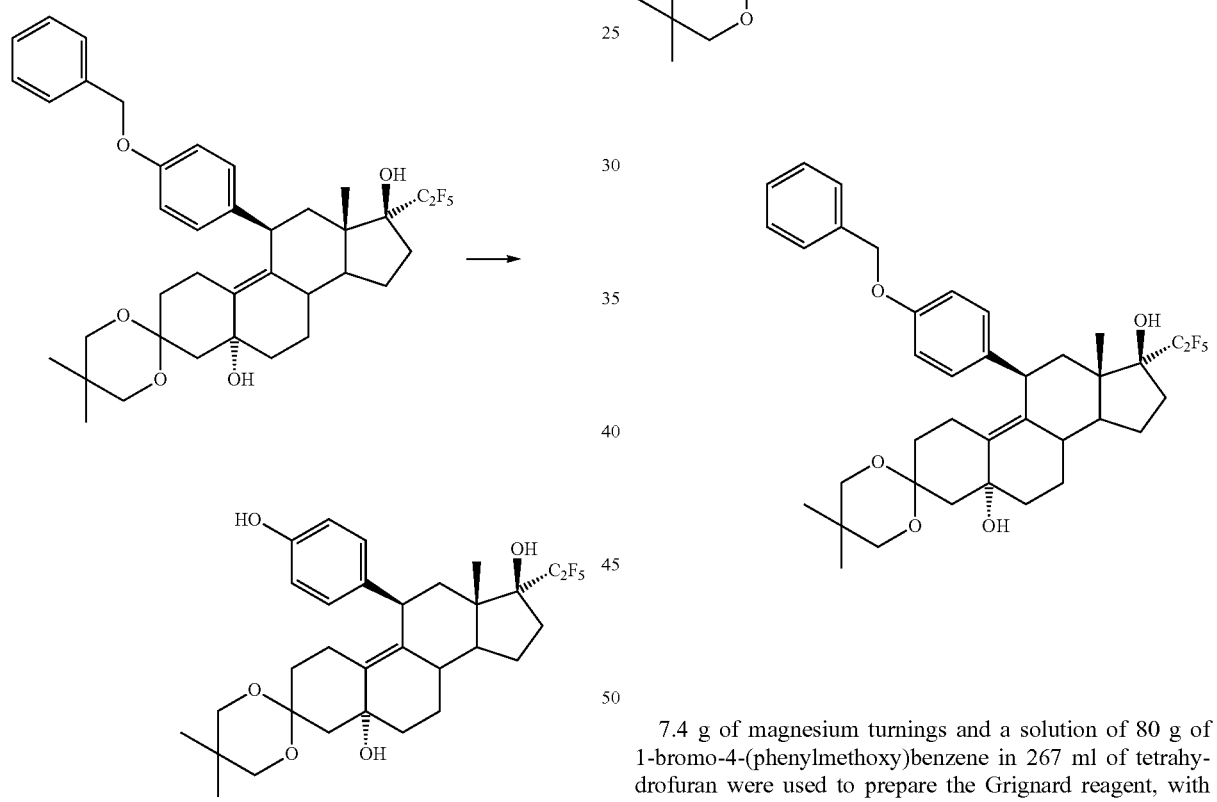

The solution of 90 g (96 mmol) of the compound prepared according to Example 1d and 30.3 g of ammonium formate in 600 ml of methanol was admixed with a suspension of 6.5 g of palladium on activated carbon (10%) in 80 ml of methanol and the mixture was stirred at 23° C. for 2 hours. It was diluted with dichloromethane, filtered through Celite and concentrated. The residue was dissolved in ethyl acetate, washed with water and saturated sodium chloride solution and dried over sodium sulphate. The residue obtained after filtration 7.4 g of magnesium turnings and a solution of 80 g of 1-bromo-4-(phenylmethoxy)benzene in 267 ml of tetrahydrofuran were used to prepare the Grignard reagent, with heating to 50-80° C. and optionally with addition of an iodine crystal and/or catalytic amounts of 1,2-dibromoethane. The mixture was cooled to 0° C. and admixed with 1.51 g of copper(I) chloride, and the solution of 50 g (102 mmol) of the compound prepared according to Example 1e in 500 ml of tetrahydrofuran was added dropwise. The mixture was stirred at 23° C. for another 16 hours, poured into a saturated ammonium chloride solution and extracted repeatedly with ethyl acetate. The combined organic extracts were washed with saturated sodium chloride solution and dried over sodium sulphate. The solid obtained after filtration and removal of solvent was purified by crystallization, and 47.7 g (69%) of the title compound were isolated as a colourless solid.

EXAMPLE 1e (5R,8S,10R,13S,14S,17S)-17-(pentafluoroethyl)-5, 10-epoxy-5',5',13-trimethyl-1,2,3,4,6,7,8,12,13,14, 15,16,17-tridecahydrospiro[cyclopenta[a]phenan- threne-3,2'-[1,3]dioxane]-17-ol

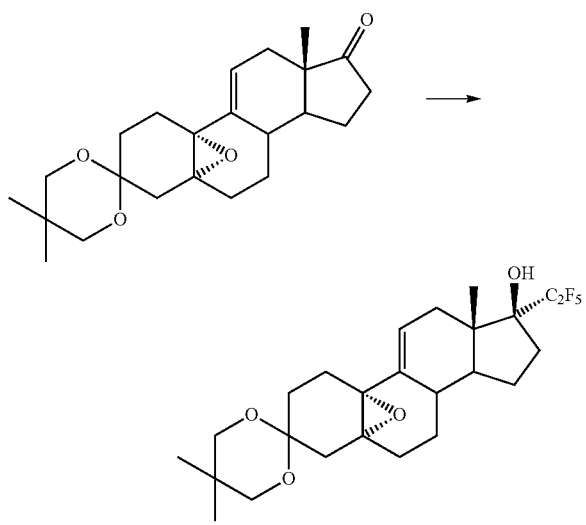

The solution of 10.0 g (27 mmol) of (5'R,8'S,10'R,13'S, 14'S)-5',5',13'-trimethyl-1',2',6',7',8',12',13',14',15',16'- decahydro-17'H-spiro[1,3-d]oxane-2,3'-[5,10]epoxycyclo- penta[a]phenanthrene]-17'-one, which was prepared in analogy to the process described in Tetrahedron Lett. 26, 2069-2072 (1985), in 145 ml of dichloromethane was cooled to −70° C. and admixed with 11.1 ml of pentafluoroiodoet- hane which had been condensed beforehand, and 54 ml of a 1.5 molar solution of methyllithium-lithium bromide com- plex in diethyl ether were slowly added dropwise. After 1 hour, the mixture was poured into water, extracted with dichloromethane, washed with water and sodium chloride solution, and dried over sodium sulphate. After filtration and removal of solvent, 12.9 g (98%) of the title compound were isolated, which were converted further without purification.

EXAMPLE 2

[4-((8S,11R,13S,14S,17S)-17-hydroxy-13-methyl-3- oxo-17-pentafluoroethyl-2,3,6,7,8,11,12,13,14,15, 16,17-dodecahydro-4H-cyclopenta[a]phenanthren- 11-yl)phenyl]propynoic acid

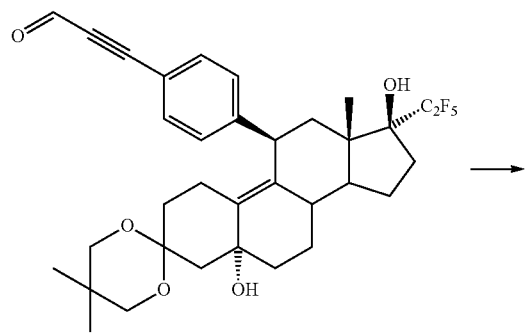

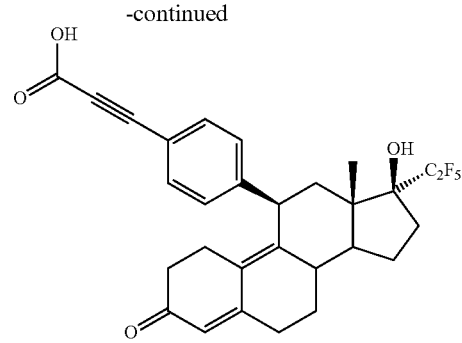

The solution of 38 mg (61 μmol) of the compound prepared according to Example 2a in 2 ml of tert-butanol and 1.4 ml of tetrahydrofuran, while cooling with an ice bath, was admixed with 0.4 ml of 2-methyl-2-butene, 0.48 ml of water, 25.3 mg of sodium dihydrogenphosphate monohydrate and 42.6 mg of sodium chlorite. The mixture was left to react for 1 hour, poured into water, saturated with sodium chloride and extracted repeatedly with ethyl acetate. The combined organic extracts were dried over sodium sulphate, and the residue obtained after filtration and removal of solvent was purified by chromatography. 7.7 mg (24%) of the title com- pound were isolated as a colourless foam.

$^1$H NMR (CDCl$_3$):=0.56 (3H), 1.35-1.55 (2H), 1.69-2.80 (15H), 4.39 (1H), 3.31-3.93 (>1H), 5.74 (1H), 7.13 (2H). 7.35 (2H) ppm.

EXAMPLE 2a

3-{4-[(5R,8S,11R,13S,14S,17S)-5,17-dihydroxy-5', 5',13-trimethyl-17-(pentafluoroethyl)-1,2,4,5,6,7,8, 11,12,13,14,15,16,17-tetradecahydrospiro[cyclo- penta[a]phenanthrene-3,2'-[1,3]dioxane]-11-yl] phenyl}propynal

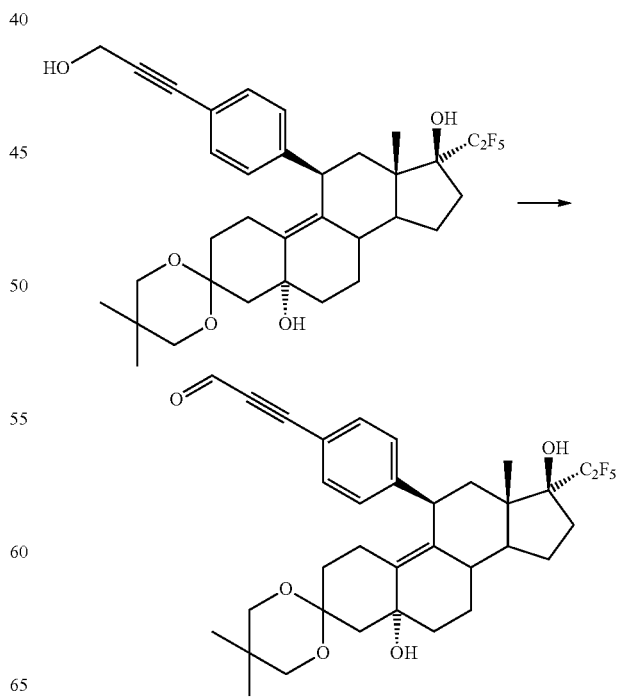

The solution of 2.0 g (3.2 mmol) of the compound prepared according to Example 1a in 50 ml of dichloromethane was admixed with a few beads of 4 Å molecular sieve, 560 mg of N-methylmorpholine N-oxide, 85 mg of tetrapropylammonium perruthenate, and the mixture was stirred at 23° C. for 1.5 hours. The mixture was purified by chromatography, and 1.44 g (72%) of the title compound were isolated as a colourless foam.

EXAMPLE 3

[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]propynoic acid methyl ester

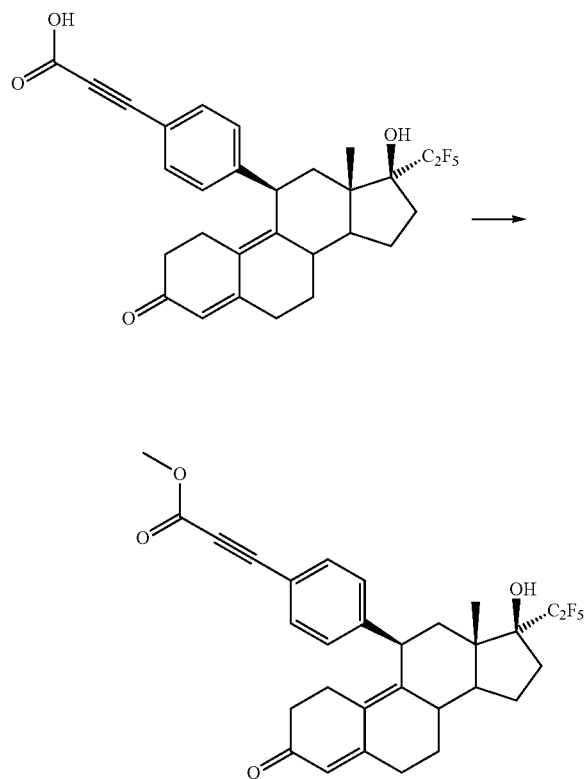

The solution of 62 mg (120 µmol) of the compound prepared according to Example 2 in 1 ml of tetrahydrofuran was admixed at 3° C. with 2.5 ml of an ethereal solution of diazomethane, and the mixture was stirred for 30 minutes. The residue obtained after removal of solvent was purified by chromatography, and 18 mg (28%) of the title compound were isolated as a colourless foam.

$^1$H NMR (CDCl$_3$):=0.57 (3H), 1.40-1.55 (2H), 1.74-1.86 (3H), 2.07 (1H), 2.22 (1H), 2.24-2.64 (9H), 2.71 (1H), 3.84 (3H), 4.46 (1H), 5.79 (1H), 7.21 (2H), 7.50 (2H) ppm.

EXAMPLE 4

(E)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]pent-2-en-4-ynenitrile

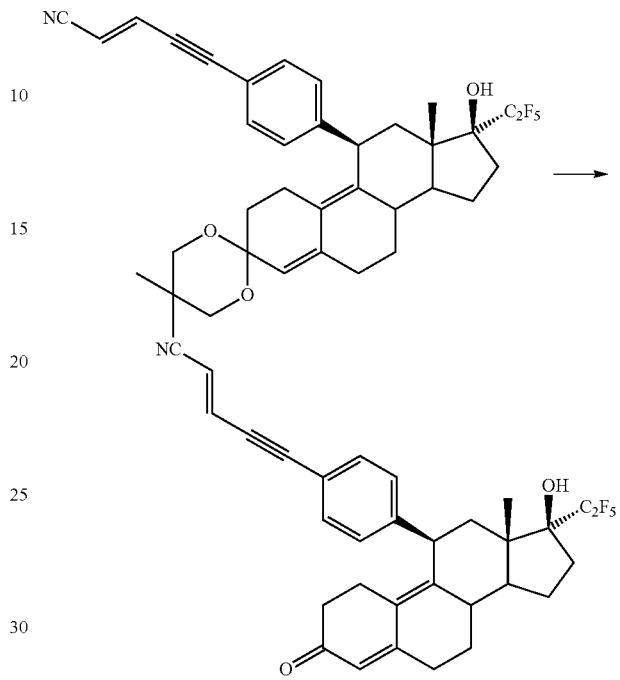

In analogy to Example 1, 125 mg (0.2 mmol) of the compound A prepared according to Example 4a were converted and, after workup and purification, 51 mg (47%) of the title compound were isolated as a colourless foam.

$^1$H NMR (CDCl$_3$):=0.58 (3H), 1.40-1.56 (2H), 1.73-1.87 (3H), 2.05 (1H), 2.08 (1H), 2.19-2.65 (10H), 2.72 (1H), 4.46 (1H), 5.78 (1H), 5.80 (1H), 6.69 (1H), 7.19 (2H), 7.40 (2H) ppm.

EXAMPLE 4a (2E)-5-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydro-spiro[cyclopenta[a]phenanthrene-3,2'-[1,3]dioxane]-11-yl]phenyl}pent-2-en-4-ynenitrile (A) and (2Z)-5-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydro-spiro[cyclopenta[a]phenanthrene-3,2'-[1,3]dioxane]-11-yl]phenyl}pent-2-en-4-ynenitrile (B)

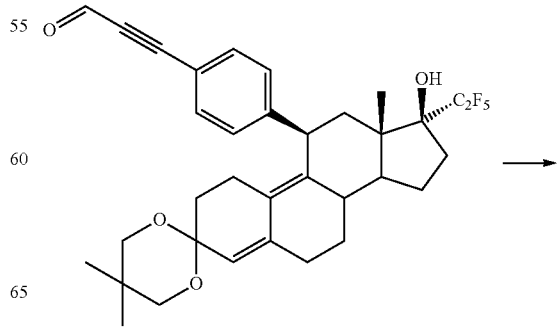

-continued

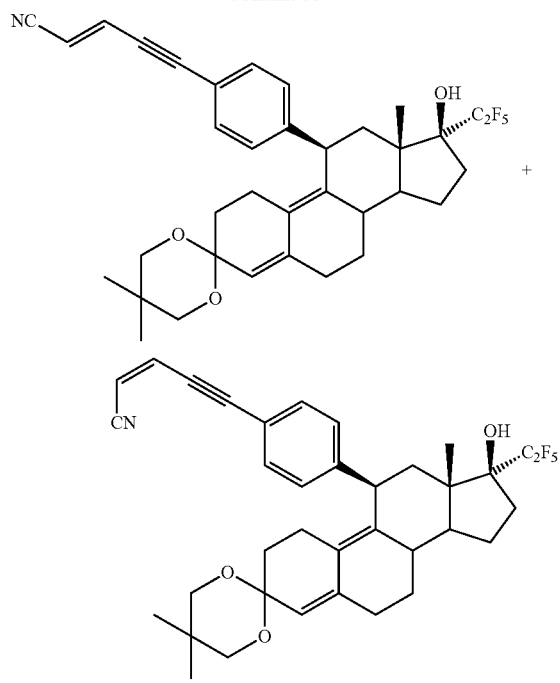

The solution of 0.2 ml of diethyl cyanomethanephosphonate in 5 ml of diethyl ether was admixed with 2.1 ml of a 0.6 molar solution of sodium bis(trimethylsilyl)amide and the mixture was stirred at 23° C. for 30 minutes. Subsequently, the solution of 500 mg (0.83 mmol) of the compound prepared according to Example 2a in 3.4 ml of diethyl ether was added dropwise and the mixture was left to react for 1 hour. The mixture was poured into water and extracted repeatedly with ethyl acetate, and the combined organic extracts were dried over sodium sulphate. The residue obtained after filtration and removal of solvent was purified by chromatography. 125 mg (24%) of title compound A and 67 mg (13%) of title compound B were isolated, each as a colourless foam.

EXAMPLE 5

(Z)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]pent-2-en-4-ynenitrile

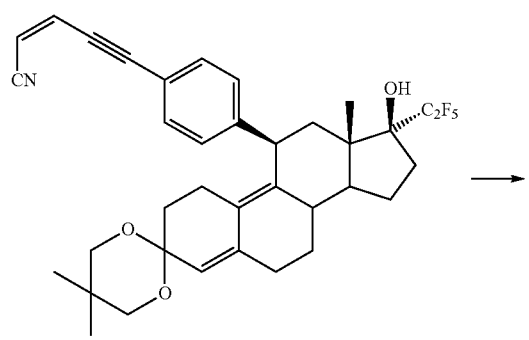

-continued

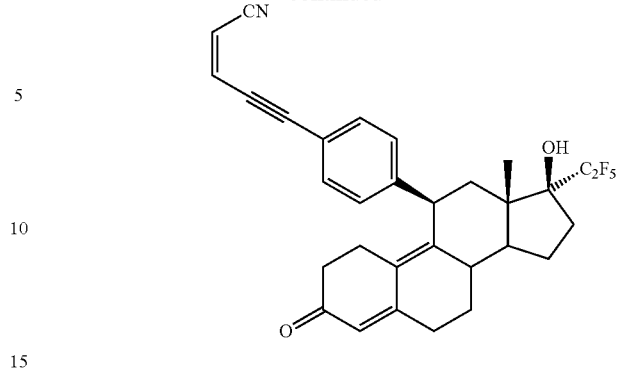

In analogy to Example 1, 10.5 mg (17 µmol) of the compound B prepared according to Example 4a were converted and, after workup and purification, 6.8 mg (62%) of the title compound were isolated as a colourless foam.

$^1$H NMR (CDCl$_3$):=0.64 (3H), 1.43-1.66 (2H), 1.77-1.92 (3H), 2.06-2.18 (2H), 2.25-2.70 (9H), 2.77 (1H), 4.51 (1H), 5.70 (1H), 5.84 (1H), 6.56 (1H), 7.25 (2H), 7.52 (2H) ppm.

EXAMPLE 6

(E)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]pent-2-en-4-ynoic acid ethyl ester

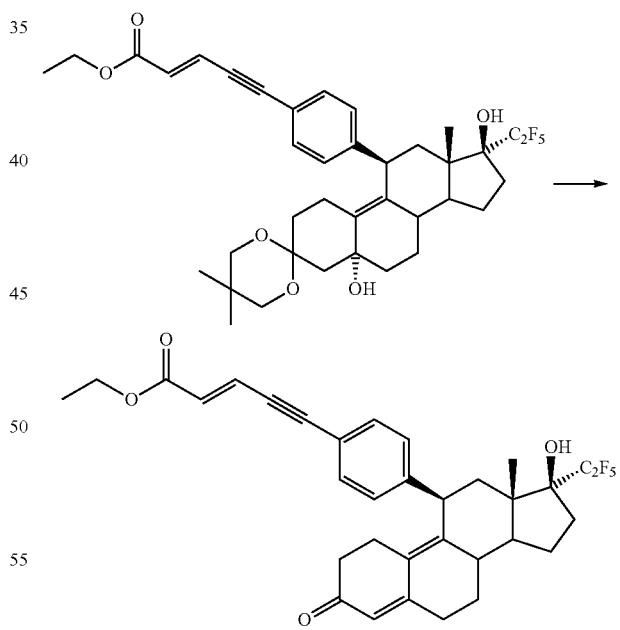

In analogy to Example 1, 56.2 mg (81 µmol) of the compound prepared according to Example 6a were converted and, after workup and purification, 24.9 mg (52%) of the title compound were isolated as a colourless foam.

$^1$H NMR (CDCl$_3$):=0.63 (3H), 1.36 (3H), 1.45-1.64 (2H), 1.76-1.97 (3H), 2.06-2.20 (2H), 2.27-2.87 (10H), 4.28 (2H), 4.50 (1H), 5.84 (1H), 6.34 (1H), 7.02 (1H), 7.22 (2H), 7.45 (2H) ppm.

EXAMPLE 6a ethyl(2E)-5-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydro-spiro[cyclopenta[a]phenanthrene-3,2'-[1,3]dioxane]-11-yl]phenyl}pent-2-en-4-ynoate

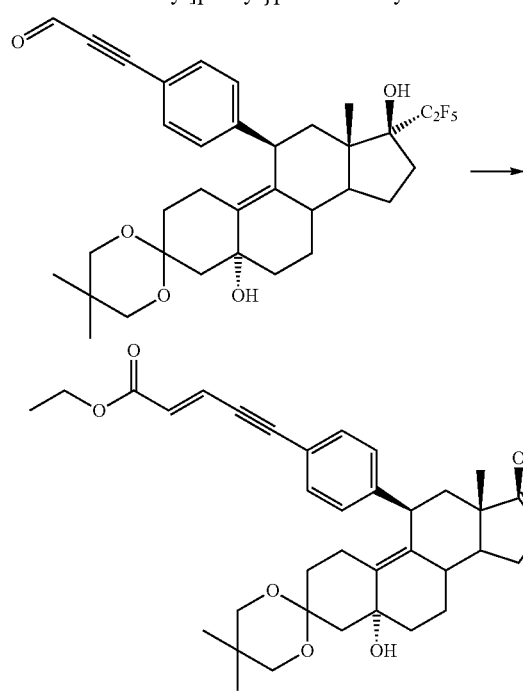

The solution of 34.5 µl of triethyl phosphonoacetate in 0.71 ml of tetrahydrofuran was admixed with 7.6 mg of a 55% suspension of sodium hydride in white oil and the mixture was stirred at 23° C. for 15 minutes. Subsequently, the solution of 70 mg (0.11 mmol) of the compound prepared according to Example 2a in 1.4 ml of tetrahydrofuran was added dropwise and the mixture was left to react for 1 hour. The mixture was admixed with sodium hydrogencarbonate solution and extracted repeatedly with ethyl acetate, and the combined organic extracts were dried over sodium sulphate. The residue obtained after filtration and removal of solvent was purified by chromatography. 56 mg (72%) of the title compound were isolated as a colourless foam.

EXAMPLE 7

7-(2E/Z,4E/Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]hepta-2,4-dien-6-ynoic acid ethyl ester

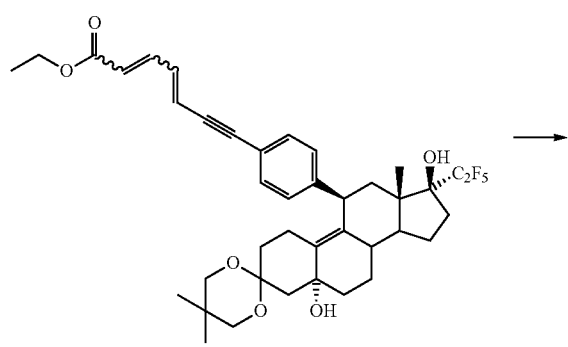

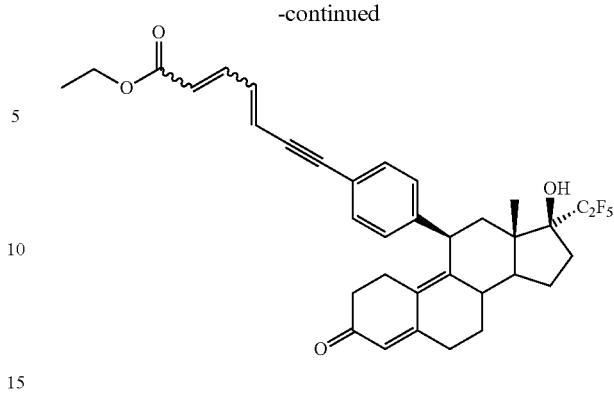

In analogy to Example 1, 11.2 mg (16 µmol) of the compounds prepared according to Example 7a were converted and, after workup and purification, 6.0 mg (63%) of the isomeric title compounds were isolated as a pale yellow foam.
$^1$H NMR (CDCl$_3$):=0.59 (3H), 1.31 (3H), 1.41-1.56 (2H), 1.73-1.86 (3H), 2.01-2.15 (2H), 2.19-2.65 (9H), 2.72 (1H), 4.23 (2H), 4.45 (1H), 5.79 (1H), 5.94-6.20 (2H), 6.53+6.74 (1H), 7.16 (2H), 7.30-7.45+7.86 (3H) ppm.

EXAMPLE 7a ethyl(2E/Z,4E/Z)-7-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydro-spiro[cyclopenta[a]phenanthrene-3,2'-[1,3]dioxane]-11-yl]phenyl}hepta-2,4-dien-6-ynoate

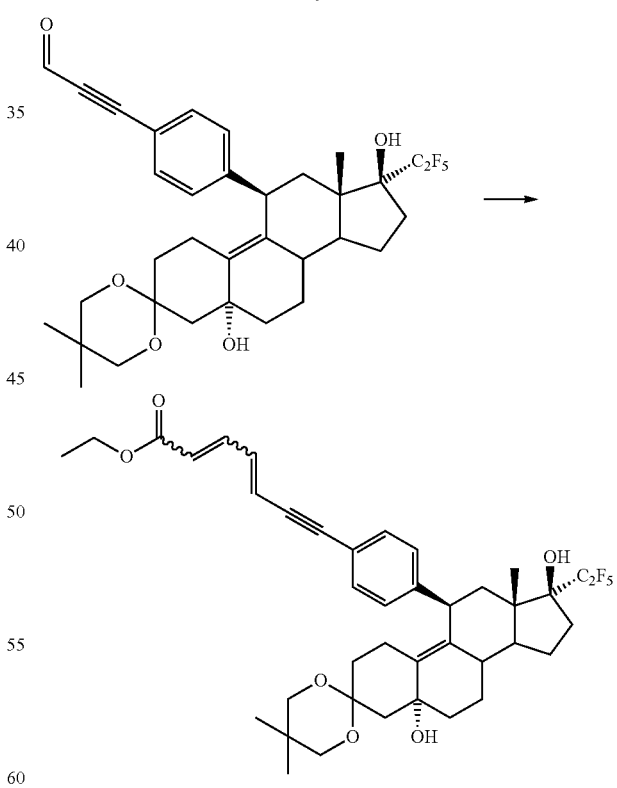

The solution of 101 mg of ethyl(E)-4-(diethoxyphosphoryl)but-2-enoate in 2.74 ml of tetrahydrofuran was admixed with 162 µl of a 1.6 molar solution of n-butyllithium in hexane, and the mixture was stirred at 23° C. for 45 minutes. Subsequently, the mixture was cooled to −78° C., the solution of 70 mg (0.11 mmol) of the compound prepared according to Example 2a in 1.42 ml of tetrahydrofuran was added dropwise, the cooling bath was removed and the mixture was left to react for 1 hour. The mixture was poured into a saturated ammonium chloride solution and extracted repeatedly with ethyl acetate, and the combined organic extracts were dried over sodium sulphate. The residue obtained after filtration and removal of solvent was purified by chromatography. 11 mg (14%) of the title compound were isolated as a colourless foam.

EXAMPLE 8

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxy}acetic acid tert-butyl ester

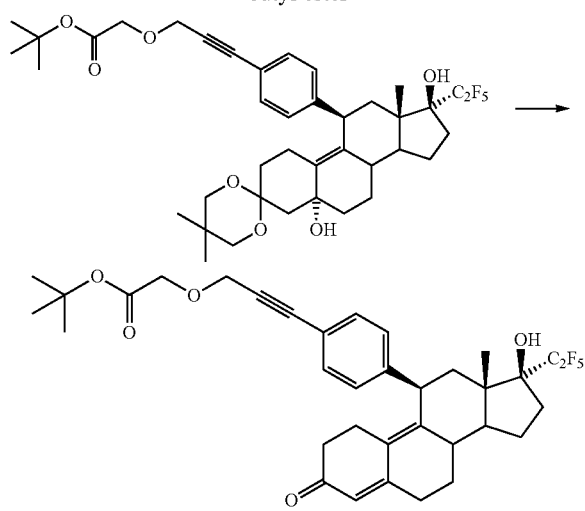

In analogy to Example 1, 50 mg (68 μmol) of the compound prepared according to Example 8a were converted and, after workup and purification, 31.3 mg (73%) of the title compound were isolated as a colourless foam.

$^1$H NMR (CDCl$_3$):=0.58 (3H), 1.49 (11H), 1.74-1.86 (3H), 2.01 (1H), 2.07 (1H), 2.22-2.64 (9H), 2.72 (1H), 4.12 (2H), 4.44 (1H), 4.51 (2H), 5.79 (1H), 7.13 (2H), 7.37 (2H) ppm.

EXAMPLE 8a tert-butyl[(3-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydrospiro[cyclopenta[a]phenanthrene-3,2'-[1,3]dioxane]-11-yl]phenyl}prop-2-yn-1-yl)oxy]acetate

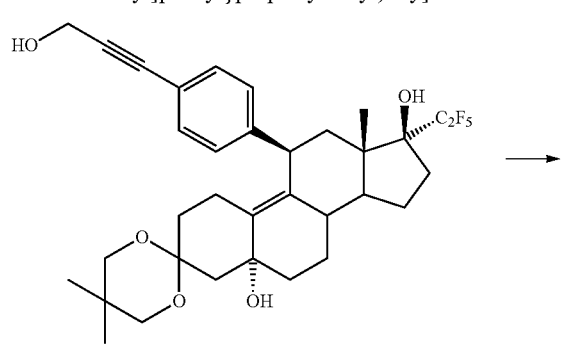

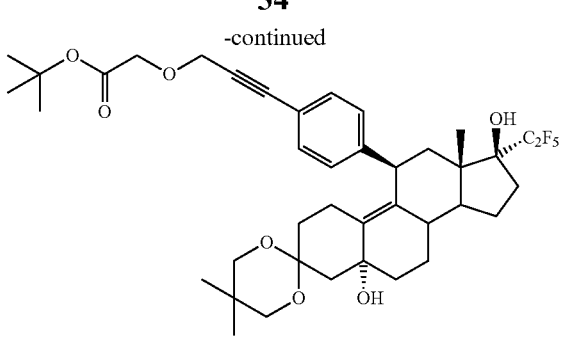

The solution of 200 mg (0.32 mmol) of the compound prepared according to Example 1a in 2 ml of dichloromethane was admixed with 0.26 ml of tert-butyl bromoacetate, 0.75 ml of a 50% potassium hydroxide solution, 4.25 mg of tetrabutylammonium hydrogensulphate, and stirred at 23° C. for 1 hour. It was diluted with water and dichloromethane, acidified by addition of 4 molar hydrochloric acid and extracted with dichloromethane. The combined organic extracts were dried over sodium sulphate. The residue obtained after filtration and removal of solvent was purified by chromatography. 206 mg (87%) of the title compound were isolated as a colourless foam.

EXAMPLE 9

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxy}acetic acid methyl ester

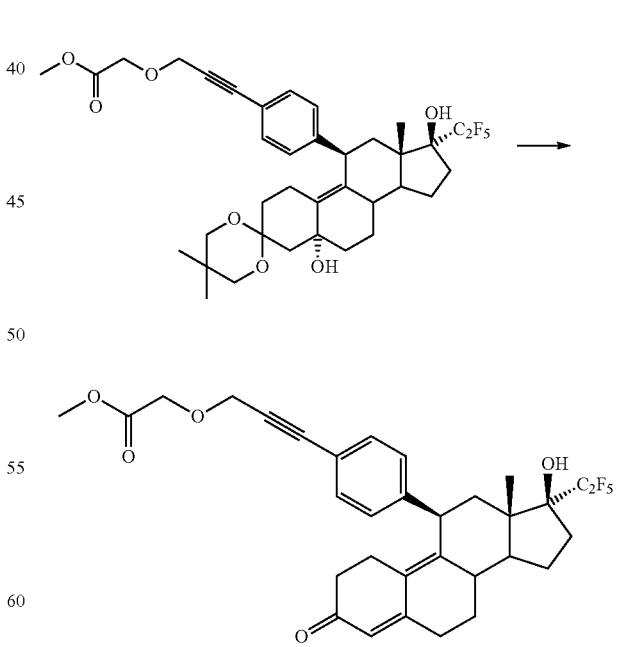

In analogy to Example 1, 32.2 mg (46 μmol) of the compound prepared according to Example 9a were converted and, after workup and purification, 18.7 mg (68%) of the title compound were isolated as a colourless foam.

¹H NMR (CDCl₃):=0.58 (3H), 1.39-1.56 (2H), 1.73-1.87 (3H), 2.06 (1H), 2.20-2.64 (10H), 2.71 (1H), 3.77 (3H), 4.26 (2H), 4.43 (1H), 4.51 (2H), 5.78 (1H), 7.13 (2H), 7.36 (2H) ppm.

EXAMPLE 9a methyl[(3-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydro-spiro[cyclopenta[a]phenanthrene-3,2'-[1,3]dioxane]-11-yl]phenyl}prop-2-yn-1-yl)oxy]acetate

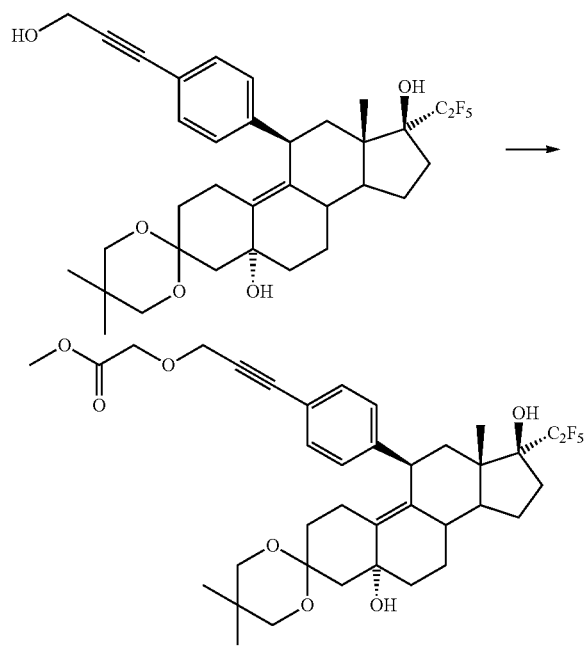

In analogy to Example 8, 50 mg (80 μmol) of the compound prepared according to Example 1a were converted and, after workup and purification, 32 mg (58%) of the title compound were isolated as a colourless foam.

EXAMPLE 10

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyloxy}acetic acid

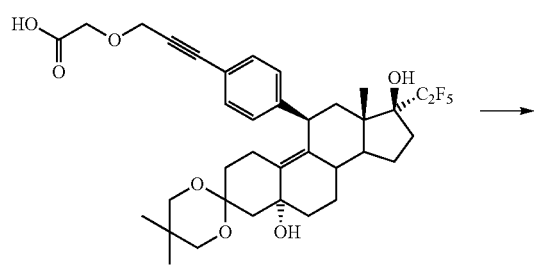

In analogy to Example 1, 25 mg (37 μmol) of the compound prepared according to Example 10a were converted and, after workup and purification, 3.2 mg (15%) of the title compound were isolated as a colourless foam.

¹H NMR (CDCl₃):=0.58 (3H), 1.69-1.56 (2H), 1.73-1.87 (3H), 2.01-2.11 (2H), 2.19-2.64 (9H), 2.71 (1H), 4.30 (2H), 4.44 (1H), 4.54 (2H), 5.80 (1H), 7.14 (2H), 7.36 (2H) ppm.

EXAMPLE 10a

[(3-{4-[(5R,8S,11R,13S,14S,17S)-5,17-dihydroxy-5',5',13-trimethyl-17-(pentafluoroethyl)-1,2,4,5,6,7,8,11,12,13,14,15,16,17-tetradecahydro-spiro[cyclopenta[a]phenanthrene-3,2'-[1,3]dioxane]-11-yl]phenyl}prop-2-yn-1-yl)oxy]acetic acid

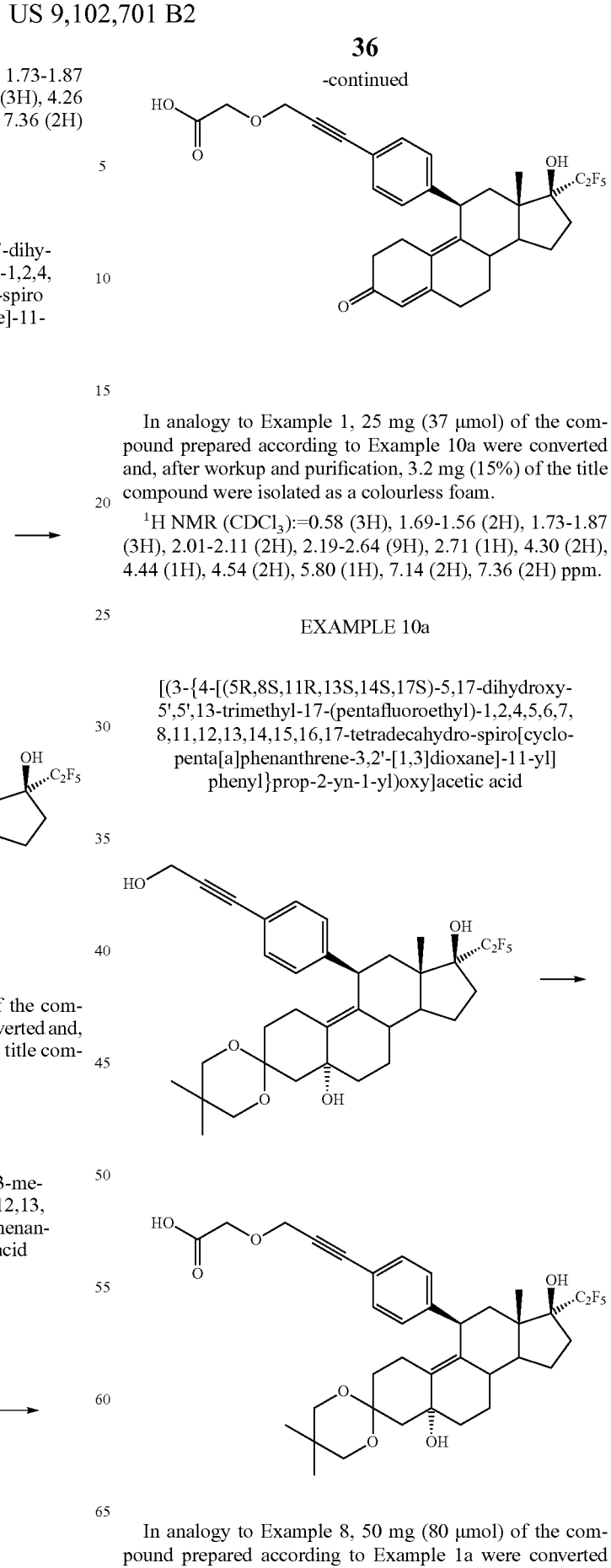

In analogy to Example 8, 50 mg (80 μmol) of the compound prepared according to Example 1a were converted using methyl bromoacetate and, after workup and purification, 45 mg (83%) of the title compound were isolated as a colourless foam.

EXAMPLE 11

(8S,11R,13S,14S,17S)-17-hydroxy-11-{4-[3-(2-hydroxyethoxy)prop-1-yn-1-yl]-phenyl}-13-methyl-17-pentafluoroethyl-1,2,6,7,8,11,12,13,14,15,16,17-dodecahydrocyclopenta[a]phenanthren-3-one

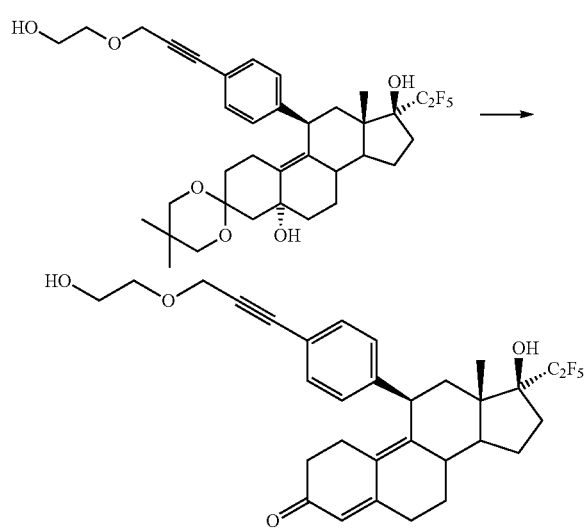

In analogy to Example 1, 15 mg (22 µmol) of the compound prepared according to Example 11a were converted and, after workup and purification, 8.4 mg (66%) of the title compound were isolated as a colourless oil.

$^1$H NMR (CDCl$_3$):=0.58 (3H), 1.40-1.54 (2H), 1.74-1.85 (3H), 1.93-2.12 (3H), 2.21-2.64 (9H), 2.72 (1H), 3.71 (2H), 3.80 (2H), 4.42 (2H), 4.44 (1H), 5.79 (1H), 7.13 (2H), 7.37 (2H) ppm.

EXAMPLE 11a (5R,8S,11R,13S,14S,17S)-11-{4-[3-(2-hydroxy-ethoxy)prop-1-yn-1-yl]phenyl}-5',5',13-trimethyl-17-(pentafluoroethyl)-1,2,3,4,6,7,8,11,12,13,14,15,16,17-tetradecahydro-spiro[cyclopenta[a]phenanthrene-3,2'-[1,3]dioxane]-5,17-diol

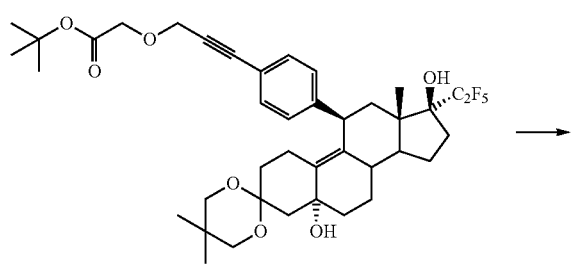

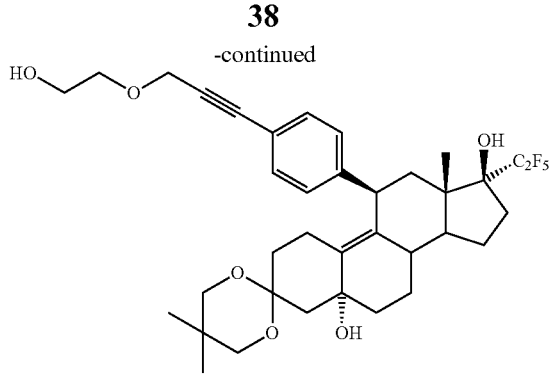

The solution of 97 mg (0.13 mmol) of the compound prepared according to Example 8a in 1.95 ml of toluene was admixed at −70° C. with 0.66 ml of a 1 molar solution of diisobutylaluminium hydride in toluene. After 1 hour, the mixture was poured into water, acidified by adding 1 molar hydrochloric acid and extracted repeatedly with ethyl acetate, and the combined organic extracts were washed with saturated sodium chloride solution and dried over sodium sulphate. The residue obtained after filtration and removal of solvent was purified by chromatography. 50 mg (56%) of the title compound were isolated as a colourless foam.

EXAMPLE 12

3-{(E/Z)-4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]but-1-en-3-ynyl}benzoic acid methyl ester

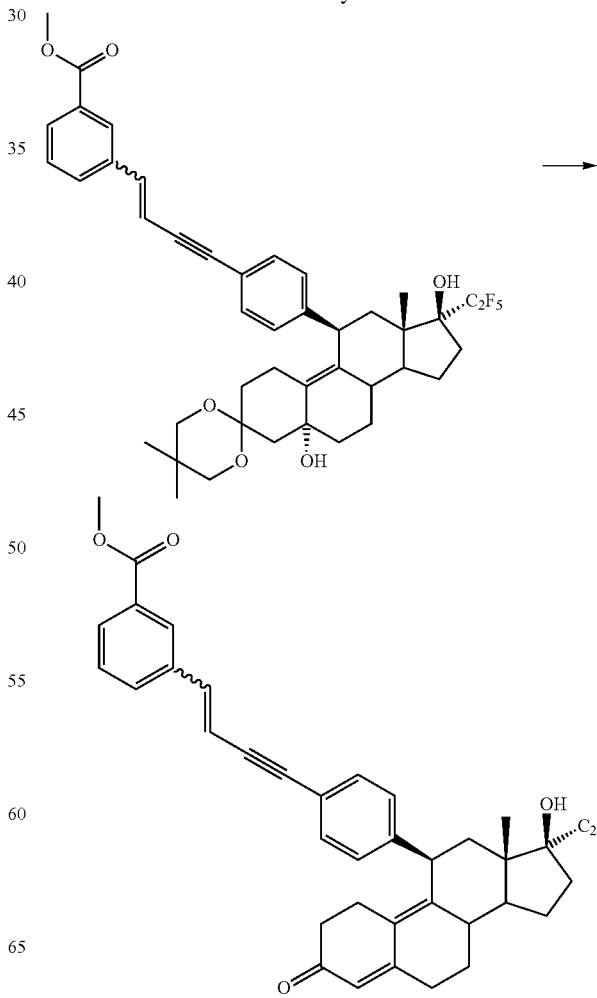

In analogy to Example 1, 83.3 mg (0.11 mmol) of a mixture of the compounds prepared according to Example 12a were converted and, after workup and purification, 46.8 mg (65%) of the title compounds were isolated as a pale yellow foam.

¹H NMR (CDCl₃):=0.61 (3H), 1.40-1.56 (2H), 1.73-1.88 (3H), 2.01-2.13 (2H), 2.22-2.65 (9H), 2.73 (1H), 3.92+3.93 (3H), 4.46 (1H), 5.79 (1H), 5.98+6.46 (1H), 6.72+7.05 (1H), 7.17 (2H), 7.36-8.05 (5H), 8.10+8.75 (1H) ppm.

EXAMPLE 12a

3-{(E/Z)-4-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxane]-11-yl)phenyl]but-1-en-3-ynyl}benzoic acid methyl ester

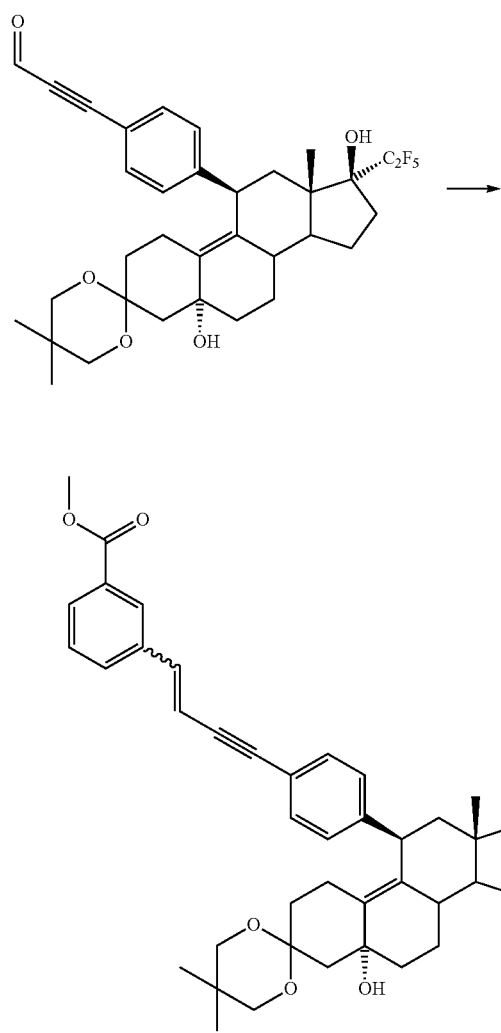

The solution of 406 mg 3-methoxycarbonyltriphenylphosphonium bromide in 2 ml of toluene was admixed at 3° C. with 1.4 ml of a 0.6 molar solution of sodium bis(trimethylsilyl)amide in toluene and the mixture was stirred at 23° C. for 60 minutes. Subsequently, the solution of 100 mg (0.16 mmol) of the compound prepared according to Example 2a in 2 ml of toluene was added dropwise and the mixture was left to react for 1 hour. The mixture was poured into water and extracted repeatedly with ethyl acetate, and the combined organic extracts were dried over sodium sulphate. The residue obtained after filtration and removal of solvent was purified by chromatography. 82 mg (67%) of the title compounds were isolated as a colourless foam.

EXAMPLE 13 (A+B)

(A) 3-{(E)-4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]but-1-en-3-ynyl}benzoic acid and (B) 3-{(Z)-4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]but-1-en-3-ynyl}benzoic acid

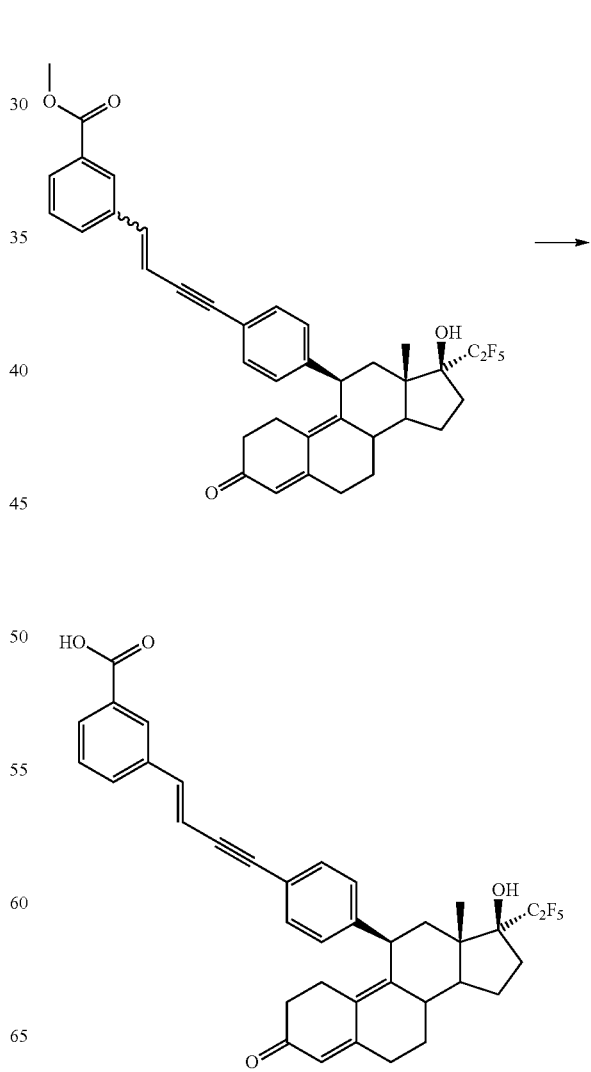

-continued

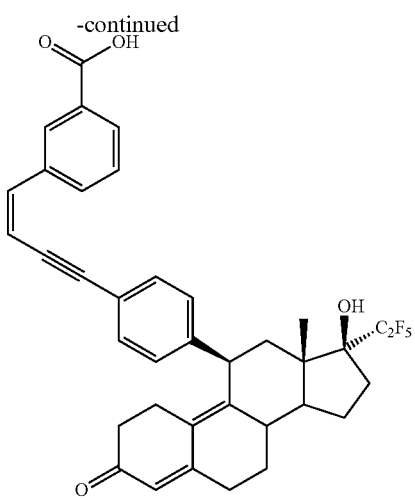

The solution of 42 mg (65 µmol) of the compound prepared according to Example 12 in 0.68 ml of tetrahydrofuran was admixed with 0.29 ml of a 5% aqueous lithium hydroxide solution and stirred at 23° C. for 16 hours. The mixture was acidified by adding 1 molar hydrochloric acid, saturated with sodium chloride and extracted repeatedly with diethyl ether, and the combined organic extracts were dried over sodium sulphate. The residue obtained after filtration and removal of solvent was purified by chromatography. 8.1 mg (20%) of each of the title compounds were isolated as a colourless foam.

$^1$H NMR (CDCl$_3$) of A:=0.60 (3H), 1.42-1.54 (2H), 1.74-1.86 (3H), 2.07 (1H), 2.24-2.65 (10H), 2.74 (1H), 4.45 (1H), 5.81 (1H), 6.47 (1H), 7.06 (1H), 7.16 (2H), 7.40 (2H), 7.46 (1H), 7.65 (1H), 8.03 (1H), 8.16 (1H) ppm.

$^1$H NMR (CDCl$_3$) of B:=0.51 (3H), 1.38-1.54 (2H), 1.72-1.86 (3H), 1.97-2.08 (2H), 2.16-2.63 (10H), 2.69 (1H), 4.43 (1H), 5.74 (1H), 6.01 (1H), 6.74 (1H), 7.15 (2H), 7.50 (1H), 7.54 (2H), 7.86 (1H), 8.05 (1H), 9.14 (1H) ppm.

EXAMPLE 14

{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyloxy}acetonitrile

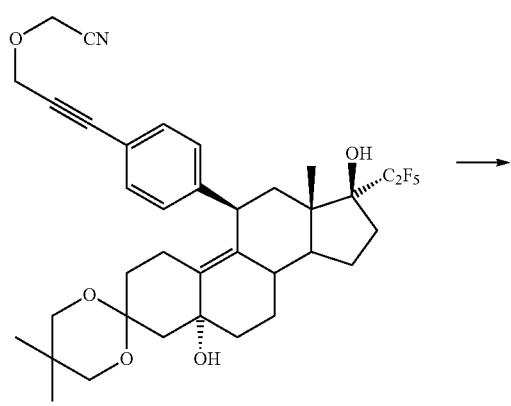

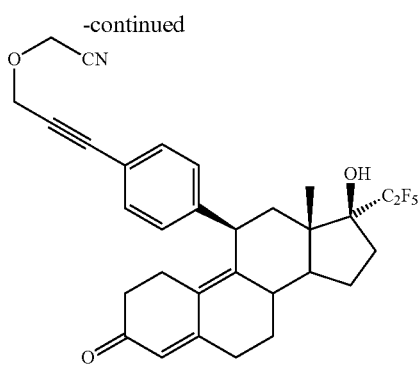

In analogy to Example 1, 104 mg (160 µmol) of the compound prepared according to Example 14a were converted and, after workup and purification, 81 mg (93%) of the title compound were isolated as a colourless foam.

$^1$H NMR (CDCl$_3$):=0.58 (3H), 1.38-1.56 (2H), 1.71-1.88 (3H), 2.05 (1H), 2.07 (1H), 2.18-2.65 (9H), 2.72 (1H), 4.43 (3H), 4.54 (2H), 5.79 (1H), 7.16 (2H), 7.39 (2H) ppm.

EXAMPLE 14a

{3-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxane]-11-yl)phenyl]prop-2-ynyloxy}acetonitrile

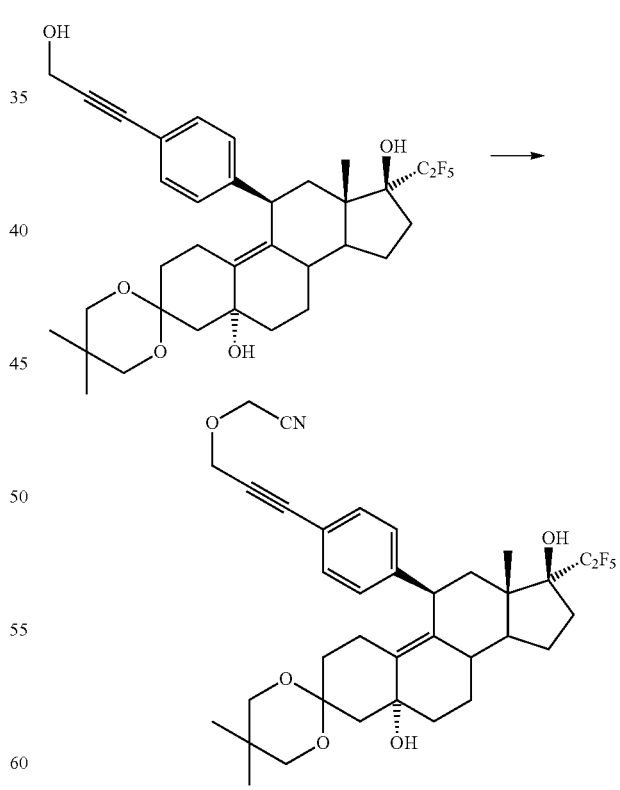

In analogy to Example 8, 250 mg (0.40 mmol) of the compound prepared according to Example 1a were converted using bromoacetonitrile and, after workup and purification, 186 mg (70%) of the title compound were isolated as a colourless foam.

EXAMPLE 15

4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid methyl ester

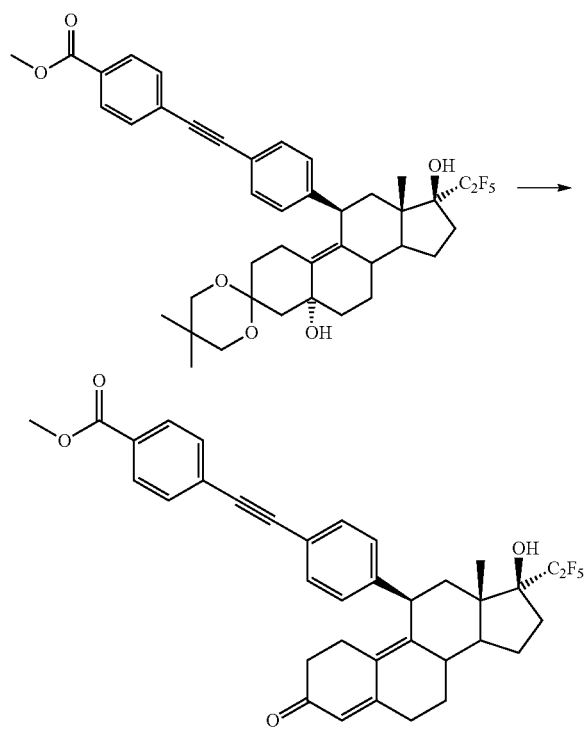

In analogy to Example 1, 14 mg (19 µmol) of the compound prepared according to Example 15a were converted and, after workup and purification, 7.7 mg (63%) of the title compound were isolated as a colourless foam.

$^1$H NMR (CDCl$_3$):=0.61 (3H), 1.38-1.57 (2H), 1.73-1.90 (3H), 2.08 (1H), 2.14 (1H), 2.20-2.68 (9H), 2.74 (1H), 3.92 (3H), 4.47 (1H), 5.80 (1H), 7.19 (2H), 7.46 (2H), 7.57 (2H), 8.01 (2H) ppm.

EXAMPLE 15a

4-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxane]-11-yl)phenylethynyl]benzoic acid methyl ester

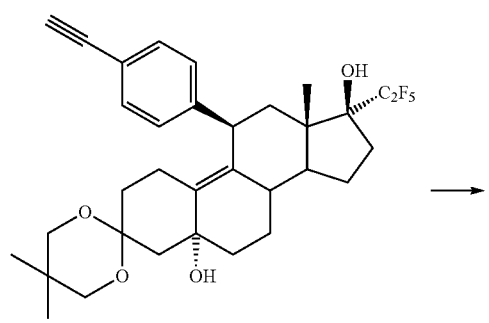

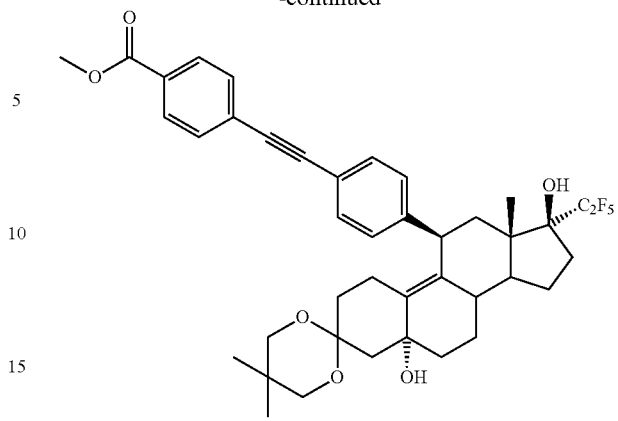

The solution of 50 mg (84 µmol) of the compound prepared according to Example 15b in 8 ml of tetrahydrofuran was admixed with 14.4 mg of methyl 4-chlorobenzoate, 3.4 ml of triethylamine, tetrakis(triphenylphosphine)palladium(0), 1.3 mg of copper(I) iodide, 2.4 mg and the mixture was stirred at 23° C. for 3 hours. The mixture was concentrated and the residue was purified by chromatography. 25 mg (41%) of the title compound were isolated as a colourless foam.

EXAMPLE 15b (5R,8S,11R,13S,14S,17S)-11-(4-ethynylphenyl)-5',5',13-trimethyl-17-pentafluoroethyl-1,2,3,4,6,7,8,11,12,13,14,15,16,17-tetradecahydro-1H-spiro[cyclopenta[a]phenanthrene-3,2'-[1,3]dioxane]-5,17-diol

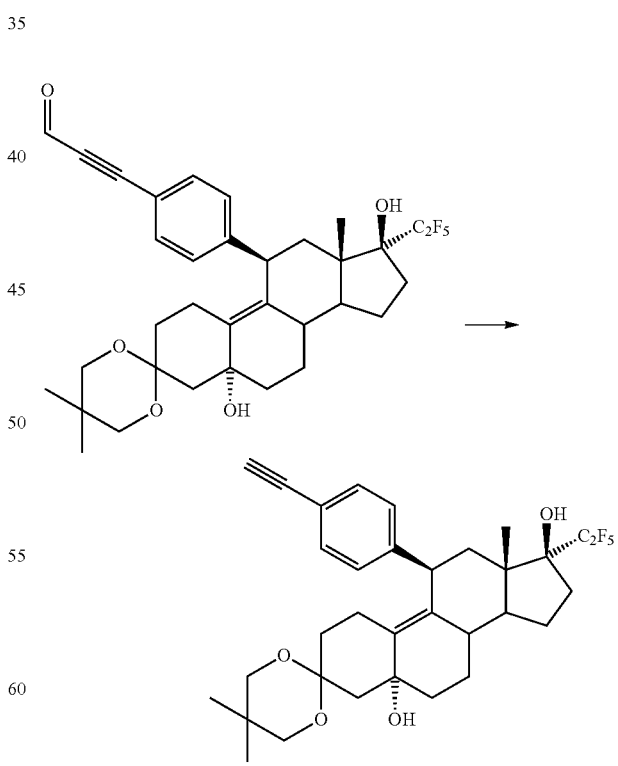

The solution of 1.64 g (2.63 mmol) of the compound prepared according to Example 2a in 30 ml of tetrahydrofuran was admixed with 2 ml of a 50% potassium hydroxide solution and stirred at 60° C. for 2 hours. It was diluted with water, acidified by addition of 1 molar hydrochloric acid and extracted repeatedly with ethyl acetate. The combined organic extracts were washed with saturated sodium hydrogencarbonate solution and saturated sodium chloride solution, and dried over sodium sulphate. The residue obtained after filtration and removal of solvent was purified by chromatography. 1.34 g (86%) of the title compound were isolated as a colourless foam.

EXAMPLE 16

4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid

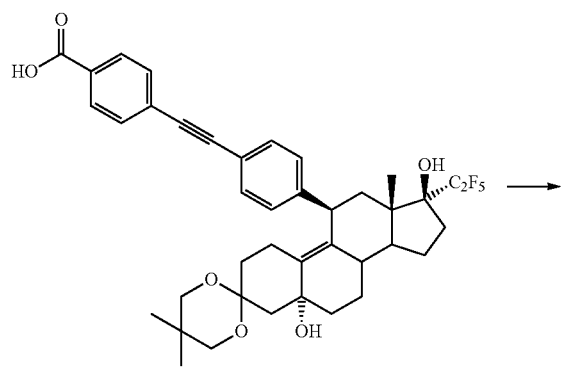

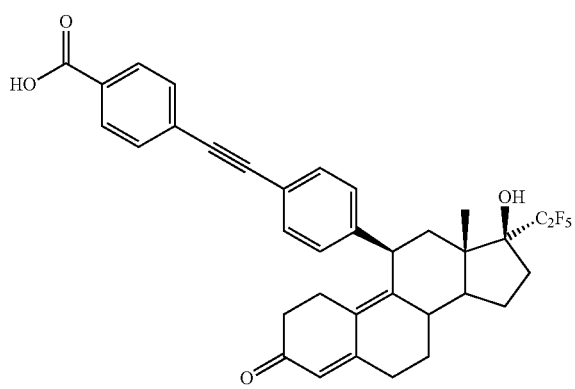

In analogy to Example 1, 28 mg (38 μmol) of the compound prepared according to Example 16a were converted and, after workup and purification, 17 mg (74%) of the title compound were isolated as a colourless foam.

$^1$H NMR (CD$_3$OD):=0.60 (3H), 1.37-1.56 (2H), 1.71-1.84 (3H), 2.10 (1H), 2.20-2.48 (5H), 2.56-2.73 (4H), 2.82 (1H), 4.55 (1H), 5.74 (1H), 7.27 (2H), 7.45 (2H), 7.47 (2H), 7.91 (2H) ppm.

EXAMPLE 16a

4-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxane]-11-yl)phenylethynyl]benzoic acid

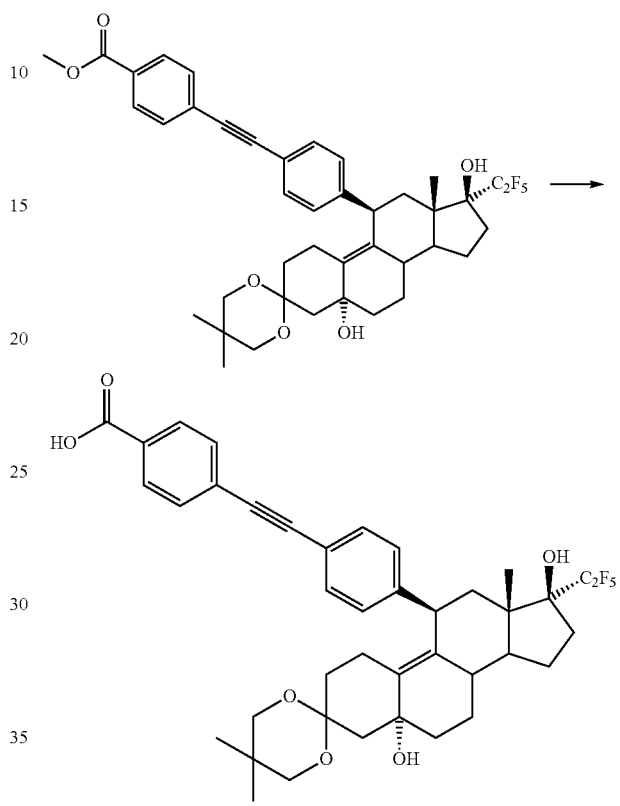

In analogy to Example 13, 28 mg (38 μmol) of the compound prepared according to Example 15a were converted and, after workup and purification, 26 mg (95%) of the title compound were isolated as a colourless foam.

EXAMPLE 17

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid methyl ester

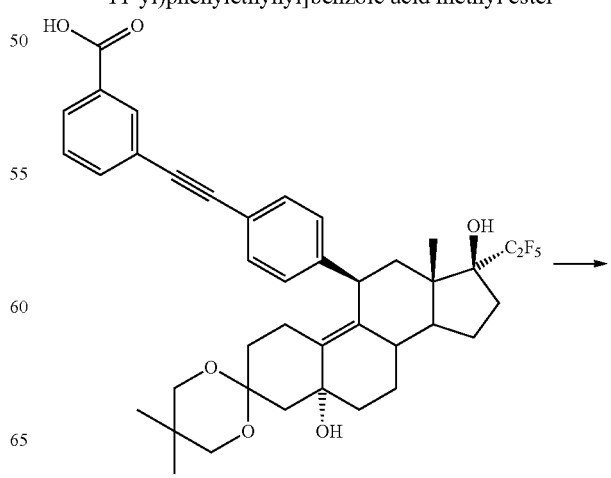

-continued

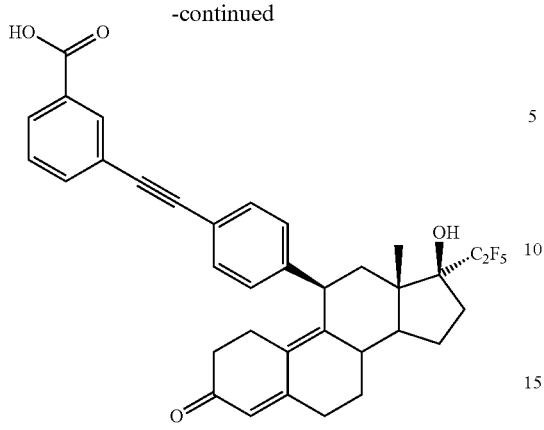

In analogy to Example 1, 459 mg (690 µmol) of the compound prepared according to Example 17a are converted and, after workup and purification, 307 mg (73%) of the title compound are isolated as a colourless foam.

$^1$H NMR (CD$_3$OD):=0.60 (3H), 1.35-1.59 (2H), 1.70-1.84 (3H), 2.10 (1H), 2.18-2.49 (5H), 2.55-2.75 (4H), 2.82 (1H), 4.55 (1H), 5.74 (1H), 7.26 (2H), 7.36-7.49 (3H), 7.59 (1H), 7.93 (1H), 8.07 (1H) ppm.

EXAMPLE 17a

3-[4-((5R,8S,11R,13S,14S,17S)-5,17-dihydroxy-5, 5',13-trimethyl-17-pentafluoroethyl-2,3,4,5,6,7,8,11, 12,13,14,15,16,17-tetradecahydro-1H-spiro[cyclopenta[a]phenanthrene-3,2'-[1,3]dioxane]-11-yl) phenylethynyl]benzoic acid

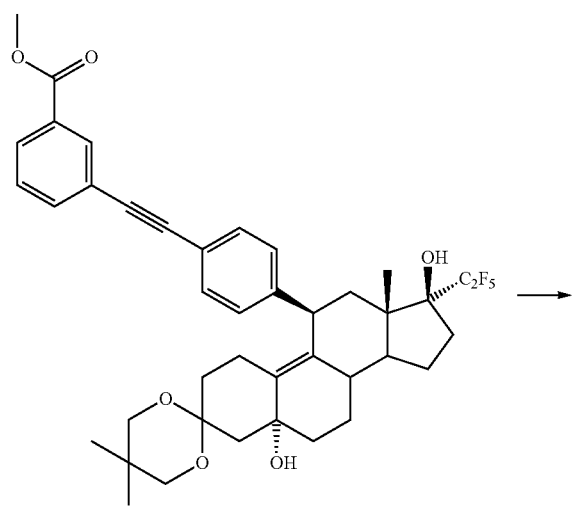

-continued

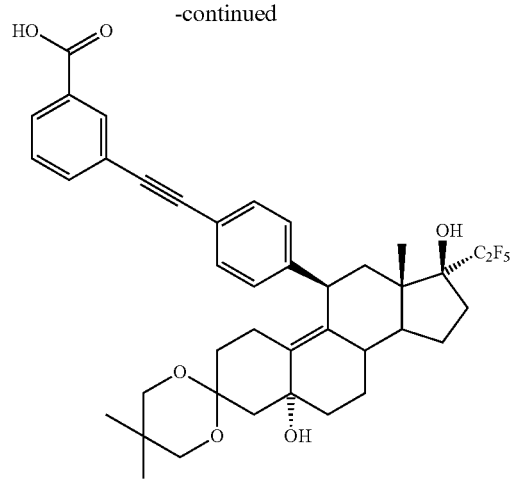

In analogy to Example 13, 19 mg (26 µmol) of the compound prepared according to Example 17b were converted and, after workup and purification, 18 mg (97%) of the title compound were isolated as a colourless foam.

EXAMPLE 17b

3-[4-((5R,8S,11R,13S,14S,17S)-5,17-dihydroxy-5', 5',13-trimethyl-17-pentafluoroethyl-2,3,4,5,6,7,8,11, 12,13,14,15,16,17-tetradecahydro-1H-spiro[cyclopenta[a]phenanthrene-3,2'-[1,3]dioxane]-11-yl) phenylethynyl]benzoic acid methyl ester

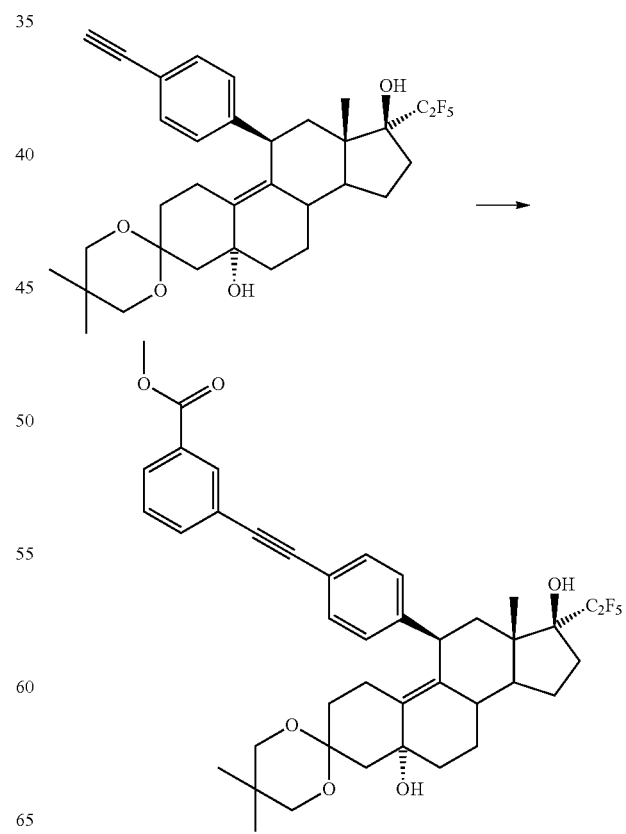

The mixture of 2.3 mg of bis(acetonitrile)palladium(II) chloride, 6 mg of 2-dicyclohexylphosphino-2',4',6'-triisopropylphenyl and 82.5 mg of caesium carbonate in 0.75 ml of acetonitrile was admixed at 23° C. with 17 µl of methyl 3-chlorobenzoate and, after 30 minutes, with the solution of 75 mg (0.13 mmol) of the compound prepared according to Example 15b in 0.75 ml of acetonitrile. The mixture was left to react at 70° C. for 2 hours, water was added and the mixture was extracted repeatedly with ethyl acetate. The combined organic extracts were dried over sodium sulphate, and the residue obtained after filtration and removal of solvent was purified by chromatography. 19 mg (21%) of the title compound were isolated as a colourless foam.

EXAMPLE 18

(8S,11R,13S,14S,17S)-17-hydroxy-13-methyl-17-pentafluoroethyl-11-{4-[3-(1H-tetrazol-5-yl-methoxy)prop-1-yn-1-yl]phenyl}-1,2,6,7,8,11,12,13,14,15,16,17-dodecahydrocyclopenta[a]phenanthren-3-one

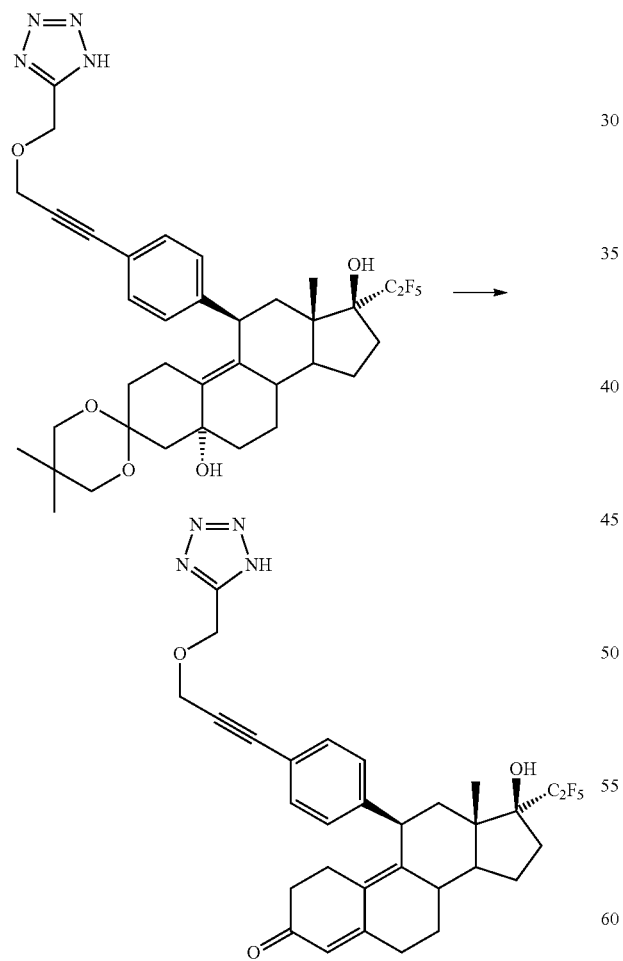

In analogy to Example 1, 426 mg (200 µmol) of the compound prepared according to Example 18a were converted and, after workup and purification, 44 mg (37%) of the title compound were isolated as a colourless foam.

$^1$H NMR (CD$_3$OD):=0.57 (3H), 1.36-1.56 (2H), 1.69-1.83 (3H), 2.09 (1H), 2.16-2.47 (5H), 2.54-2.72 (4H), 2.80 (1H), 4.50-4.56 (3H), 4.99 (2H), 5.74 (1H), 7.22 (2H), 7.33 (2H) ppm.

EXAMPLE 18a (5R,8S,11R,13S,14S,17S)-5',5',13-trimethyl-17-pentafluoroethyl-11-{4-[3-(1H-tetrazol-5-ylmethoxy)prop-1-ynyl]phenyl}-1,2,3,4,6,7,8,11,12,13,14,15,16,17-tetradecahydro-1H-spiro[cyclopenta[a]phenanthrene-3,2'-[1,3]dioxane]-5,17-diol

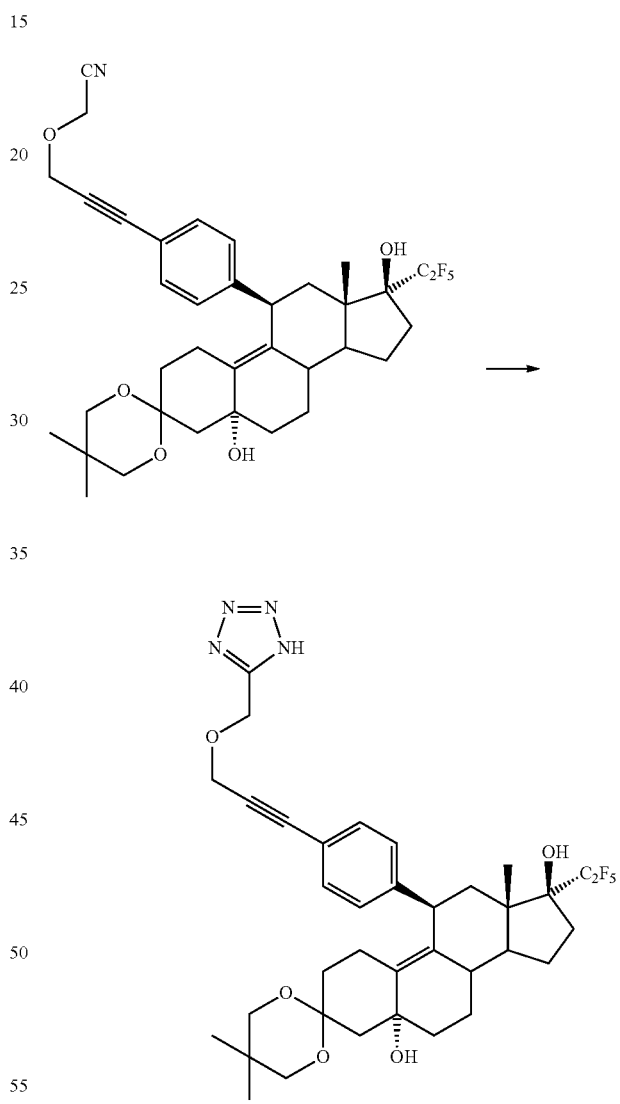

The solution of 20 mg (30 µmol) of the compound prepared according to Example 14a in 0.4 ml of dimethylformamide was admixed with 10 mg of sodium azide, 1 mg of ammonium chloride, and heated to 120° C. for 16 hours. The mixture was poured into water and extracted repeatedly with ethyl acetate, and the combined organic extracts were washed with water and saturated sodium chloride solution and dried over sodium sulphate. The residue obtained after filtration and removal of solvent was purified by chromatography. 11.5 mg (54%) of the title compound were isolated as a colourless foam.

EXAMPLE 19

4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid

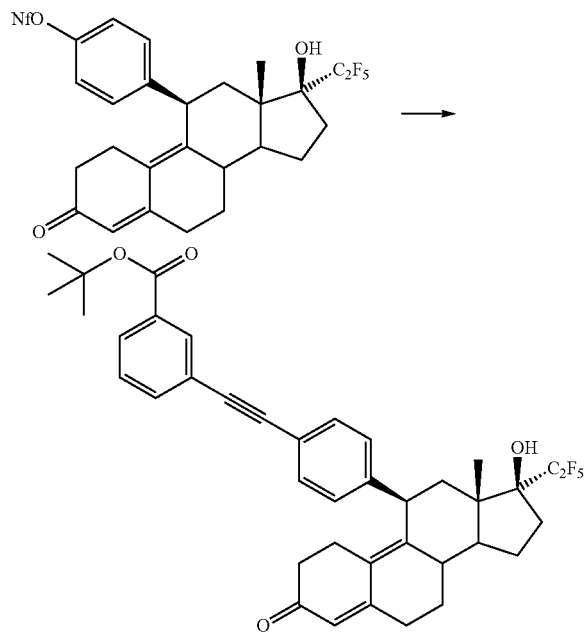

The solution of 1 g (1.31 mmol) of the compound prepared according to Example 19a in 7 ml of acetonitrile was admixed with 350 mg of tert-butyl 4-ethynylbenzoate, 364 µl of triethylamine, 11 mg of palladium dichloride, 34 mg of triphenylphosphine, 6 mg of copper(I) iodide, and the mixture was heated to 80° C. for 2 hours. The mixture was poured into a saturated ammonium chloride solution and extracted repeatedly with ethyl acetate, and the combined organic extracts were washed with saturated sodium chloride solution and dried over sodium sulphate. The residue obtained after filtration and removal of solvent was purified by chromatography. 318 mg (36%) of the title compound were isolated as a colourless foam.

$^1$H NMR (CDCl$_3$):=0.60 (3H), 1.36-1.55 (2H), 1.60 (9H), 1.74-1.87 (3H), 2.01-2.14 (2H), 2.22-2.66 (9H), 2.74 (1H), 4.46 (1H), 5.80 (1H), 7.18 (2H), 7.47 (2H), 7.55 (2H), 7.96 (2H) ppm.

EXAMPLE 19a 1,1,2,2,3,3,4,4,4-nonafluorobutane-1-sulphonic acid 4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl ester

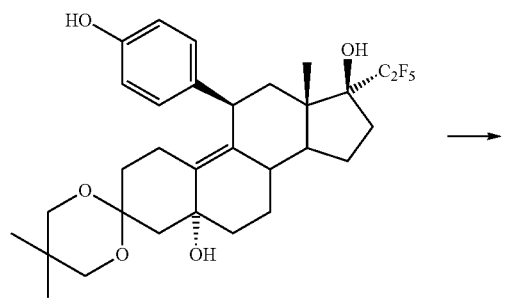

-continued

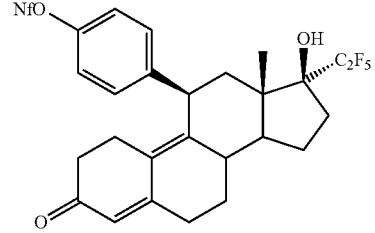

The solution of 17.1 g (27.2 mmol) of (5R,8S,11R,13S,14S,17S)-11-(4-hydroxyphenyl)-5',5',13-trimethyl-17-pentafluoroethyl-2,3,4,6,7,8,11,12,13,14,15,16,17-tetradecahydro-1H-spiro[cyclopenta[a]phenanthrene-3,2'-[1,3]dioxane]-5,17-diol in 380 ml of tetrahydrofuran is cooled to −3° C., and admixed with 25.5 ml of a 1.6 molar solution of butyllithium in hexane and, after 30 minutes, with 9.78 ml of nonafluorobutanesulphonyl fluoride. The mixture was stirred at 0° C. for 1.5 hours, poured onto saturated sodium hydrogencarbonate solution and extracted repeatedly with ethyl acetate, and the combined organic extracts were washed with water and saturated sodium chloride solution and dried over sodium sulphate. The residue obtained after filtration and removal of solvent was purified by crystallization. 18.6 g (89%) of the title compound were isolated as a colourless solid.

EXAMPLE 20

3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid

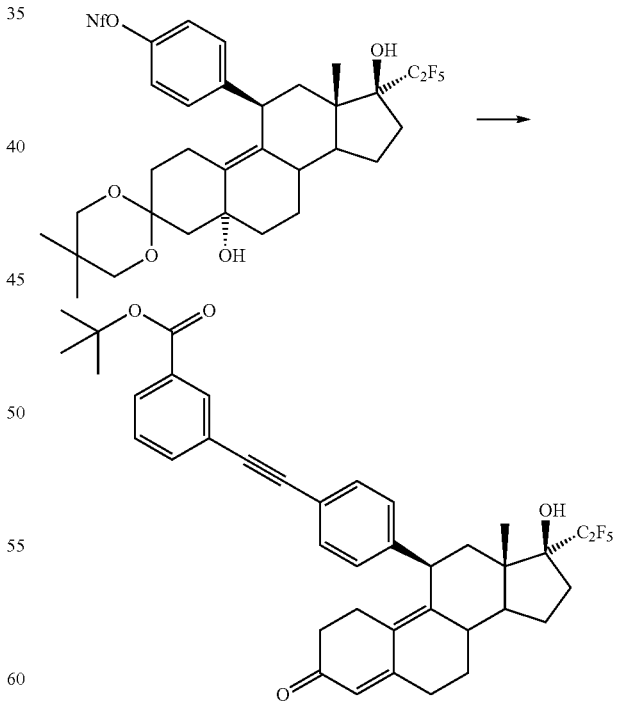

In analogy to Example 19, 2 g (2.62 mmol) of the compound prepared according to Example 19a were converted using tert-butyl 3-ethynylbenzoate and, after workup and purification, 478 mg (27%) of the title compound were isolated as a colourless foam.

¹H NMR (CDCl₃):=0.61 (3H), 1.40-1.65 (2H), 1.60 (9H), 1.74-1.88 (3H), 2.02-2.13 (2H), 2.22-2.67 (9H), 2.74 (1H), 4.47 (1H), 5.80 (1H), 7.18 (2H), 7.40 (1H), 7.46 (2H), 7.66 (1H), 7.94 (1H), 8.12 (1H) ppm.

EXAMPLE 21

(8S,11R,13S,14S,17S)-17-hydroxy-11-[4-(3-hydroxy-3-methylbut-1-ynyl)phenyl]-13-methyl-17-pentafluoroethyl-1,2,6,7,8,11,12,13,14,15,16,17-dodecahydrocyclopenta[a]phenanthren-3-one

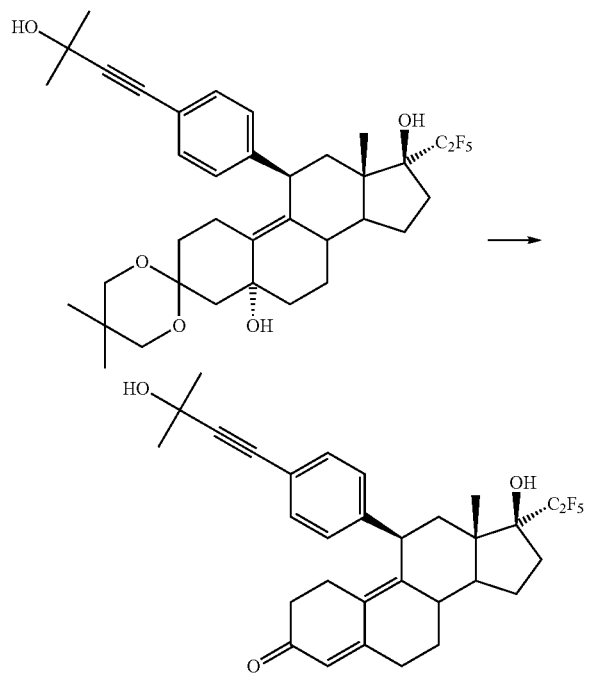

In analogy to Example 1, 103 mg (160 μmol) of the compound prepared according to Example 21a were converted and, after workup and purification, 57 mg (66%) of the title compound were isolated as a colourless foam.

¹H NMR (CDCl₃):=0.57 (3H), 1.38-1.56 (2H), 1.61 (6H), 1.72-1.86 (3H), 2.03 (1H), 2.06 (1H), 2.08 (1H), 2.19-2.65 (9H), 2.71 (1H), 4.43 (1H), 5.79 (1H), 7.11 (2H), 7.34 (2H) ppm.

EXAMPLE 21a (5R,8S,11R,13S,14S,17S)-11-[4-(3-hydroxy-3-methylbut-1-ynyl)phenyl]-5',5',13-trimethyl-17-pentafluoroethyl-2,3,4,6,7,8,11,12,13,14,15,16,17-tetradecahydro-1H-spiro[cyclopenta[a]phenanthrene-3,2'-[1,3]dioxane-5,17-diol

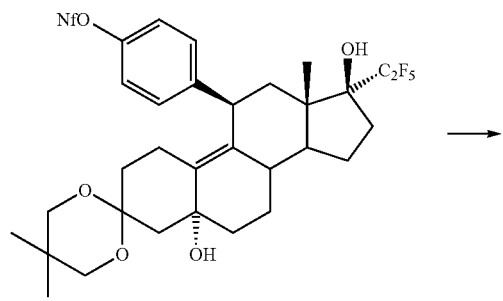

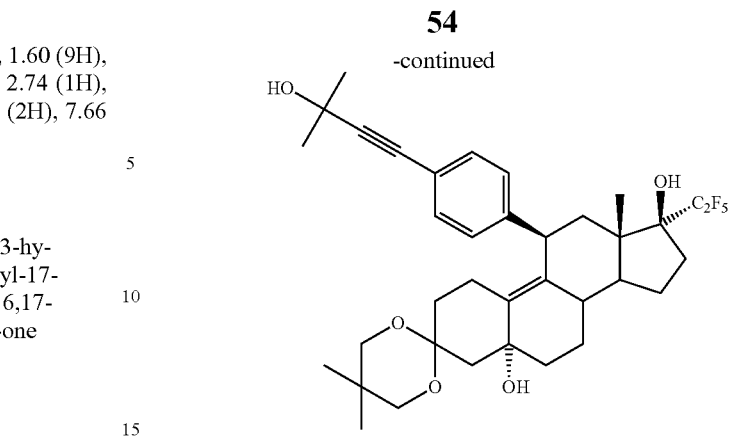

In analogy to Example 1a, 500 mg (0.58 mmol) of 1,1,2,2,3,3,4,4,4-nonafluorobutane-1-sulphonic acid 4-((5R,8S,11R,13S,14S,17S)-5,17-dihydroxy-17-pentafluoroethyl-5',5',13-trimethyl-2,3,4,6,7,8,11,12,13,14,15,16,17-tetradecahydro-1H-spiro[cyclopenta[a]phenanthrene-3,2'-[1,3]dioxan-11-yl)phenyl ester were converted using 2-methylbut-3-yn-2-ol and, after workup and purification, 103 mg (27%) of the title compound were isolated as a colourless foam.

EXAMPLE 22

(8S,11R,13S,14S,17S)-1'-(4-ethynylphenyl)-17-hydroxy-13-methyl-17-pentafluoroethyl-1,2,6,7,8,11,12,13,14,15,16,17-dodecahydrocyclopenta[a]phenanthren-3-one

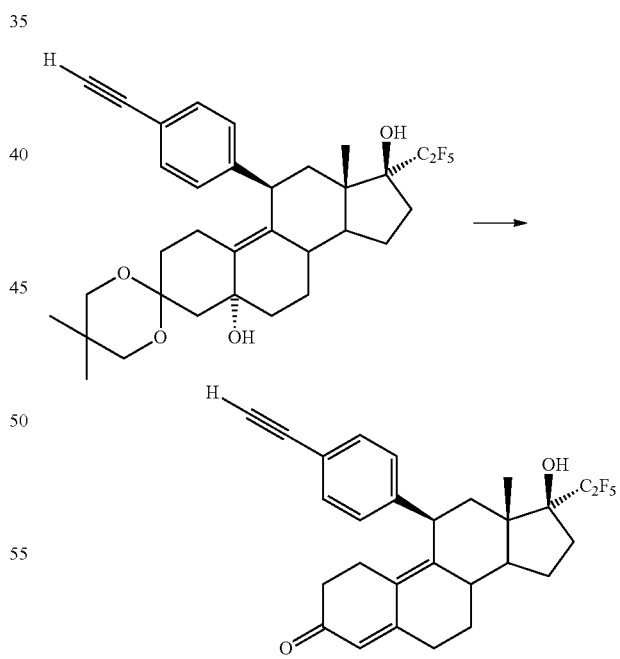

In analogy to Example 1, 13 mg (22 μmol) of the compound prepared according to Example 22a were converted and, after workup and purification, 8 mg (74%) of the title compound were isolated as a colourless foam.

¹H NMR (CDCl₃):=0.58 (3H), 1.41-1.55 (2H), 1.74-1.86 (3H), 2.07 (1H), 2.11 (1H). 2.21-2.64 (9H), 2.72 (1H), 3.06 (1H), 4.44 (1H), 5.79 (1H), 7.14 (2H), 7.41 (2H) ppm.

EXAMPLE 22a (5R,8S,11R,13S,14S,17S)-11-[4-ethynylphenyl]-5',5',13-trimethyl-17-pentafluoroethyl-2,3,4,6,7,8,11,12,13,14,15,16,17-tetradecahydro-1H-spiro[cyclopenta[a]phenanthrene-3,2'-[1,3]dioxane-5,17-diol

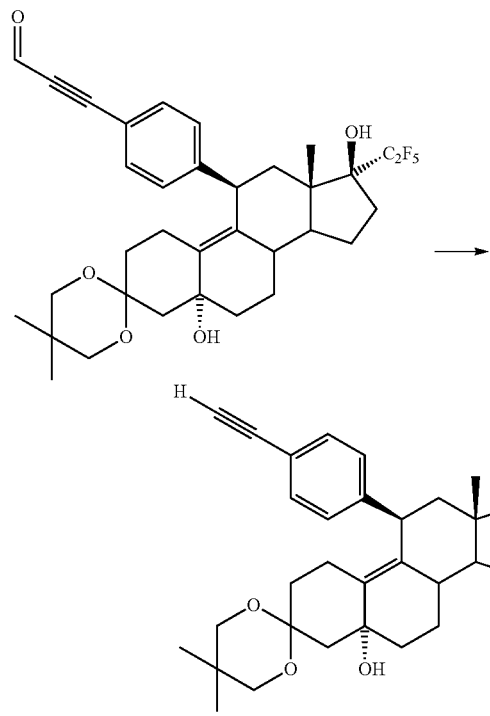

The solution of 1.64 g (2.63 mmol) of the compound prepared according to Example 2a in 30 ml of tetrahydrofuran was admixed with 2 ml of a 50% aqueous potassium hydroxide solution and stirred at 60° C. for 2 hours. The mixture was acidified by adding 1 molar hydrochloric acid and extracted repeatedly with ethyl acetate, and the combined organic extracts were washed with saturated sodium hydrogencarbonate and sodium chloride solution and dried over sodium sulphate. The residue obtained after filtration and removal of solvent was purified by chromatography. 1.34 g (86%) of the title compound were isolated as a colourless foam.

EXAMPLE 23

(8S,11R,13S,14S,17S)-11-[4-(3-azidoprop-1-yn-1-yl)phenyl]-17-hydroxy-13-methyl-17-pentafluoroethyl-1,2,6,7,8,11,12,13,14,15,16,17-dodecahydrocyclopenta[a]phenanthren-3-one

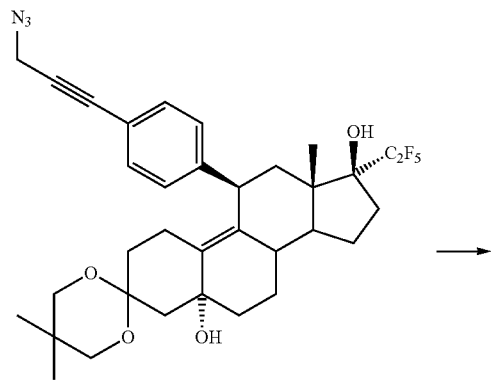

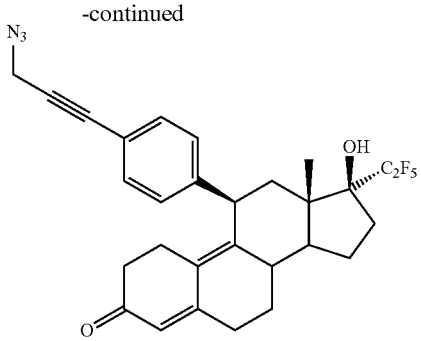

In analogy to Example 1, 21.7 mg (33 μmol) of the compound prepared according to Example 23a were converted and, after workup and purification, 14.5 mg (80%) of the title compound were isolated as a colourless foam.

$^1$H NMR (CDCl$_3$):=0.59 (3H), 1.38-1.56 (2H), 1.71-1.88 (3H), 2.07 (1H), 2.17-2.64 (10H), 2.72 (1H), 4.14 (2H), 4.44 (1H), 5.79 (1H), 7.15 (2H), 7.39 (2H) ppm.

EXAMPLE 23a (5R,8S,11R,13S,14S,17S)-11-[4-(3-azidoprop-1-yn-1-yl)phenyl]-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxane]-5,17-diol

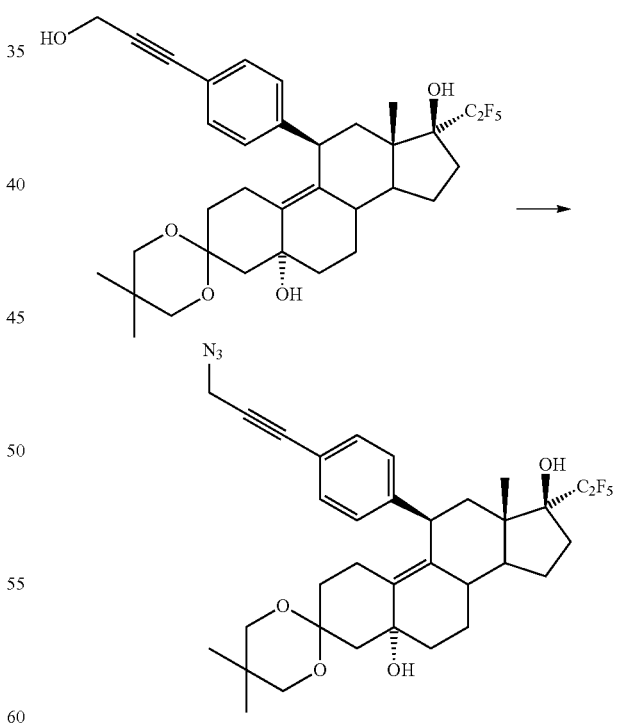

The solution of 150 mg (0.24 mmol) of the compound prepared according to Example 1a in 3.6 ml of tetrahydrofuran was admixed at 3° C. with 0.1 ml of diphenylphosphoryl azide, 42 μl of 1,8-diazabicyclo[5.4.0]undec-7-ene, and the mixture was left to react at 23° C. for 2 hours. Water was added to the mixture, which was extracted repeatedly with ethyl acetate, and the combined organic extracts were washed with saturated sodium chloride solution and dried over sodium sulphate. The residue obtained after filtration and removal of solvent was purified by chromatography. 114 g (73%) of the title compound were isolated as a colourless foam.

EXAMPLE 24 (A+B)

(A) (E)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]propynal O-benzyl oxime
and (B) (Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]propynal O-benzyl oxime

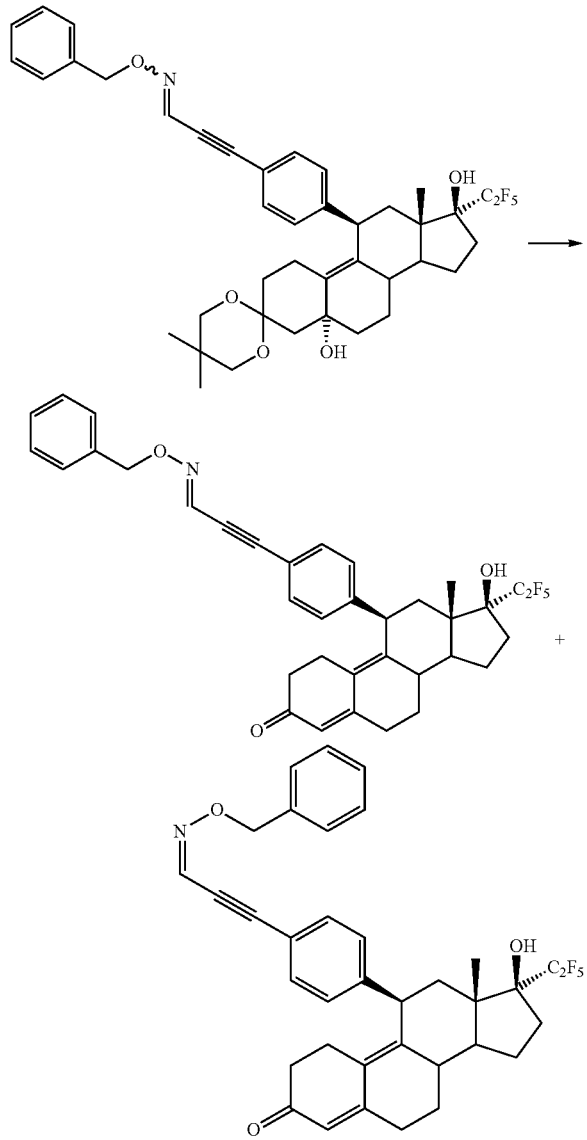

The solution of 52 mg (71 mmol) of the compounds prepared according to Example 24a in 1.2 ml of acetone was admixed with 0.11 ml of 4N hydrochloric acid and the mixture was stirred at 23° C. for 20 minutes. 59 µl of triethylamine were added, the mixture was concentrated and the residue obtained after filtration and removal of solvent was purified by chromatography. 14 mg (31%) of title compound A and 14.5 mg (33%) of title compound B were isolated, each as a colourless foam.

$^1$H NMR (CDCl$_3$) of A:=0.57 (3H), 1.38-1.56 (2H), 1.70-1.88 (3H), 2.08 (1H), 2.12 (1H), 2.19-2.65 (9H), 2.71 (1H), 4.44 (1H), 5.20 (2H), 5.79 (1H), 7.16 (2H), 7.30-7.47 (7H), 7.60 (1H) ppm.

$^1$H NMR (CDCl$_3$) of B:=0.57 (3H), 1.38-1.57 (2H), 1.72-1.88 (3H), 2.07 (1H), 2.17-2.64 (10H), 2.71 (1H), 4.44 (1H), 5.26 (2H), 5.79 (1H), 6.93 (1H), 7.17 (2H), 7.28-7.48 (7H) ppm.

EXAMPLE 24a (E/Z)-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxane]-11-yl)phenyl]propynal O-benzyl oxime

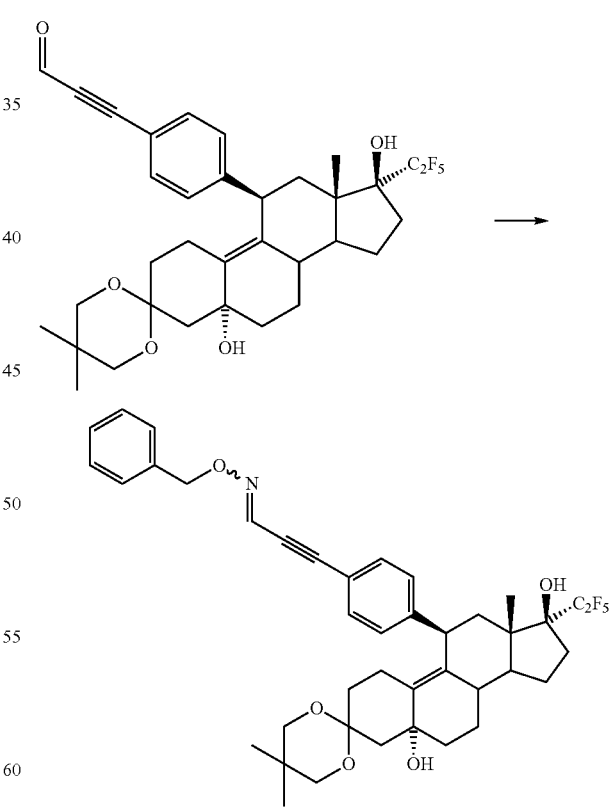

The solution of 10.8 mg of O-benzylhydroxylamine in 1 ml of ethanol was admixed with 50 mg (80 µmol) of the compound prepared according to Example 2a, the mixture was stirred at 23° C. for 2 hours and concentrated, and the residue was purified by chromatography. 52 mg (89%) of the title compounds were isolated as a colourless foam.

EXAMPLE 25 (A+B)

(A) (E)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]propynal O-ethyl oxime and (B) (Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]propynal O-ethyl oxime In analogy to Example 24, 47 mg (71 μmol) of the compounds prepared according to Example 25a were converted and, after workup and purification, 9 mg (23%) of title compound A and 12 mg (30%) of title compound B were isolated, each as a colourless foam.

$^1$H NMR (CDCl$_3$) of A:=0.57 (3H), 1.30 (3H), 1.39-1.56 (2H), 1.71-1.87 (3H), 2.08 (1H), 2.12 (1H), 2.19-2.65 (9H), 2.72 (1H), 4.22 (2H), 4.44 (1H), 5.79 (1H), 7.16 (2H), 7.43 (2H), 7.53 (1H) ppm.

$^1$H NMR (CDCl$_3$) of B:=0.57 (3H), 1.34 (3H), 1.39-1.57 (2H), 1.71-1.87 (3H), 2.07 (1H), 2.17 (1H), 2.19-2.65 (9H), 2.72 (1H), 4.27 (2H), 4.44 (1H), 5.79 (1H), 6.89 (1H), 7.17 (2H), 7.44 (2H) ppm.

EXAMPLE 25a (E/Z)-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxane]-11-yl)phenyl]propynal O-ethyl oxime

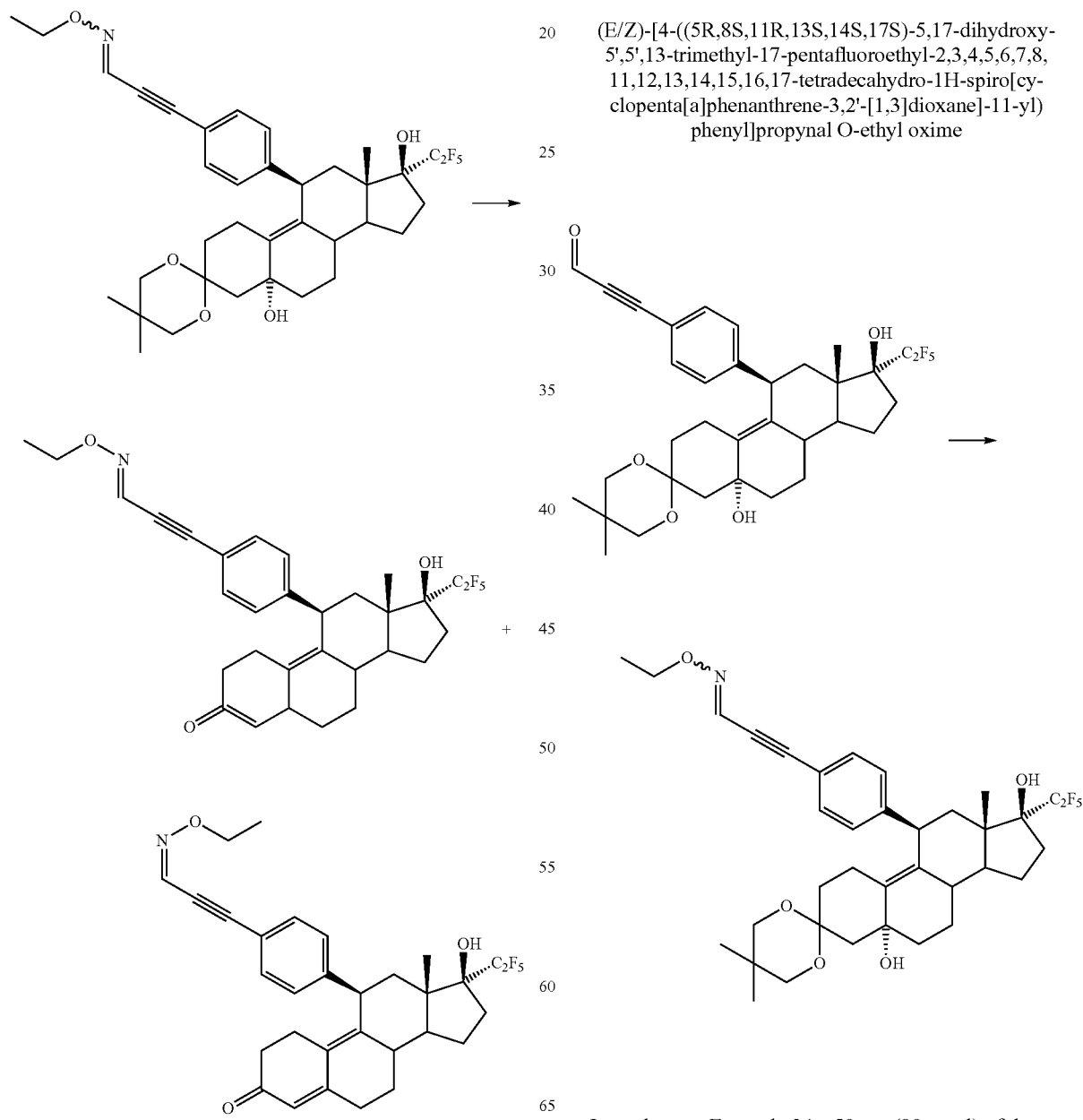

In analogy to Example 24a, 50 mg (80 μmol) of the compound prepared according to Example 2a were converted using O-ethylhydroxylamine and, after workup and purification, 47 mg (88%) of the title compounds were isolated as a colourless foam.

EXAMPLE 26

(E/Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]propynal O-isobutyl oxime $^1$H NMR (CDCl$_3$):=0.57 (3H), 0.93 (6H), 1.39-1.56 (2H), 1.71-1.88 (3H), 1.95-2.11 (2H), 2.13 (1H), 2.20-2.66 (9H), 2.72 (1H), 3.93 (2H), 4.44 (1H), 5.79 (1H), 7.16 (2H), 7.42 (2H), 7.55+6.86 (1H) ppm.

EXAMPLE 26a (E/Z)-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxane]-11-yl)phenyl]propynal O-isobutyl oxime

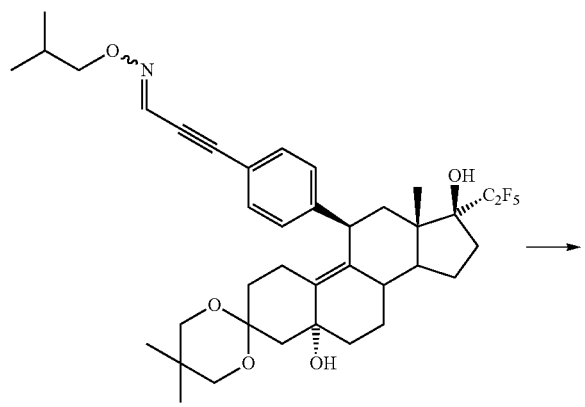

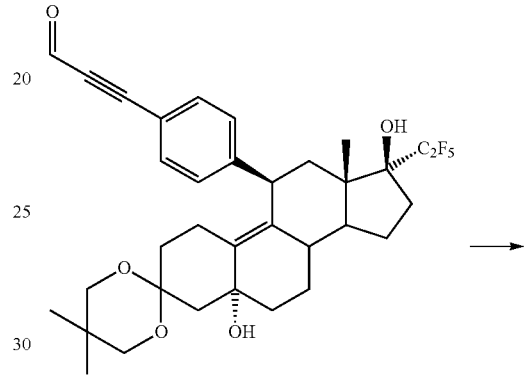

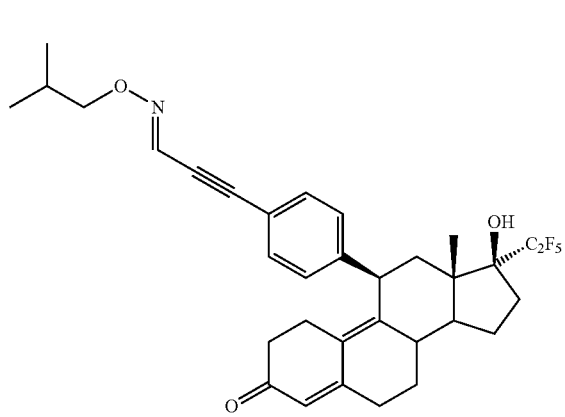

In analogy to Example 1, 60 mg (86 μmol) of the compounds prepared according to Example 25a were converted and, after workup and purification, 9.3 mg (18%) of the title compounds were isolated as a colourless foam.

In analogy to Example 24a, 50 mg (80 μmol) of the compound prepared according to Example 2a were converted using O-isobutylhydroxylamine and, after workup and purification, 47 mg (84%) of the title compounds were isolated as a colourless foam.

EXAMPLE 27

(E/Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]propynal O-(3,4-dichlorobenzyl) oxime

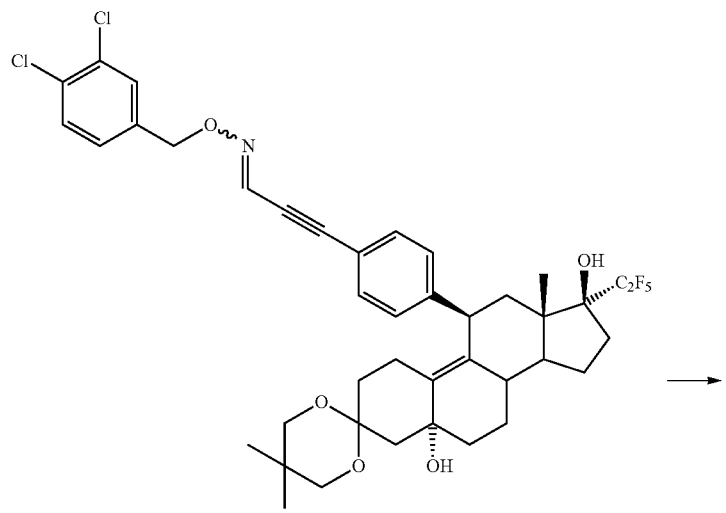

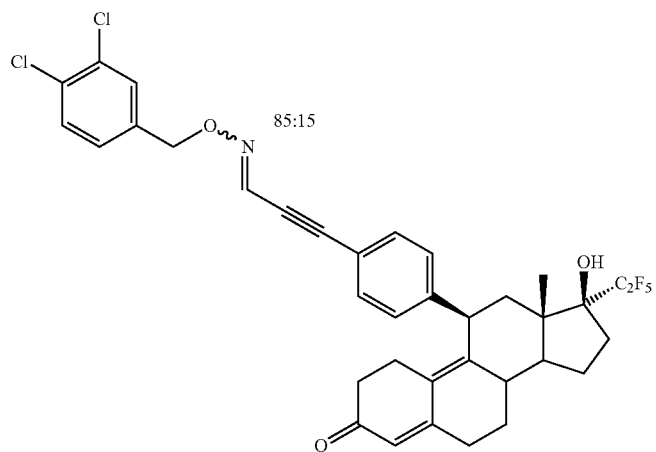

In analogy to Example 1, 71 mg (80 μmol) of the compounds prepared according to Example 27a were converted and, after workup and purification, 26 mg (47%) of the title compounds were isolated as a colourless foam.

$^1$H NMR (CDCl$_3$):=0.57 (3H), 1.39-1.56 (2H), 1.71-1.88 (3H), 2.05 (1H), 2.07 (1H), 2.18-2.66 (9H), 2.72 (1H), 4.44 (1H), 5.12+5.18 (2H), 5.79 (1H), 6.94+7.61 (1H), 7.12-7.28 (3H), 7.37-7.54 (4H) ppm.

EXAMPLE 27a (E/Z)-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxane]-11-yl)phenyl]propynal O-(3,4-dichlorobenzyl) oxime

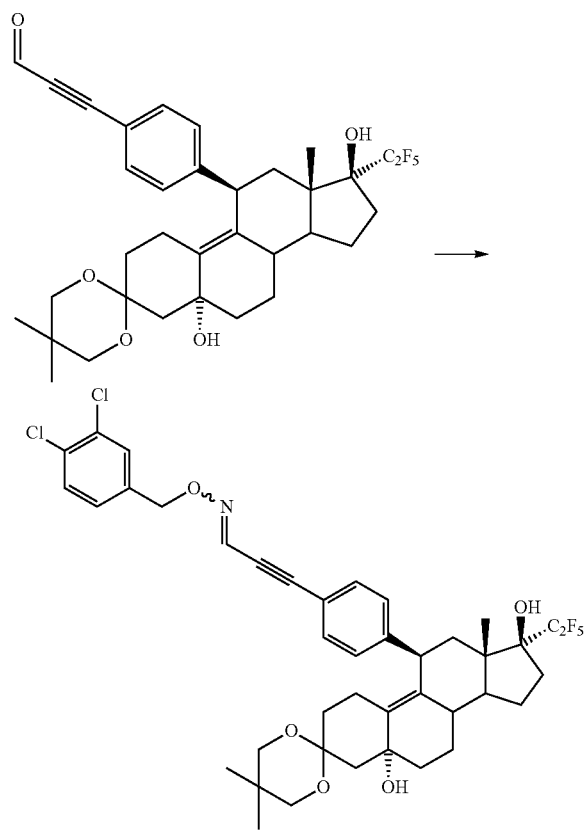

In analogy to Example 24a, 50 mg (80 μmol) of the compound prepared according to Example 2a were converted using O-(3,4-dichlorobenzyl)hydroxylamine and, after workup, 71 mg of the title compound were isolated as a crude product.

EXAMPLE 28

1-(3,5-dimethylisoxazol-4-yl)-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl}urea

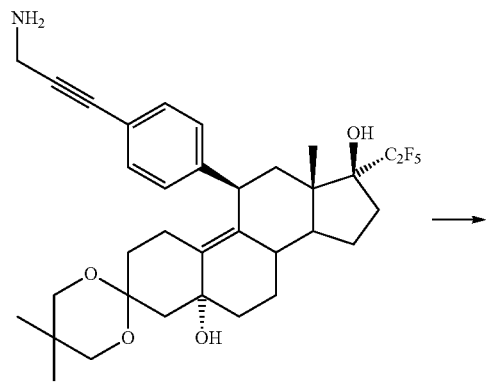

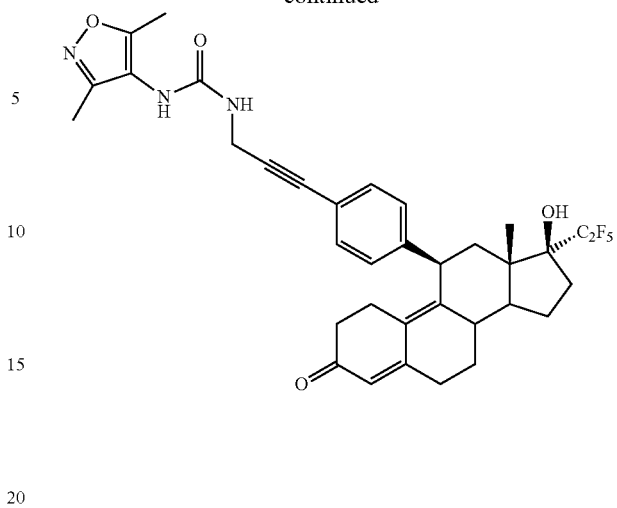

The solution of 25.6 mg (38 μmol) of the compound prepared according to Example 28a in 1 ml of dichloromethane was admixed with 5.8 mg of 3,5-dimethylisoxazol-4-yl isocyanate and stirred at 23° C. for 1 hour. 57 μl of a 4 molar solution of hydrogen chloride in dioxane and, after 10 minutes, 31.7 μl of triethylamine were added. The mixture was concentrated and the residue was purified by chromatography. 15.2 mg (61%) of the title compound were isolated as a colourless foam.

$^1$H NMR (CDCl$_3$):=0.56 (3H), 1.38-1.53 (2H), 1.70-1.87 (2H), 1.98-2.10 (2H), 2.12-2.63 (9H), 2.16 (3H), 2.31 (3H), 2.71 (1H), 3.09 (1H), 4.20 (2H), 4.41 (1H), 5.23 (1H), 5.77 (1H), 6.17 (1H), 7.10 (2H), 7.27 (2H) ppm.

EXAMPLE 28a (5R,8S,11R,13S,14S,17S)-11-[4-(3-aminoprop-1-yn-1-yl)phenyl]-17-pentafluoroethyl-5',5',13-trimethyl-1,2,3,4,6,7,8,11,12,13,14,15,16,17-tetradecahydrospiro[cyclopenta[a]phenanthrene-3,2'-[1,3]dioxane]-5,17-diol

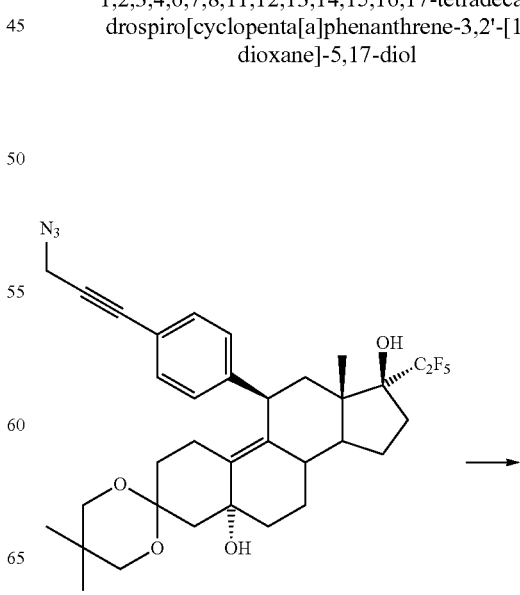

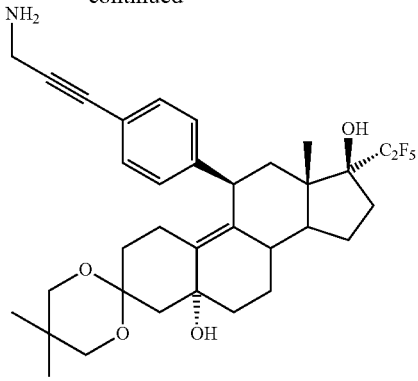

The solution of 267 mg (0.41 mmol) of the compound prepared according to Example 23a in 10 ml of tetrahydrofuran was admixed with 2 ml of water, 1 ml of trimethylphosphine, and stirred at 23° C. for 4 hours. 1 ml of a 25% ammonia solution was added, and the mixture was stirred at 23° C. for a further 16 hours and concentrated. The title compound obtained as a crude product was converted further without purification.

EXAMPLE 29

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-isopropylurea

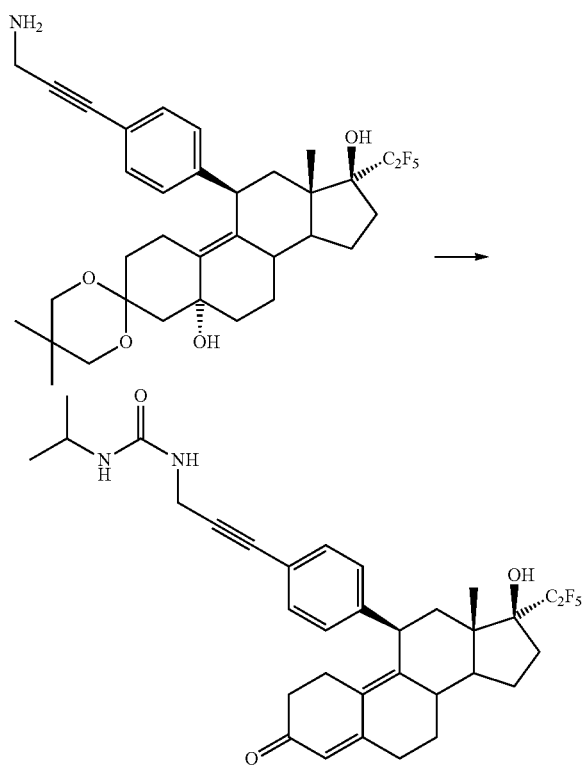

In analogy to Example 28, 35 mg (52 μmol) of the compound prepared according to Example 28a were converted using isopropyl isocyanate and, after workup and purification, 19.5 mg (62%) of the title compound were isolated as a colourless foam.

$^1$H NMR (CDCl$_3$):=0.57 (3H), 1.11 (6H), 1.39-1.54 (2H), 1.72-1.87 (3H), 2.04 (1H), 2.18-2.64 (9H), 2.70 (1H), 3.40 (1H), 3.85 (1H), 4.14 (2H), 4.40 (1H), 4.74 (1H), 5.03 (1H), 5.77 (1H), 7.10 (2H), 7.30 (2H) ppm.

EXAMPLE 30

3-(3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl}ureido)propionic acid ethyl ester

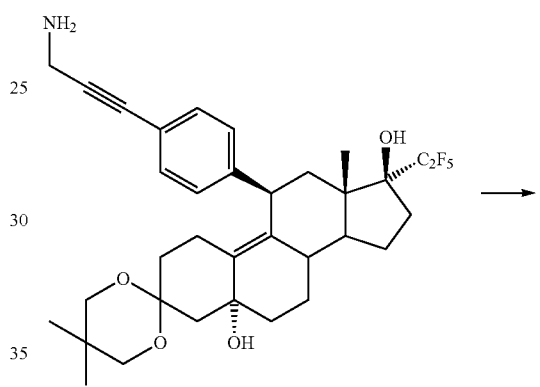

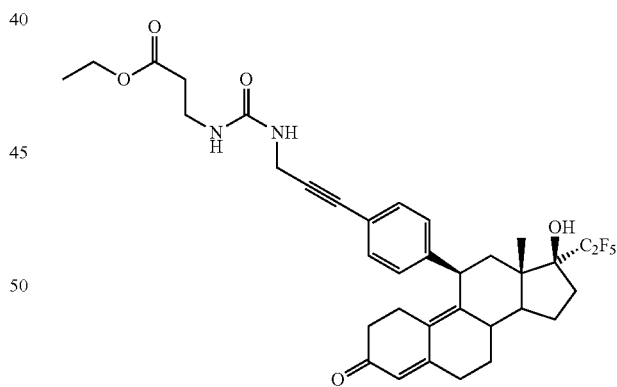

In analogy to Example 28, 25 mg (37 μmol) of the compound prepared according to Example 28a were converted using ethyl 3-isocyanatopropionate and, after workup and purification, 16.7 mg (68%) of the title compound were isolated as a colourless foam.

$^1$H NMR (CDCl$_3$):=0.57 (3H), 1.23 (3H), 1.37-1.54 (2H), 1.71-1.87 (3H), 2.05 (1H), 2.17-2.63 (11H), 2.71 (1H), 3.09 (1H), 3.45 (2H), 4.07-4.19 (4H), 4.41 (1H), 4.98 (1H), 5.29 (1H), 5.77 (1H), 7.11 (2H), 7.31 (2H) ppm.

EXAMPLE 31

1-ethyl-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl}urea

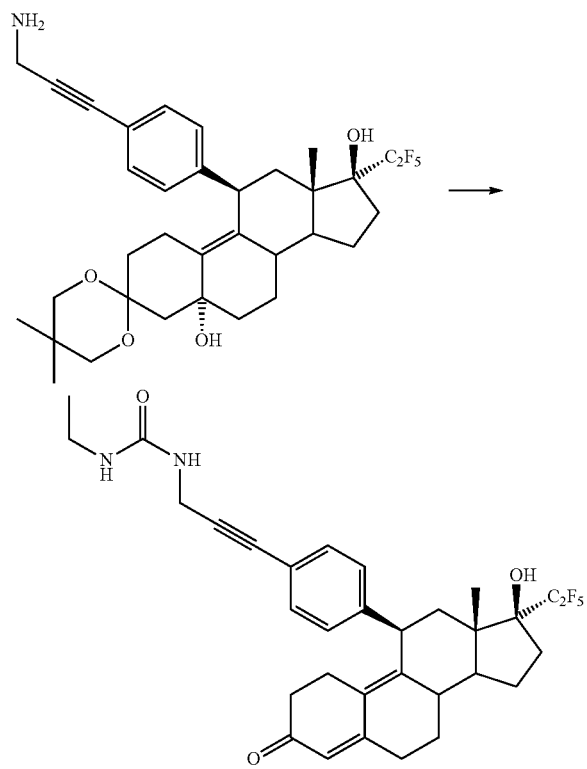

In analogy to Example 28, 88 mg (0.11 mmol) of the compound prepared according to Example 28a were converted using ethyl isocyanate and, after workup and purification, 35 mg (43%) of the title compound were isolated as a colourless foam.

$^1$H NMR (CDCl$_3$):=0.57 (3H), 1.12 (3H), 1.37-1.57 (2H), 1.71-1.89 (3H), 2.05 (1H), 2.16-2.65 (9H), 2.70 (1H), 2.82 (1H), 3.22 (2H), 4.17 (2H), 4.42 (1H), 4.60 (1H), 4.76 (1H), 5.78 (1H), 7.11 (2H), 7.32 (2H) ppm.

EXAMPLE 32

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-methoxyphenyl)urea

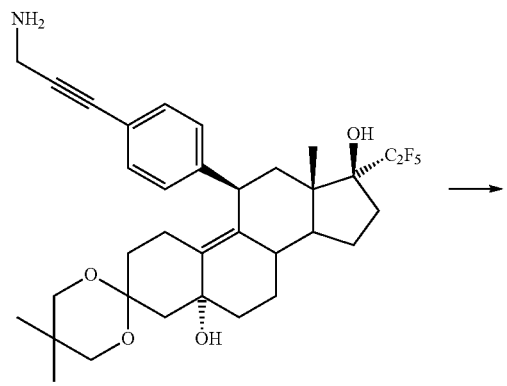

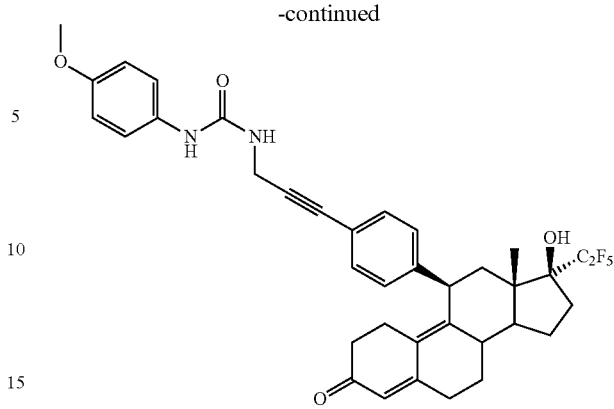

In analogy to Example 28, 25 mg (37 μmol) of the compound prepared according to Example 28a were converted using 4-methoxyphenyl isocyanate and, after workup and purification, 12 mg (49%) of the title compound were isolated as a colourless foam.

$^1$H NMR (CDCl$_3$):=0.55 (3H), 1.38-1.52 (2H), 1.71-1.86 (3H), 2.04 (1H), 2.17-2.62 (9H), 2.69 (1H), 3.00 (1H), 3.75 (3H), 4.20 (2H), 4.39 (1H), 5.42 (1H), 5.77 (1H), 6.81 (2H), 6.88 (1H), 7.07 (2H), 7.18 (2H), 7.28 (2H) ppm.

EXAMPLE 33

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-tert-butylphenyl)urea

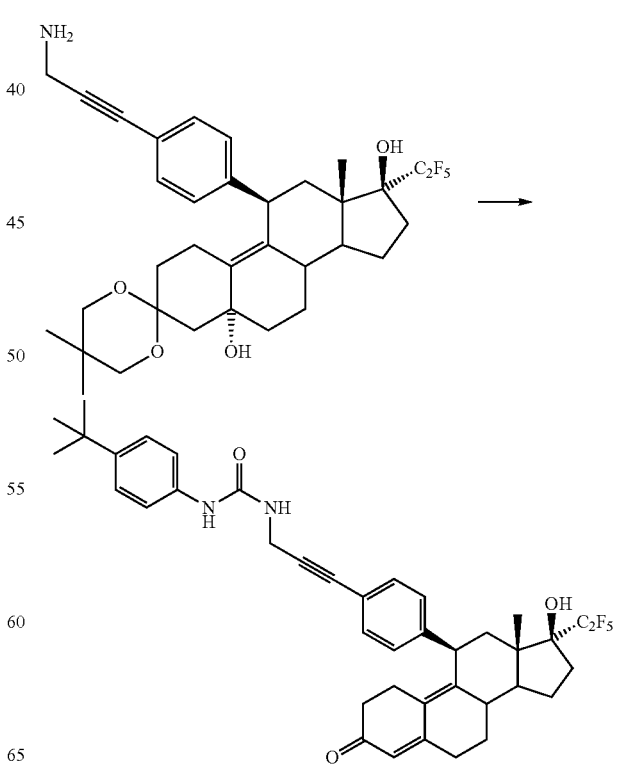

In analogy to Example 28, 25.6 mg (38 μmol) of the compound prepared according to Example 28a were converted using 4-tert-butylphenyl isocyanate and, after workup and purification, 11.8 mg (44%) of the title compound were isolated as a colourless foam.

¹H NMR (CDCl₃):=0.55 (3H), 1.27 (9H), 1.38-1.52 (2H), 1.72-1.86 (3H), 2.04 (1H), 2.17-2.63 (9H), 2.69 (1H), 2.88 (1H), 4.22 (2H), 4.39 (1H), 5.52 (1H), 5.77 (1H), 6.95 (1H), 7.08 (2H), 7.20 (2H), 7.28 (2H), 7.30 (2H) ppm.

EXAMPLE 34

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-phenylurea

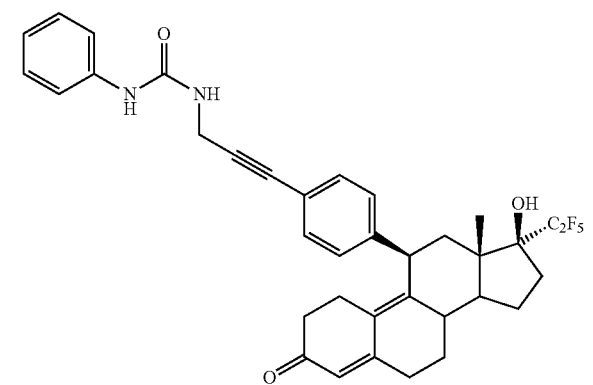

In analogy to Example 28, 25.6 mg (38 μmol) of the compound prepared according to Example 28a were converted using phenyl isocyanate and, after workup and purification, 12 mg (49%) of the title compound were isolated as a colourless foam.

¹H NMR (CDCl₃):=0.55 (3H), 1.37-1.52 (2H), 1.72-1.86 (3H), 2.03 (1H), 2.16-2.62 (9H), 2.68 (1H), 2.94 (1H), 4.21 (2H), 4.38 (1H), 5.67 (1H), 5.77 (1H), 7.08 (1H), 7.07 (2H), 7.19 (1H), 7.21-7.32 (6H) ppm.

EXAMPLE 35

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-chlorophenyl)urea

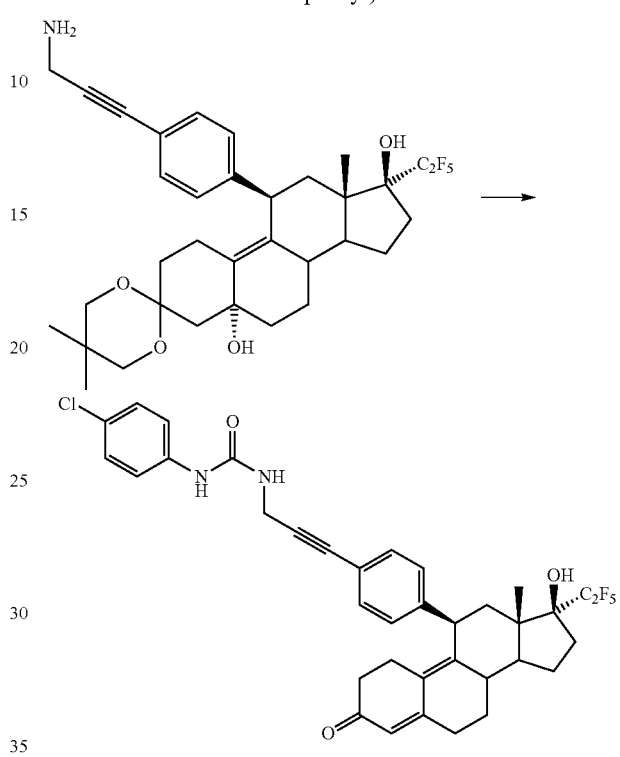

In analogy to Example 28, 25 mg (37 μmol) of the compound prepared according to Example 28a were converted using 4-chlorophenyl isocyanate and, after workup and purification, 8.9 mg (35%) of the title compound were isolated as a colourless foam.

¹H NMR (CDCl₃):=0.55 (3H), 1.39-1.52 (2H), 1.72-1.89 (3H), 2.04 (1H), 2.16-2.62 (9H), 2.69 (1H), 2.87 (1H), 4.21 (2H), 4.39 (1H), 5.73 (1H), 5.77 (1H), 7.07 (2H), 7.17 (2H), 7.24 (2H), 7.26 (2H), 7.36 (1H) ppm.

EXAMPLE 36

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-fluorophenyl)urea

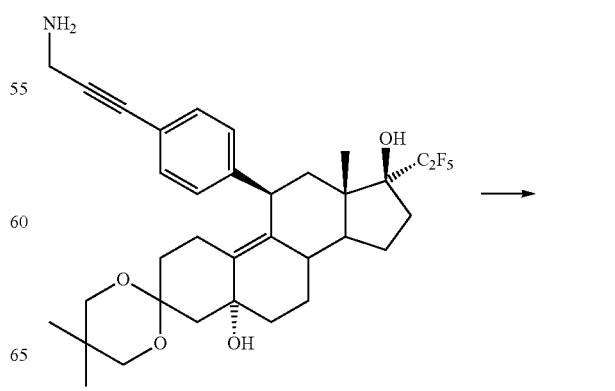

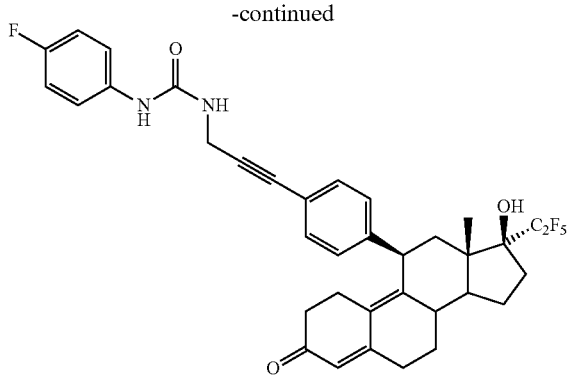

In analogy to Example 28, 25.6 mg (38 μmol) of the compound prepared according to Example 28a were converted using 4-fluorophenyl isocyanate and, after workup and purification, 13.3 mg (53%) of the title compound were isolated as a colourless foam.

$^1$H NMR (CDCl$_3$):=0.55 (3H), 1.38-1.53 (2H), 1.72-1.87 (3H), 2.03 (1H), 2.16-2.62 (9H), 2.69 (1H), 3.02 (1H), 4.19 (2H), 4.38 (1H), 5.71 (1H), 5.77 (1H), 6.90 (2H), 7.06 (2H), 7.20-7.27 (4H), 7.32 (1H) ppm.

EXAMPLE 37

4-(3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl}ureido)benzoic acid ethyl ester

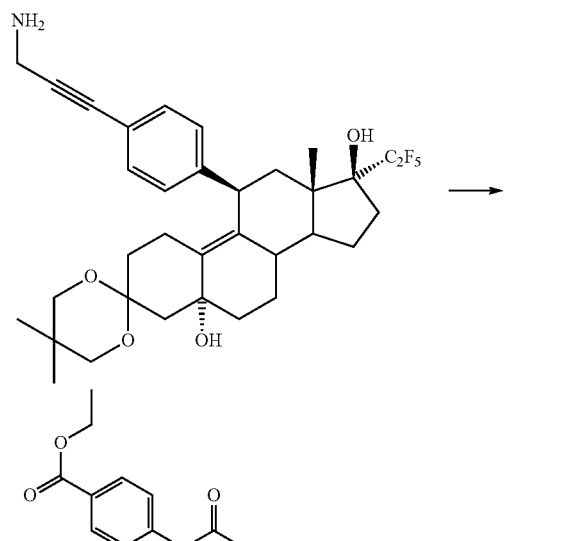

In analogy to Example 28, 25 mg (37 μmol) of the compound prepared according to Example 28a were converted using ethyl 4-isocyanatobenzoate and, after workup and purification, 6.0 mg (23%) of the title compound were isolated as a colourless foam.

$^1$H NMR (CDCl$_3$):=0.58 (3H), 1.36 (3H), 1.39-1.52 (2H), 1.72-1.87 (3H), 2.03 (1H), 2.17-2.63 (9H), 2.69 (1H), 3.30 (1H), 4.19-4.35 (4H), 4.38 (1H), 5.78 (1H), 6.06 (1H), 7.04 (2H), 7.21 (2H), 7.44 (2H), 7.83 (1H), 7.87 (2H) ppm.

EXAMPLE 38

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-methylphenyl)urea

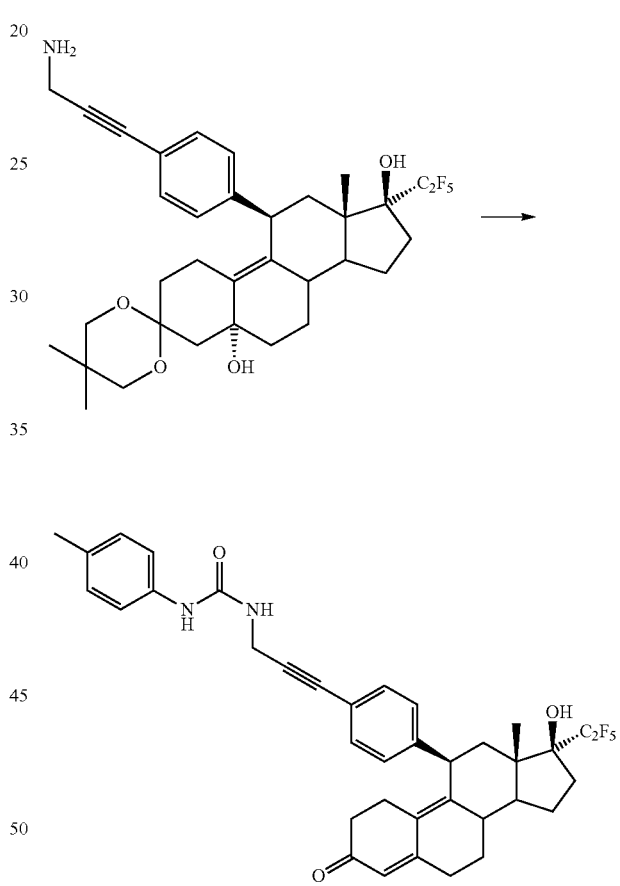

In analogy to Example 28, 25 mg (37 μmol) of the compound prepared according to Example 28a were converted using 4-methylphenyl isocyanate and, after workup and purification, 10.8 mg (44%) of the title compound were isolated as a colourless foam.

$^1$H NMR (CDCl$_3$):=0.55 (3H), 1.37-1.54 (2H), 1.70-1.82 (3H), 2.04 (1H), 2.15-2.63 (9H), 2.28 (3H), 2.69 (1H), 2.90 (1H), 4.20 (2H), 4.39 (1H), 5.47 (1H), 5.77 (1H), 6.92 (1H), 7.07 (4H), 7.16 (2H), 7.28 (2H) ppm.

EXAMPLE 39

1-benzyl-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl}urea

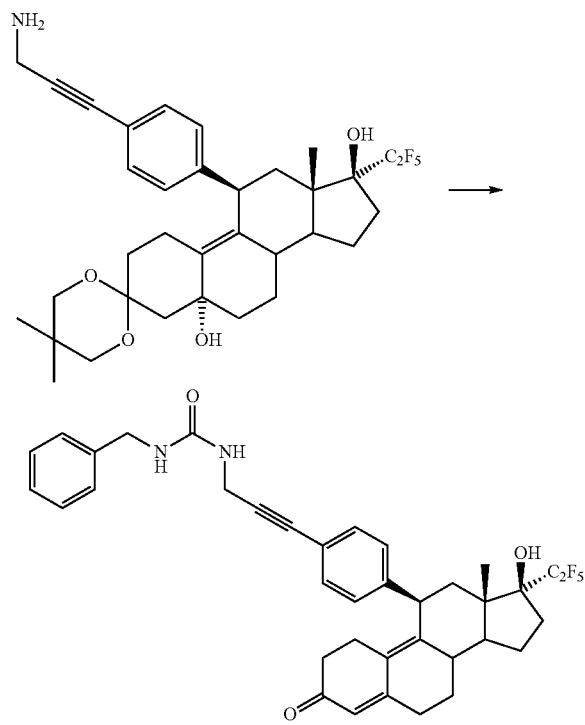

In analogy to Example 28, 35 mg (52 µmol) of the compound prepared according to Example 28a were converted using benzyl isocyanate and, after workup and purification, 17.5 mg (51%) of the title compound were isolated as a colourless foam.

$^1$H NMR (CDCl$_3$):=0.56 (3H), 1.36-1.53 (2H), 1.70-1.98 (3H), 2.04 (1H), 2.14-2.62 (9H), 2.67 (1H), 3.28 (1H), 4.11 (2H), 4.29 (2H), 4.38 (1H), 5.26 (1H), 5.37 (1H), 5.75 (1H), 7.08 (2H), 7.19-7.30 (7H) ppm.

EXAMPLE 40

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-tert-butylurea

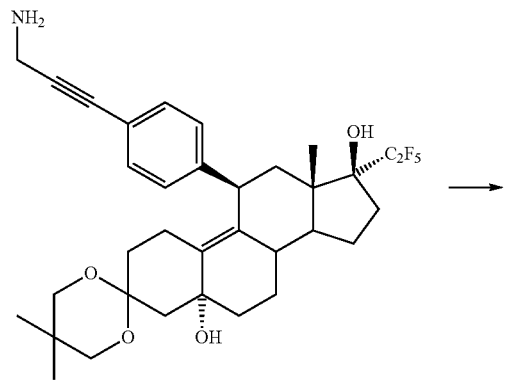

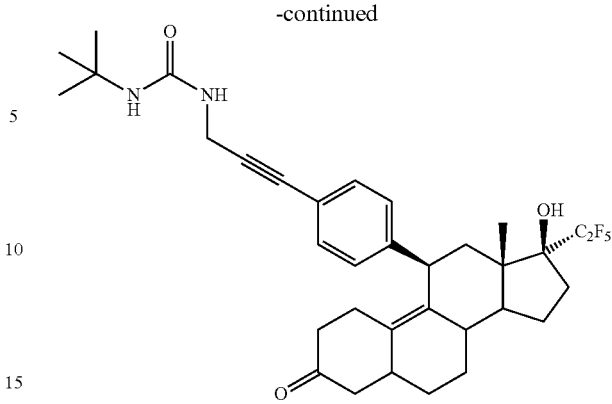

In analogy to Example 28, 35 mg (52 µmol) of the compound prepared according to Example 28a were converted using tert-butyl isocyanate and, after workup and purification, 12.6 mg (39%) of the title compound were isolated as a colourless foam.

$^1$H NMR (CDCl$_3$):=0.57 (3H), 1.33 (9H), 1.37-1.56 (2H), 1.72-1.88 (3H), 2.05 (1H), 2.18-2.64 (9H), 2.64-2.78 (2H), 4.13 (2H), 4.41 (1H), 4.53 (1H), 4.63 (1H), 5.78 (1H), 7.10 (2H), 7.31 (2H) ppm.

EXAMPLE 41

1-allyl-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl}urea

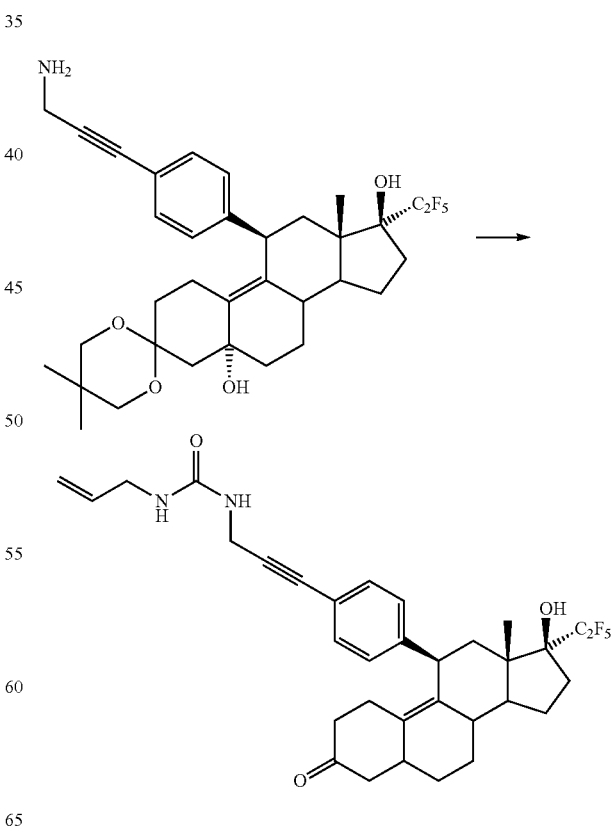

In analogy to Example 28, 25 mg (37 µmol) of the compound prepared according to Example 28a were converted using allyl isocyanate and, after workup and purification, 6.3 mg (28%) of the title compound were isolated as a colourless foam.

$^1$H NMR (CDCl$_3$):=0.57 (3H), 1.38-1.56 (2H). 1.71-1.88 (3H), 2.05 (1H), 2.15-2.63 (9H), 2.70 (1H), 2.72 (1H), 3.81 (2H), 4.18 (2H), 4.41 (1H), 4.79 (1H), 4.88 (1H), 5.11 (1H), 5.20 (1H), 5.78 (1H), 5.84 (1H), 7.11 (2H), 7.32 (2H) ppm.

EXAMPLE 42

(3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl}ureido)acetic acid ethyl ester

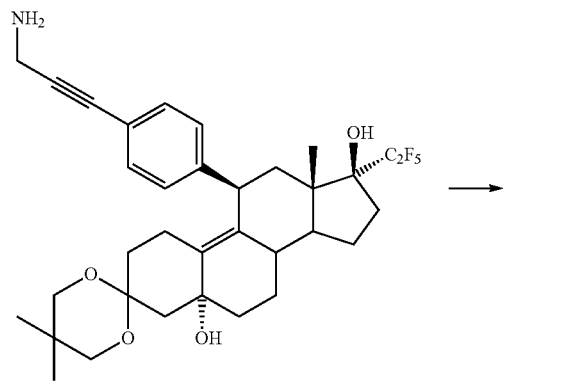

In analogy to Example 28, 35 mg (52 μmol) of the compound prepared according to Example 28a were converted using ethyl isocyanatoacetate and, after workup and purification, 17.1 mg (51%) of the title compound were isolated as a colourless foam.

$^1$H NMR (CDCl$_3$):=0.56 (3H), 1.24 (3H), 1.36-1.56 (2H), 1.39-1.88 (3H), 2.05 (1H), 2.16-2.63 (9H), 2.70 (1H), 3.15 (1H), 3.98 (2H), 4.11-4.23 (4H), 4.40 (1H), 5.34 (1H), 5.46 (1H), 5.77 (1H), 7.10 (2H), 7.31 (2H) ppm.

EXAMPLE 43

1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-piperidin-1-ylphenyl)urea

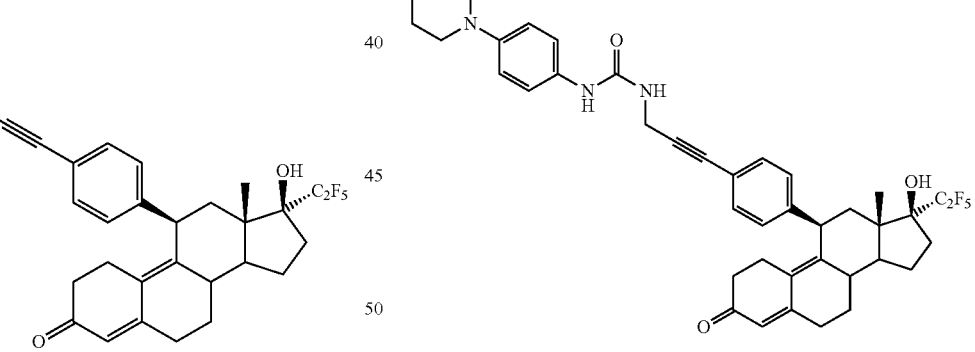

In analogy to Example 28, 28 mg (38 μmol) of the compound prepared according to Example 28a were converted using 4-piperidin-1-ylphenyl isocyanate and, after workup and purification, 8.4 mg (31%) of the title compound were isolated as a colourless foam.

$^1$H NMR (CDCl$_3$):=0.56 (3H), 1.38-1.87 (11H), 2.05 (1H), 2.17-2.64 (9H), 2.68 (1H), 2.70 (1H), 3.12 (4H), 4.22 (2H), 4.40 (1H), 5.07 (1H), 5.78 (1H), 6.40 (1H), 6.89 (2H), 7.09 (2H), 7.13 (2H), 7.31 (2H) ppm.

EXAMPLE 44 allylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

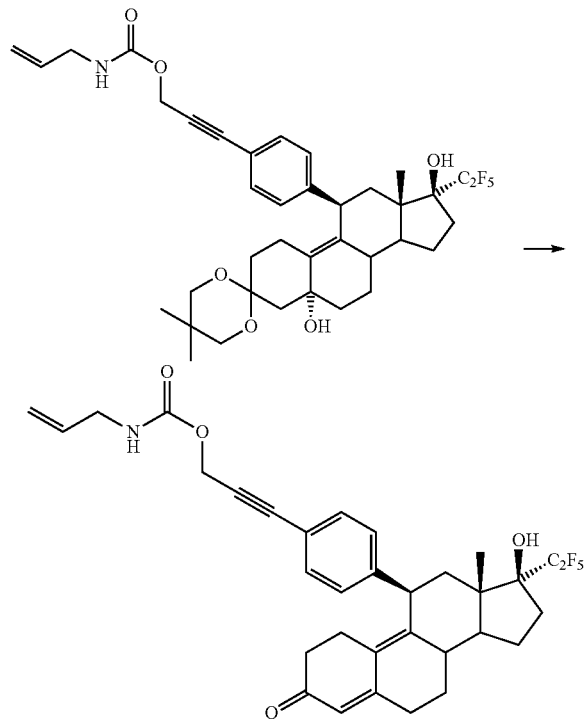

In analogy to Example 1, 89 mg (80 μmol) of the compound prepared according to Example 44a were converted and, after workup and purification, 25 mg (52%) of the title compound were isolated as a colourless foam.

$^1$H NMR (CDCl$_3$):=0.57 (3H), 1.40-1.55 (2H), 1.73-1.86 (3H), 2.07 (1H), 2.11 (1H), 2.21-2.65 (9H), 2.72 (1H), 3.84 (2H), 4.43 (1H), 4.87 (1H), 4.91 (2H), 5.14 (1H), 5.21 (1H), 5.79 (1H), 5.85 (1H), 7.13 (2H), 7.38 (2H) ppm.

EXAMPLE 44a allylcarbamic acid 3-[4-((5R,8S,11R,13S,14S,17S)-5,17-dihydroxy-17-pentafluoroethyl-5,5',13-trimethyl-2,3,4,5,6,7,8,11,12,13,14,15,16,17-tetradecahydro-1H-spiro[cyclopenta[a]phenanthrene-3,2'-[1,3]dioxane]-11-yl)phenyl]prop-2-ynyl ester

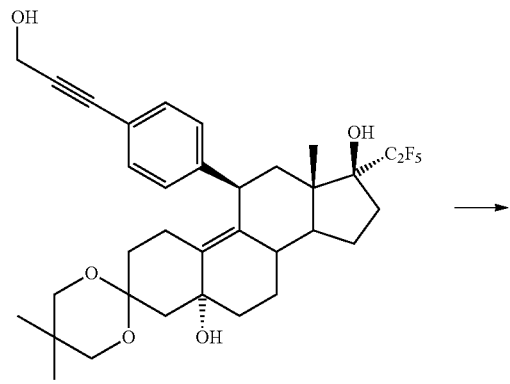

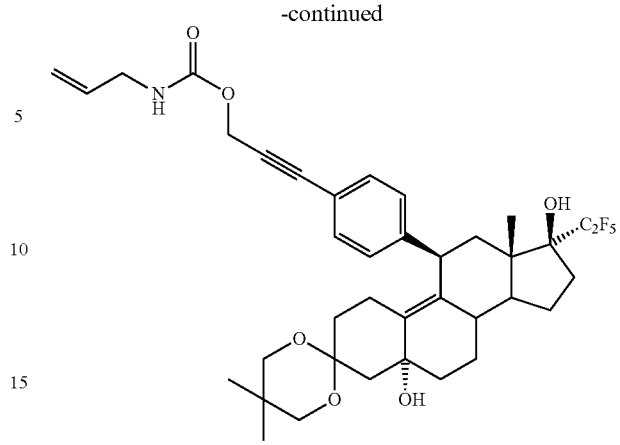

The solution of 50 mg (80 μmol) of the compound prepared according to Example 1a in 1.5 ml of dichloromethane was admixed with 424 μl of allyl isocyanate and stirred at 23° C. for 3.5 days. The mixture was concentrated and the residue was converted further without purification.

EXAMPLE 45 ethylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

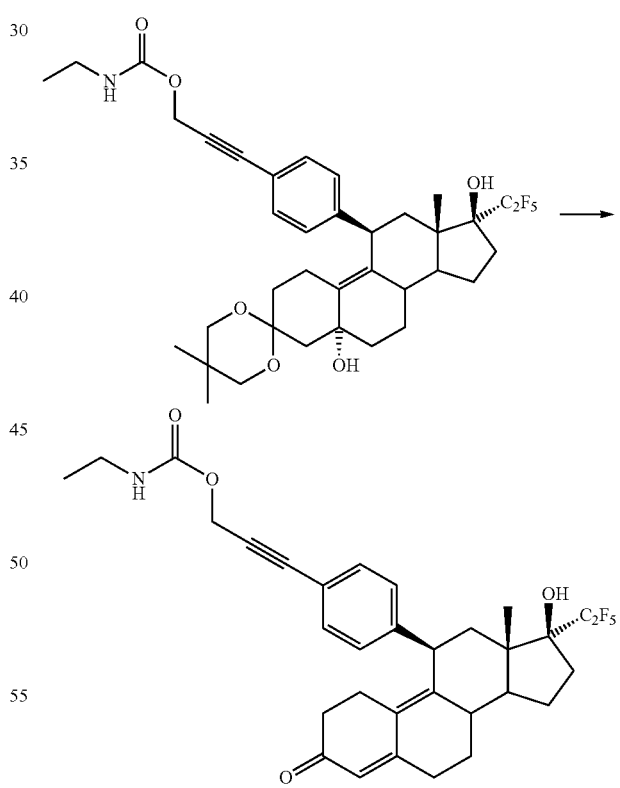

In analogy to Example 1, 27 mg (39 μmol) of the compound prepared according to Example 45a were converted and, after workup and purification, 12 mg (53%) of the title compound were isolated as a colourless foam.

$^1$H NMR (CDCl$_3$):=0.57 (3H), 1.15 (3H), 1.38-1.57 (2H), 1.70-1.88 (3H), 2.06 (1H), 2.17-2.64 (10H), 2.71 (1H), 3.24 (2H), 4.43 (1H), 4.77 (1H), 4.88 (2H), 5.78 (1H), 7.13 (2H), 7.37 (2H) ppm.

EXAMPLE 45a ethylcarbamic acid 3-[4-((5R,8S,11R,13S,14S,17S)-5,17-dihydroxy-17-pentafluoroethyl-5',5',13-trimethyl-2,3,4,5,6,7,8,11,12,13,14,15,16,17-tetradecahydro-1H-spiro[cyclopenta[a]phenanthrene-3,2'-[1,3]dioxane]-11-yl)phenyl]prop-2-ynyl ester

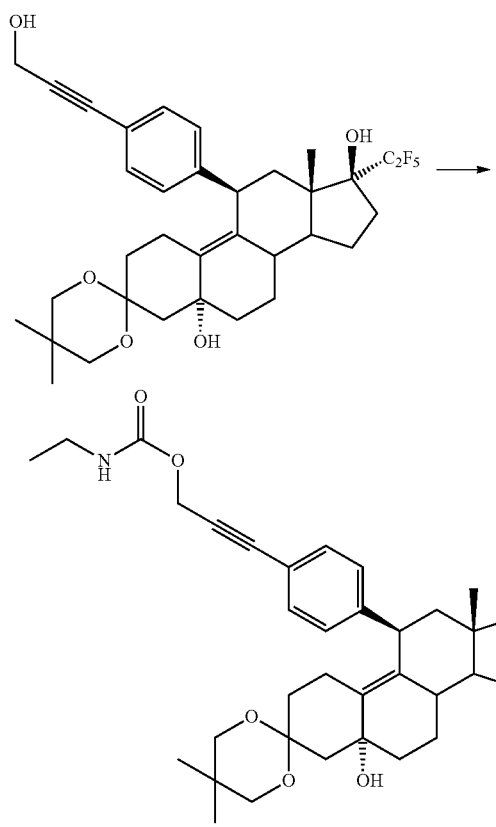

In analogy to Example 44a, 50 mg (80 µmol) of the compound prepared according to Example 1a were converted at 60° C. using ethyl isocyanate and, after workup and purification, 27 mg (48%) of the title compound were isolated as a colourless foam.

EXAMPLE 46 phenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

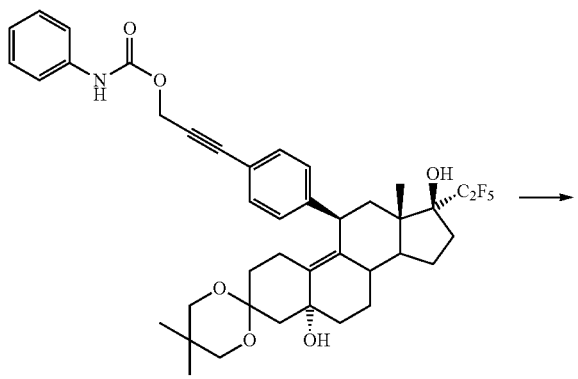

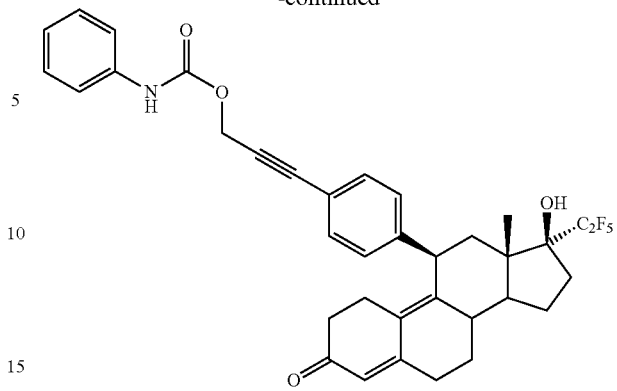

In analogy to Example 1, 53.4 mg (72 µmol) of the compound prepared according to Example 46a were converted and, after workup and purification, 17.4 mg (38%) of the title compound were isolated as a colourless foam.

$^1$H NMR (CDCl$_3$):=0.57 (3H), 1.40-1.55 (2H), 1.73-1.85 (3H), 2.06 (1H), 2.18-2.64 (10H), 2.71 (1H), 4.43 (1H), 5.00 (2H), 5.79 (1H), 6.80 (1H), 7.08 (1H), 7.13 (2H), 7.31 (2H), 7.37 (2H), 7.39 (2H) ppm.

EXAMPLE 46a phenylcarbamic acid 3-[4-((5R,8S,11R,13S,14S,17S)-5,17-dihydroxy-17-pentafluoroethyl-5',5',13-trimethyl-2,3,4,5,6,7,8,11,12,13,14,15,16,17-tetradecahydro-1H-spiro[cyclopenta[a]phenanthrene-3,2'-[1,3]dioxane]-11-yl)phenyl]prop-2-ynyl ester

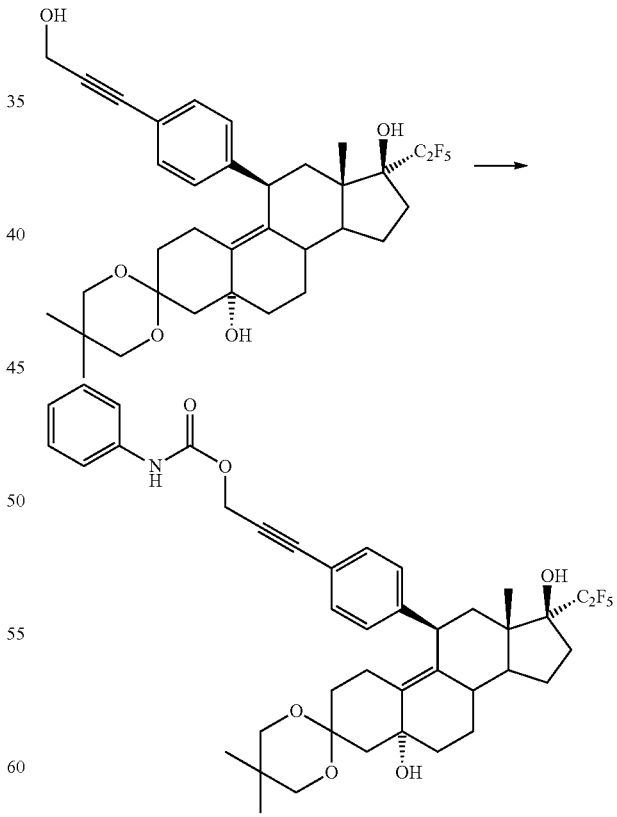

In analogy to Example 44a, 50 mg (80 µmol) of the compound prepared according to Example 1a were converted using phenyl isocyanate and, after workup and purification, 53 mg (90%) of the title compound were isolated as a colourless foam.

EXAMPLE 47

4-methylphenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

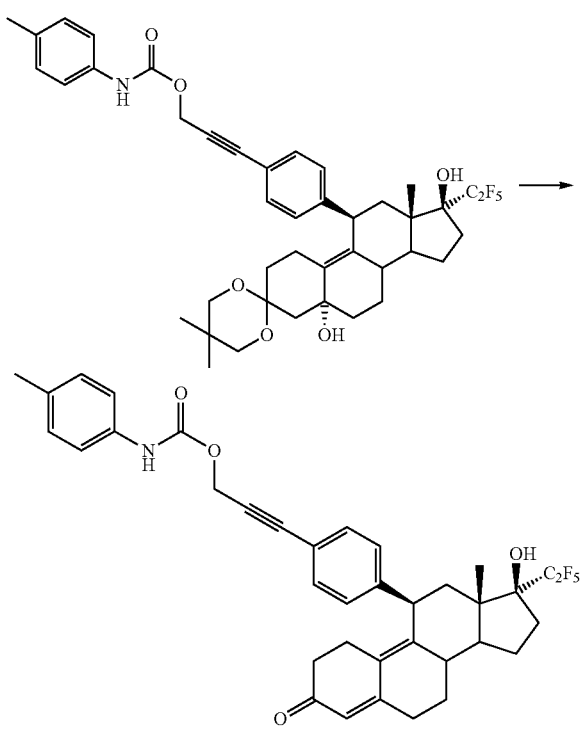

In analogy to Example 1, 25 mg (33 µmol) of the compound prepared according to Example 47a were converted and, after workup and purification, 8.2 mg (38%) of the title compound were isolated as a colourless foam.

$^1$H NMR (CDCl$_3$):=0.57 (3H), 1.38-1.56 (2H), 1.71-1.86 (3H), 2.07 (1H), 2.11 (1H), 2.18-2.66 (9H), 2.31 (3H), 2.71 (1H), 4.43 (1H), 4.99 (2H), 5.79 (1H), 6.66 (1H), 7.11 (2H), 7.14 (2H), 7.27 (2H), 7.38 (2H) ppm.

EXAMPLE 47a 4-methylphenylcarbamic acid 3-[4-((5R,8S,11R,13S,14S,17S)-5,17-dihydroxy-17-pentafluoroethyl-5',5',13-trimethyl-2,3,4,5,6,7,8,11,12,13,14,15,16,17-tetradecahydro-1H-spiro[cyclopenta[a]phenanthrene-3,2'-[1,3]dioxane]-11-yl)phenyl]prop-2-ynyl ester

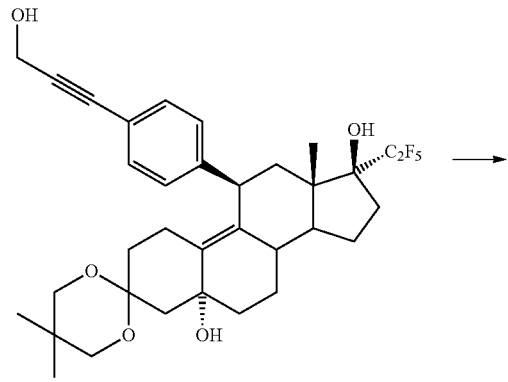

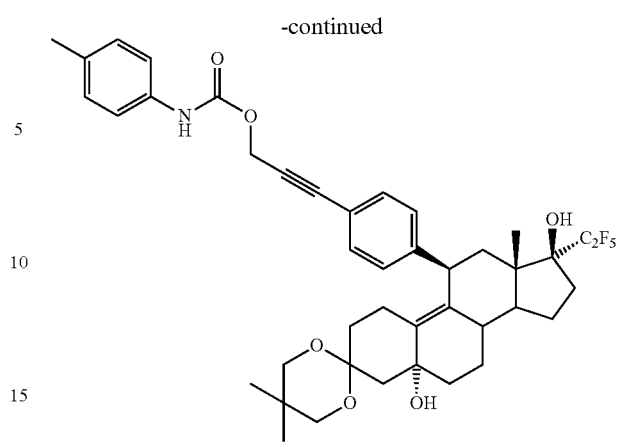

In analogy to Example 44a, 50 mg (80 µmol) of the compound prepared according to Example 1a were converted using 4-methylphenyl isocyanate and, after workup and purification, 25 mg (42%) of the title compound were isolated as a colourless foam.

EXAMPLE 48

4-fluorophenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

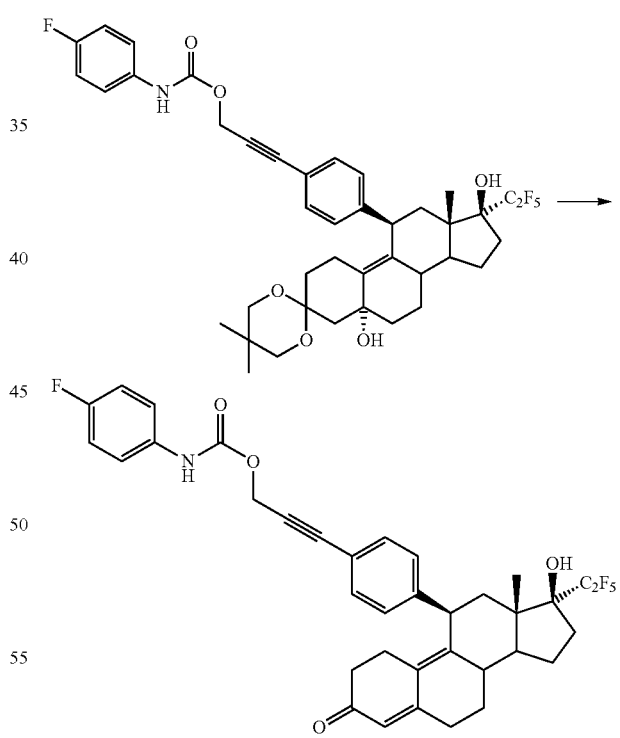

In analogy to Example 1, 157 mg (80 µmol) of the compound prepared according to Example 48a were converted and, after workup and purification, 9.2 mg (18%) of the title compound were isolated as a colourless foam.

$^1$H NMR (CDCl$_3$):=0.57 (3H), 1.39-1.55 (2H), 1.74-1.85 (3H), 2.07 (1H), 2.10 (1H), 2.20-2.64 (9H), 2.71 (1H), 4.44 (1H), 5.00 (2H), 5.79 (1H), 6.72 (1H), 7.01 (2H), 7.14 (2H), 7.35 (2H), 7.38 (2H) ppm.

EXAMPLE 48a 4-fluorophenylcarbamic acid 3-[4-((5R,8S,11R,13S,14S,17S)-5,17-dihydroxy-17-pentafluoroethyl-5',5',13-trimethyl-2,3,4,5,6,7,8,11,12,13,14,15,16,17-tetradecahydro-1H-spiro[cyclopenta[a]phenanthrene-3,2'-[1,3]dioxane]-11-yl)phenyl]prop-2-ynyl ester

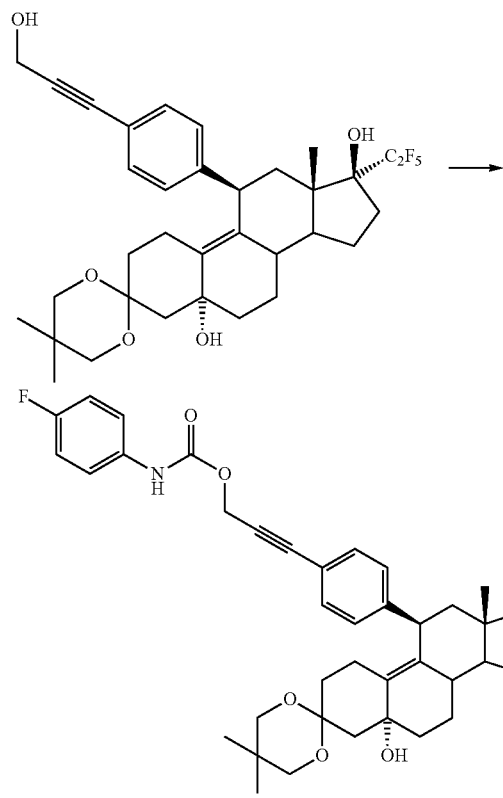

In analogy to Example 44a, 50 mg (80 μmol) of the compound prepared according to Example 1a were converted using 4-fluorophenyl isocyanate and the title compound was isolated as a crude product, which was converted further without purification.

EXAMPLE 49 isopropylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

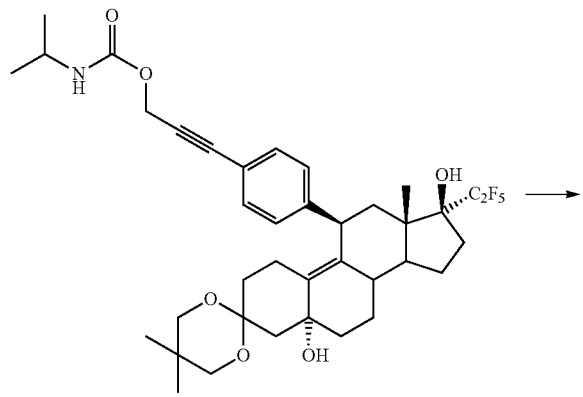

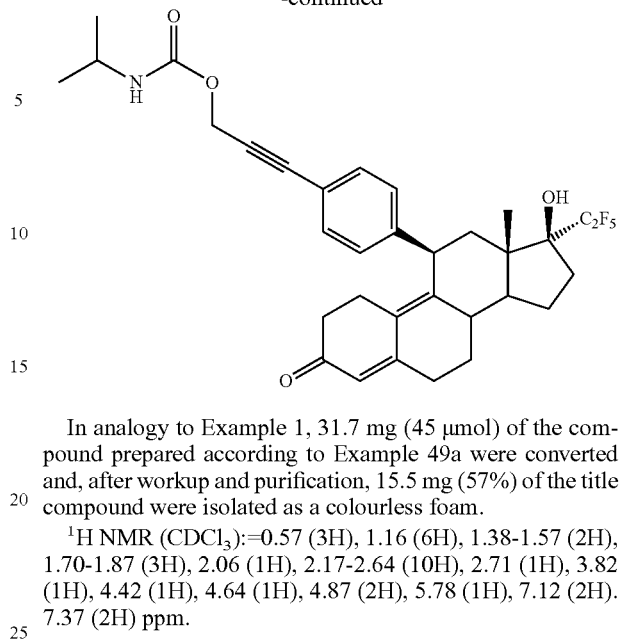

In analogy to Example 1, 31.7 mg (45 μmol) of the compound prepared according to Example 49a were converted and, after workup and purification, 15.5 mg (57%) of the title compound were isolated as a colourless foam.

$^1$H NMR (CDCl$_3$):=0.57 (3H), 1.16 (6H), 1.38-1.57 (2H), 1.70-1.87 (3H), 2.06 (1H), 2.17-2.64 (10H), 2.71 (1H), 3.82 (1H), 4.42 (1H), 4.64 (1H), 4.87 (2H), 5.78 (1H), 7.12 (2H), 7.37 (2H) ppm.

EXAMPLE 49a isopropylcarbamic acid 3-[4-((5R,8S,11R,13S,14S,17S)-5,17-dihydroxy-17-pentafluoroethyl-5',5',13-trimethyl-2,3,4,5,6,7,8,11,12,13,14,15,16,17-tetradecahydro-1H-spiro[cyclopenta[a]phenanthrene-3,2'-[1,3]dioxane]-11-yl)phenyl]prop-2-ynyl ester

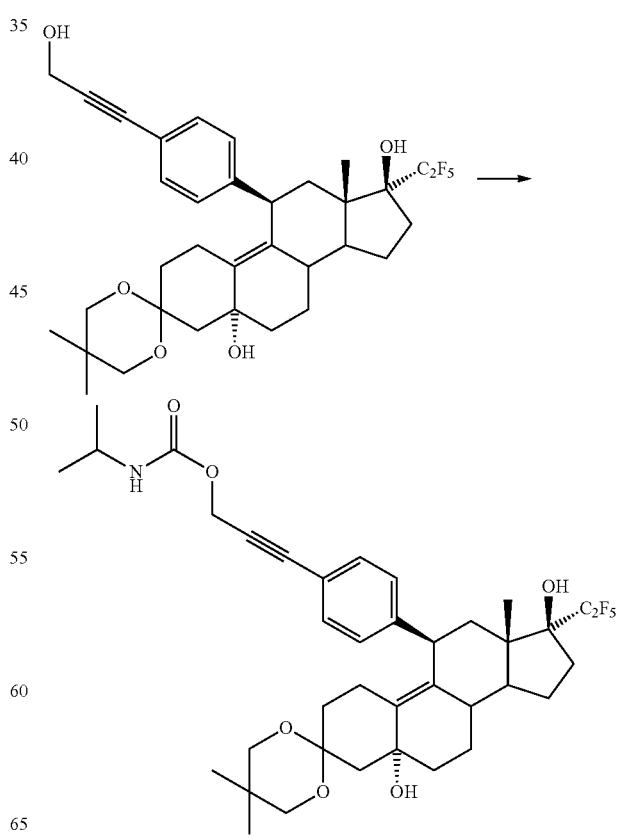

87

In analogy to Example 44a, 50 mg (80 μmol) of the compound prepared according to Example 1a were converted using isopropyl isocyanate and, after workup and purification, 31.7 mg (56%) of the title compound were isolated as a colourless foam.

EXAMPLE 50 benzylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

88

$^1$H NMR (CDCl$_3$):=0.57 (3H), 1.42-1.55 (2H), 1.74-1.87 (3H), 2.03-2.11 (2H), 2.20-2.66 (9H), 2.72 (1H), 4.40 (2H), 4.43 (1H), 4.94 (2H), 5.11 (1H), 5.79 (1H), 7.13 (2H), 7.27-7.41 (7H) ppm.

EXAMPLE 50a chloroformic acid 3-[4-((5R,8S,11R,13S,14S,17S)-5,17-dihydroxy-5',5',13-trimethyl-17-pentafluoroethyl-2,3,4,5,6,7,8,11,12,13,14,15,16,17-tetradecahydro-1H-spiro[cyclopenta[a]phenanthrene-3,2'-[1,3]dioxane]-11-yl)phenyl]prop-2-ynyl ester

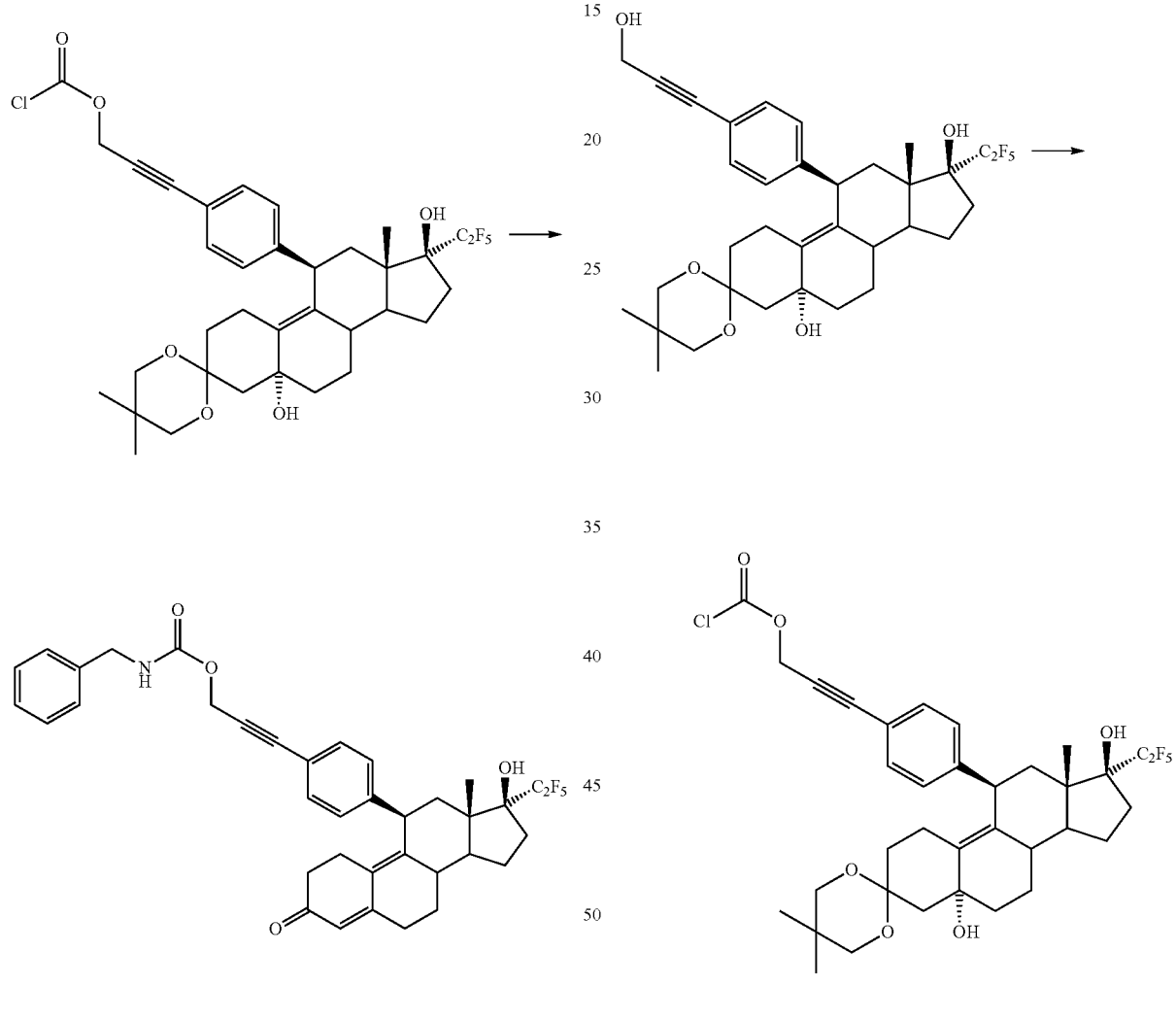

The solution of 39 mg (57 μmol) of the compound prepared according to Example 50a in 0.5 ml of dichloromethane was admixed with the solution of 12.4 μl of benzylamine in 0.5 ml of dichloromethane and stirred at 23° C. for 1 hour. The mixture was admixed with water and extracted repeatedly with dichloromethane, and the combined organic extracts were dried over sodium sulphate. The residue obtained after filtration and removal of solvent was purified by chromatography. 5 mg (13%) of the title compound were isolated as a colourless foam.

The solution of 50 mg (80 μmol) of the compound prepared according to Example 1a in 0.5 ml of dichloromethane was admixed at 0° C. with 12.9 μl of pyridine, 23.8 mg of triphosgene, and stirred for 1.5 hours. The mixture was filtered through a little silica gel, the filtrate was concentrated and the resulting title compound was converted further without purification.

EXAMPLE 51

(8S,11R,13S,14S,17S)-17-hydroxy-11-[4-(3-methanesulphonylphenylethynyl)phenyl]-13-methyl-17-pentafluoroethyl-1,2,6,7,8,11,12,13,14,15,16,17-dodecahydrocyclopenta[a]phenanthren-3-one

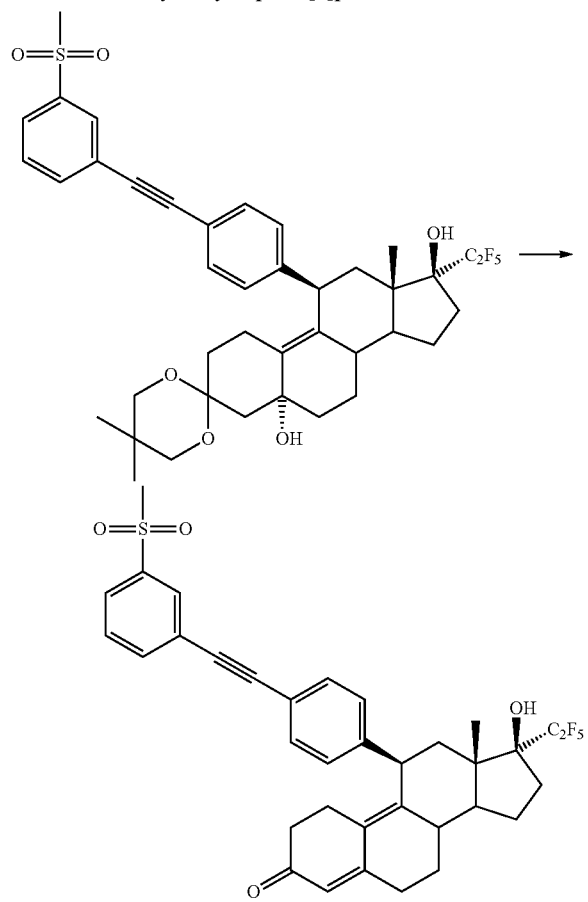

In analogy to Example 1, 23 mg (31 μmol) of the compound prepared according to Example 50a were converted and, after workup and purification, 10 mg (51%) of the title compound were isolated as a colourless foam.

$^1$H NMR (CDCl$_3$):=0.61 (3H), 1.40-1.56 (2H), 1.74-1.88 (3H), 2.08 (1H), 2.18 (1H), 2.22-2.67 (9H), 2.74 (1H), 3.08 (3H), 4.47 (1H), 5.80 (1H), 7.20 (2H), 7.46 (2H), 7.56 (1H), 7.77 (1H), 7.89 (1H), 8.10 (1H) ppm.

EXAMPLE 51a (5R,8S,11R,13S,14S,17S)-11-[4-(3-methanesulphonylphenylethynyl)phenyl]-5',5',13-trimethyl-17-pentafluoroethyl-1,2,3,4,6,7,8,11,12,13,14,15,16,17-tetradecahydro-spiro[cyclopenta[a]phenanthrene-3,2'-[1,3]dioxane]-5,17-diol

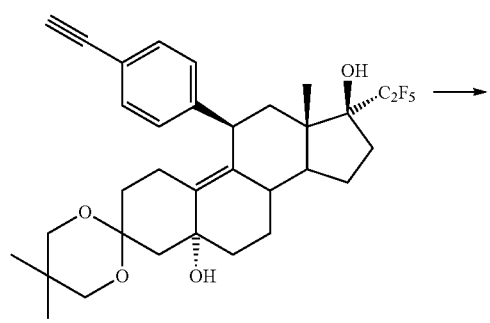

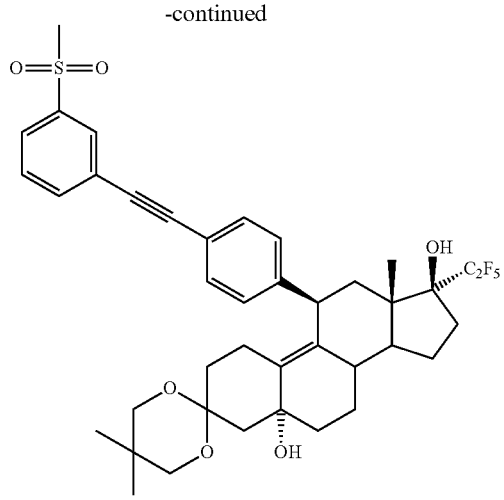

In analogy to Example 17b, 50 mg (84 μmol) of the compound prepared according to Example 15b were converted using 3-bromophenyl methyl sulphone and, after workup and purification, 23 mg (37%) of the title compound were isolated as a colourless foam.

EXAMPLE 52

4-methoxyphenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

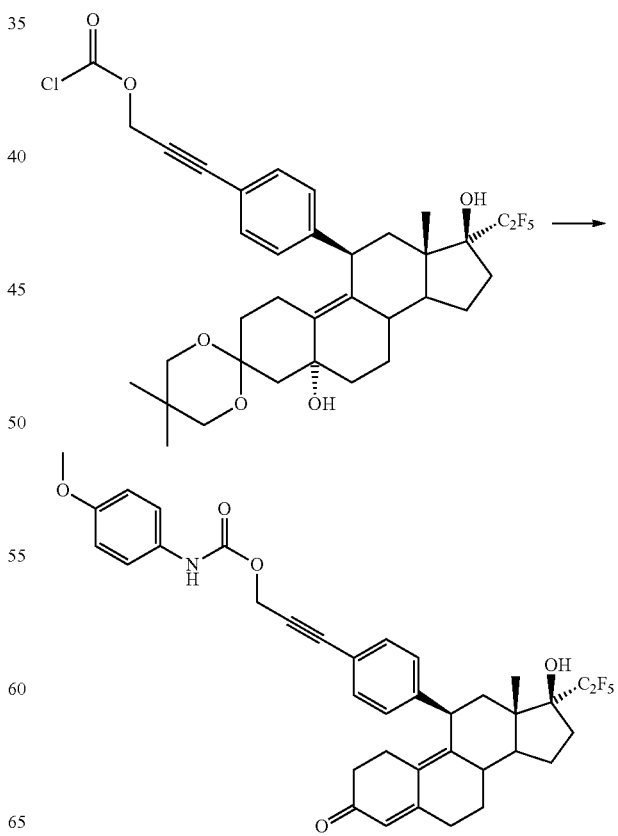

In analogy to Example 50, 52 mg (79 μmol) of the compound prepared according to Example 50a were converted using 3-anisidine and, after workup and purification, 13 mg (25%) of the title compound were isolated as a colourless foam.

$^1$H NMR (CDCl$_3$):=0.56 (3H), 1.38-1.56 (2H), 1.72-1.86 (3H), 2.07 (1H), 2.17 (1H), 2.19-2.64 (9H), 2.71 (1H), 3.78 (3H), 4.43 (1H), 4.99 (2H), 5.79 (1H), 6.63 (1H), 6.85 (2H), 7.13 (2H), 7.29 (2H), 7.38 (2H) ppm.

EXAMPLE 53

4-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxycarbonylamino}benzoic acid ethyl ester

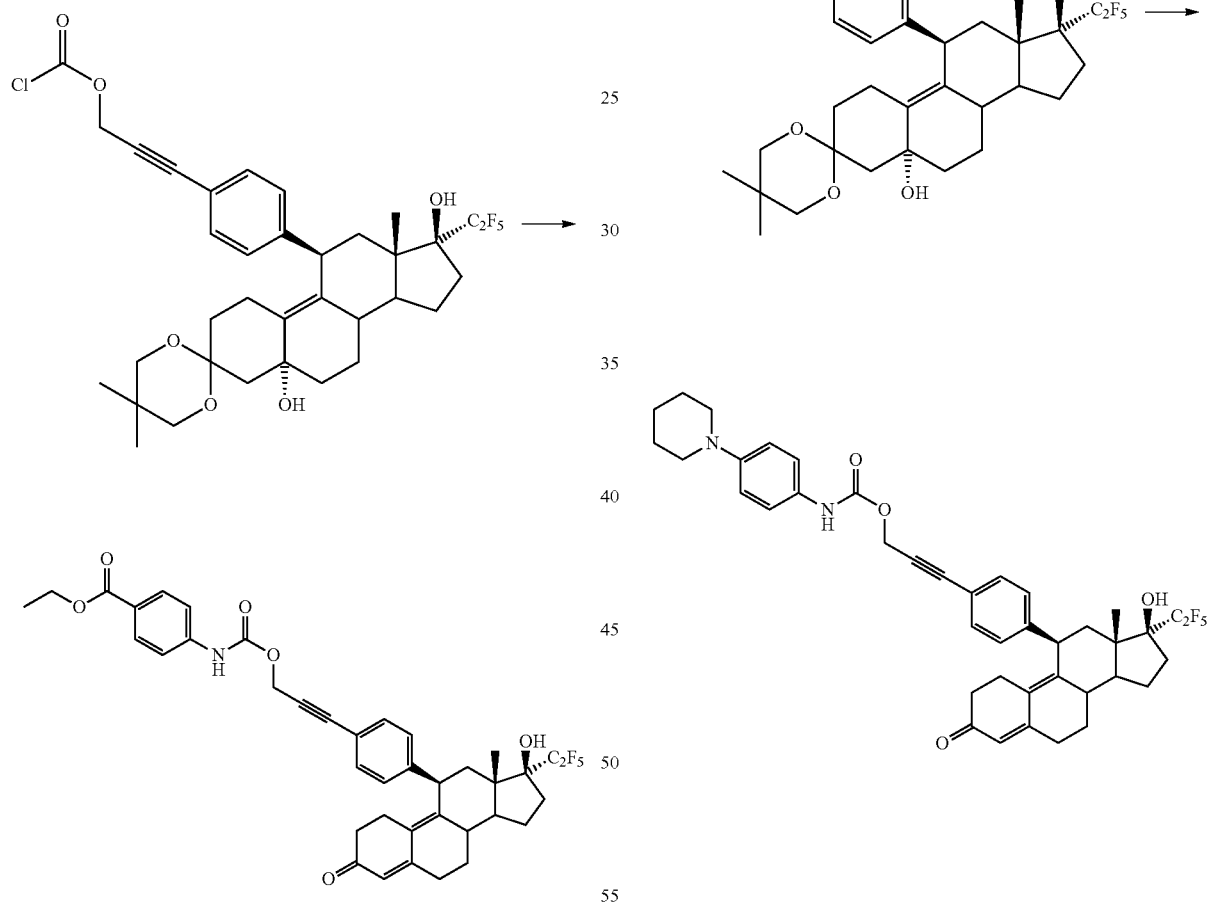

In analogy to Example 50, 46.7 mg (80 μmol) of the compound prepared according to Example 50a were converted using ethyl 4-aminobenzoate and, after workup and purification, 7.7 mg (14%) of the title compound were isolated as a colourless foam.

$^1$H NMR (CDCl$_3$):=0.56 (3H), 1.38 (3H), 1.39-1.55 (2H), 1.72-1.86 (3H), 2.06 (1H), 2.18-2.64 (10H), 2.72 (1H), 4.35 (2H), 4.43 (1H), 5.02 (2H), 5.79 (1H), 7.03 (1H), 7.13 (2H), 7.37 (2H), 7.47 (2H), 8.00 (2H) ppm.

EXAMPLE 54

(4-piperidin-1-ylphenyl)carbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester In analogy to Example 50, 46.7 mg (80 μmol) of the compound prepared according to Example 50a were converted using 4-piperidin-1-ylphenylamine and, after workup and purification, 10.1 mg (17%) of the title compound were isolated as a colourless foam.

$^1$H NMR (CDCl$_3$):=0.56 (3H), 1.38-1.87 (11H), 2.06 (1H), 2.17 (1H), 2.20-2.64 (9H), 2.72 (1H), 3.08 (4H), 4.43 (1H), 4.98 (2H). 5.79 (1H), 6.58 (1H), 6.90 (2H), 7.13 (2H), 7.25 (2H), 7.38 (2H) ppm.

EXAMPLE 55

4-chlorophenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

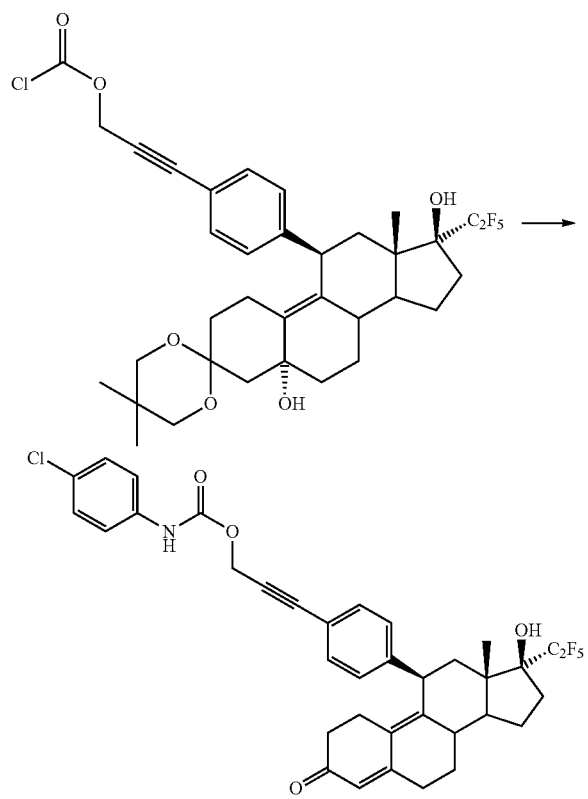

In analogy to Example 50, 46.7 mg (80 µmol) of the compound prepared according to Example 50a were converted using 4-chloroaniline and, after workup and purification, 7.4 mg (14%) of the title compound were isolated as a colourless foam.

$^1$H NMR (CDCl$_3$):=0.56 (3H), 1.38-1.55 (2H), 1.72-1.86 (3H), 2.06 (1H), 2.09 (1H), 2.18-2.64 (9H), 2.71 (1H), 4.43 (1H), 5.00 (2H), 5.79 (1H), 6.76 (1H), 7.13 (2H), 7.27 (2H), 7.35 (2H), 7.38 (2H) ppm.

EXAMPLE 56

(8S,11R,13S,14S,17S)-17-hydroxy-11-[4-(4-methanesulphonylphenylethynyl)phenyl]-13-methyl-17-pentafluoroethyl-1,2,6,7,8,11,12,13,14,15,16,17-dodecahydrocyclopenta[a]phenanthren-3-one

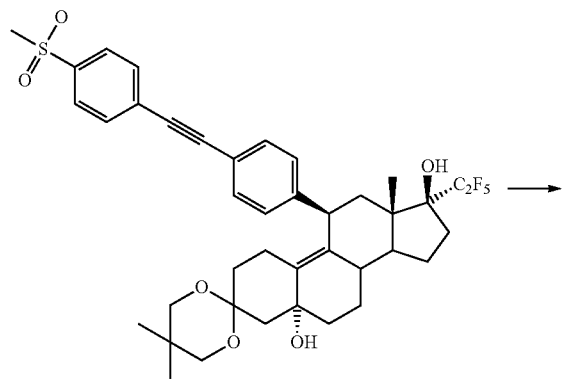

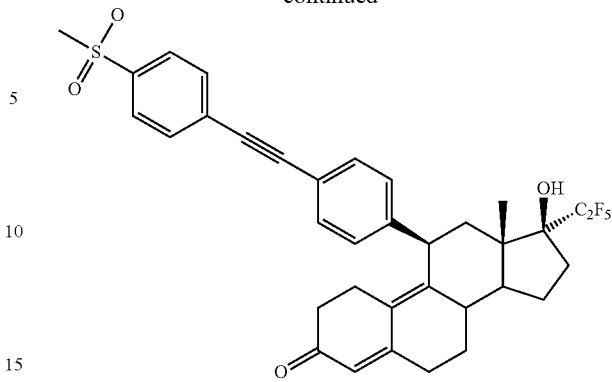

In analogy to Example 1, 11.4 mg (15 µmol) of the compound prepared according to Example 56a were converted and, after workup and purification, 5.4 mg (55%) of the title compound were isolated as a colourless foam.

$^1$H NMR (CDCl$_3$):=0.60 (3H), 1.42-1.56 (2H), 1.75-1.88 (3H), 2.08 (2H), 2.23-2.67 (9H), 2.74 (1H), 3.07 (3H), 4.47 (1H), 5.80 (1H), 7.21 (2H), 7.48 (2H), 7.69 (2H), 7.92 (2H) ppm.

EXAMPLE 56a (5R,8S,11R,13S,14S,17S)-11-[4-(4-methanesulphonylphenylethynyl)phenyl]-5',5',13-trimethyl-17-pentafluoroethyl-1,2,3,4,6,7,8,11,12,13,14,15,16,17-tetradecahydro-spiro[cyclopenta[a]phenanthrene-3,2'-[1,3]dioxane]-5,17-diol

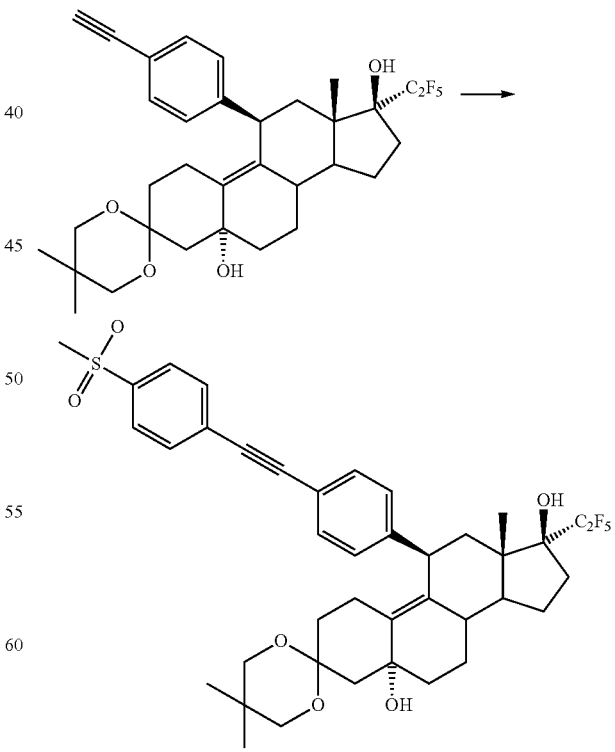

In analogy to Example 17b, 50 mg (84 µmol) of the compound prepared according to Example 15b were converted using 4-bromophenyl methyl sulphone and, after workup and purification, 11.4 mg (18%) of the title compound were isolated as a colourless foam.

EXAMPLE 57

3-pyridylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

EXAMPLE 58 tert-butylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

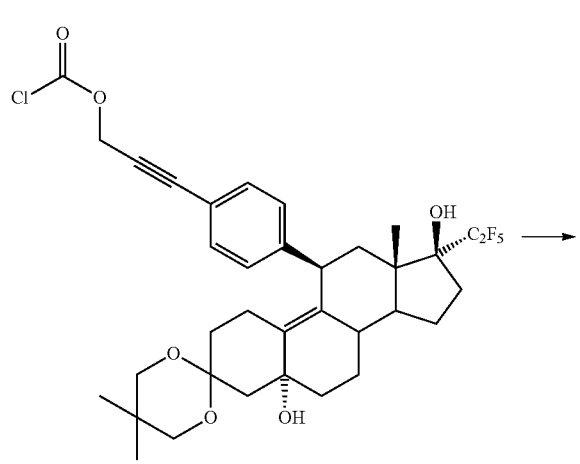

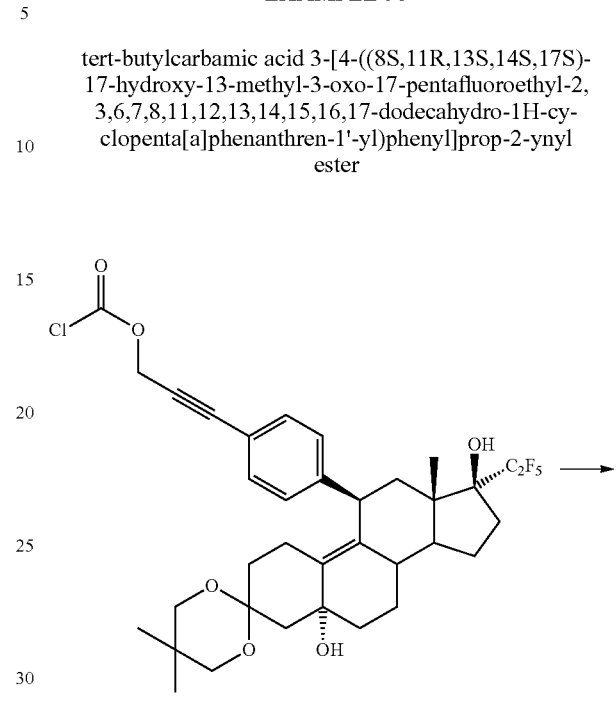

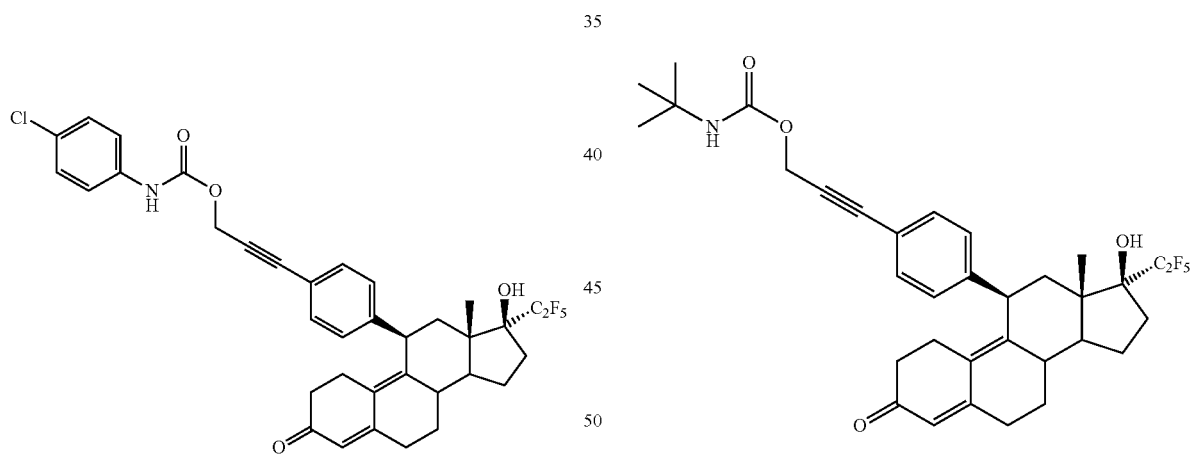

In analogy to Example 50, 93.3 mg (0.16 mmol) of the compound prepared according to Example 50a were converted using pyridin-3-ylamine and, after workup and purification, 16.3 mg (16%) of the title compound were isolated as a colourless foam.

$^1$H NMR (CDCl$_3$):=0.57 (3H), 1.38-1.55 (2H), 1.72-1.87 (3H), 2.06 (1H), 2.17-2.63 (9H), 2.70 (1H), 3.10 (1H), 4.41 (1H), 5.02 (2H), 5.78 (1H), 7.10 (2H), 7.20 (1H), 7.28 (1H), 7.35 (2H), 8.02 (1H), 8.31 (1H), 8.49 (1H) ppm.

In analogy to Example 50, 52 mg (79 μmol) of the compound prepared according to Example 50a were converted using tert-butylamine and, after workup and purification, 16 mg (33%) of the title compound were isolated as a colourless foam.

$^1$H NMR (CDCl$_3$):=0.57 (3H), 1.33 (9H), 1.40-1.54 (2H), 1.73-1.85 (3H), 2.07 (1H), 2.17 (1H), 2.20-2.64 (9H), 2.72 (1H), 4.43 (1H), 4.77 (1H), 4.85 (2H), 5.79 (1H), 7.13 (2H), 7.37 (2H) ppm.

EXAMPLE 59

4-tert-butylphenylcarbamic acid 3-[4-((8S,11R,13S, 14S,17S)-17-hydroxy-13-methyl-3-oxo-17-pentafluoroethyl-2,3,6,7,8,11,12,13,14,15,16,17-dodecahydro-1H-cyclopenta[a]phenanthren-1'-yl)phenyl]prop-2-ynyl ester

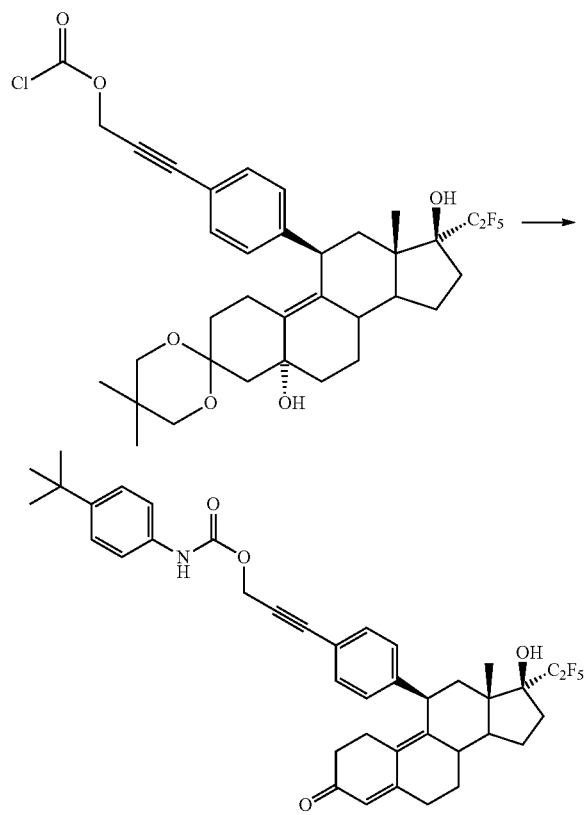

In analogy to Example 50, 46.7 mg (80 µmol) of the compound prepared according to Example 50a were converted using 4-tert-butylaniline and, after workup and purification, 11 mg (19%) of the title compound were isolated as a colourless foam.

$^{1}$H NMR (CDCl$_3$):=0.57 (3H), 1.30 (9H), 1.40-1.54 (2H), 1.73-1.85 (3H), 2.02-2.12 (2H), 2.20-2.63 (9H), 2.72 (1H), 4.44 (1H), 5.00 (2H), 5.79 (1H), 6.67 (1H), 7.13 (2H), 7.30 (2H), 7.34 (2H), 7.38 (2H) ppm.

EXAMPLE 60

Determination of Progesterone Receptor-Antagonistic Action in Stable Transfectants of Human Neuroblastoma Cells (SK-N-MC Cells) with the Human Progesterone a or Progesterone B Receptor and an MN-LUC Reporter Construct SK-N-MC cells (human neuroblastoma cells) which have been stably transfected with plasmids expressing the human progesterone receptor B (pRChPR-B-neo) or the human progesterone receptor A (pRChPR-A-neo) and a reporter construct (pMMTV-LUC) were incubated for 24 hours either in the absence (negative control) or in the presence of ascending amounts of the particular test compound (0.01 nmol/l, 0.1 nmol/l, 1 nmol/l, 10 nmol/l, 100 nmol/l and 1 pmol/l), in order to determine the agonistic efficacy. As a positive control of the reporter gene induction, the cells were treated with the synthetic gestagen promegestone (0.01 nmol/l, 0.1 nmol/l, 1 nmol/l, 10 nmol/l, 100 nmol/l and 1 pmol/l). To determine the antagonistic activity, the cells were treated with 0.1 nmol/l promegestone and additionally with ascending amounts of the particular test compound (0.01 nmol/l, 0.1 nmol/l, 1 nmol/l, 10 nmol/l, 100 nmol/l and 1 pmol/l). The activity of the reporter gene LUC (LUC=luciferase) was determined in the cell lysates and measured as RLU (relative light units). All measurements are reported as % efficacy and as EC$_{50}$ and IC$_{50}$ concentrations.

a) Agonistic activity: None of the compounds mentioned exhibits agonistic activity.

b) Antagonistic activity: All compounds mentioned exhibit 100% antagonistic activity.

The antagonistic potency of the compounds is summarized in Table 1. Preference is given in accordance with the invention to compounds whose PR-A or PR-B value is ≤0.2 nM.

TABLE 1

| | IC$_{50}$ [nM] | |
|---|---|---|
| Ex. | PR-A | PR-B |
| 1 | 0.097 | 0.11 |
| 2 | 32 | 16 |
| 3 | 1.8 | 1.2 |
| 4 | 0.2 | 0.1 |
| 5 | 0.72 | 0.76 |
| 6 | 13 | 12 |
| 7 | 0.8 | 0.9 |
| 8 | 0.32 | 0.41 |
| 9 | 8.1 | 10 |
| 10 | 9.0 | 10 |
| 11 | 0.32 | 1.0 |
| 12 | 1 | 2 |
| 13A | 0.1 | 0.2 |
| 13B | nd | nd |
| 14 | 0.1 | 0.1 |
| 15 | 0.7 | 1.0 |
| 16 | 0.1 | 0.05 |
| 17 | 0.2 | 0.2 |
| 18 | 8 | 5 |
| 19 | 3.3 | 4.3 |
| 20 | 2.3 | 7.0 |
| 21 | 0.36 | 1.0 |
| 22 | 0.014 | 0.014 |
| 23 | 0.2 | 0.3 |
| 24A | 0.1 | 0.1 |
| 24B | 0.1 | 0.1 |
| 25A | 0.01 | 0.08 |
| 25B | 0.09 | 0.09 |
| 26 | 0.08 | 0.08 |
| 27 | 0.97 | 2.0 |
| 28 | 0.04 | 0.08 |
| 29 | 0.1 | 0.1 |
| 30 | 0.1 | 0.4 |
| 31 | 0.08 | 0.1 |
| 32 | 0.2 | 0.1 |
| 33 | 0.9 | 0.8 |
| 34 | 0.1 | 0.1 |
| 35 | 0.4 | 0.4 |
| 36 | 0.1 | 0.2 |
| 37 | 0.1 | 0.4 |
| 38 | 0.2 | 0.3 |
| 39 | 0.1 | 0.1 |
| 40 | 0.1 | 0.3 |
| 41 | 0.1 | 0.1 |
| 42 | 0.7 | 0.8 |
| 43 | 0.8 | 0.9 |
| 44 | 0.01 | 0.01 |
| 45 | 0.01 | 0.01 |
| 46 | 0.01 | 0.01 |
| 47 | 0.01 | 0.01 |

TABLE 1-continued

| Ex. | IC$_{50}$ [nM] PR-A | IC$_{50}$ [nM] PR-B |
|---|---|---|
| 48 | 0.09 | 0.08 |
| 49 | 0.01 | 0.07 |
| 50 | 0.01 | 0.03 |
| 51 | 0.08 | 0.1 |
| 52 | 0.01 | 0.07 |
| 53 | 0.16 | 0.19 |
| 54 | 0.10 | 0.09 |
| 55 | 0.26 | 0.2 |
| 56 | 0.01 | 0.08 |
| 57 | 0.01 | 0.08 |
| 58 | 0.09 | 0.01 |
| 59 | 0.7 | 1.2 |
| Ref. 1* | 0.4 | 0.3 | nd = not determined

*Ref. 1 Table 1: The comparative compound (reference substance) is the compound, described in Example 10 of WO 1998/34947, (8S,11R,13S,14S,17S)-17-hydroxy-11-[4-(hydroxymethyl)phenyl]-13-methyl-17-pentafluoroethyl-1,2,6,7,8,11,12,13,14,15,16,17-dodecahydrocyclopenta[a]phenanthren-3-one.

EXAMPLE 61

Determination of Metabolic Stability in Human and Rat Liver Microsomes

Isolated Human Liver Microsomes (HLM) were Used to Assess the Metabolic Stability of compounds of general formula I.

The incubations were conducted with 2.4 ml of HLM solution (protein content 0.5 mg/ml), 30 μl of the test compound (final concentration 1 μM) and 0.6 ml of the cofactor mixture (=NADPH-generating system composed of 3 IU glucose-6-phosphate dehydrogenase, 14.6 mg glucose-6-phosphate, 1.2 mg NADP) at 37° C. in 100 mM phosphate buffer at pH 7.4. Samples were taken at 6 time points (2-60 min) and precipitated with an equal volume of methanol, and the recovery of the test substances used in the supernatant was determined by LC-MS/MS analysis. The half-life of substance degradation determined therefrom was used to calculate what is called the intrinsic clearance of the substance in the liver microsome preparation. With the aid of this, together with various physiological parameters (human hepatic blood flow: 1.3 l*kg/h; specific liver weight (per kg of body weight): 21 g/kg; microsomal protein content: 40 mg/g of liver), in accordance with the well-stirred model, (metabolic) in vivo clearance in relation to phase I reactions was predicted. In addition, under the assumptions that (i) absorption of the test substance is 100%, and (ii) the first pass is completely reflected by liver microsome metabolism, a maximum oral bioavailability (Fmax) was calculated.

The compounds tested have surprisingly high metabolic stability (small based on the clearance rate predicted on the basis of the in vitro data) and good predicted maximum oral bioavailability $F_{max}$ (Table 2).

In addition, some compounds have an unusually good solubility, for this active ingredient class, in aqueous medium under physiological conditions (Table 2).

TABLE 2

| Ex. | Predicted clearance [l/h/kg] Human | Predicted clearance [l/h/kg] Rat | Predicted $F_{max}$ [%] (maximum oral bioavailability) Human | Predicted $F_{max}$ [%] (maximum oral bioavailability) Rat | Solubility at pH 7.4 [mg/l] |
|---|---|---|---|---|---|
| Ref. 1* | 0.7 | 0.8 | 42 | 80 | 17 |
| 1 | 0.32 | 0.9 | 76 | 78 | 13 |
| 2 | 0.00 | 0.0 | 100 | 100 | 178 |
| 4 | 0.09 | 0.2 | 93 | 96 | 8 |
| 5 | 0.17 | 0.9 | 87 | 78 | 8 |
| 11 | 0.49 | 0.2 | 63 | 94 | 30 |
| 13A | 0.31 | 0.0 | 77 | 100 | 148 |
| 16 | 0.33 | 0.0 | 75 | 100 | 204 |
| 17 | 0.08 | 0.0 | 94 | 100 | 204 |
| 24A | 0.88 | 2.2 | 34 | 49 | 5 |
| 25A | 0.70 | 0.9 | 47 | 79 | 5 |
| 31 | 1.13 | 0.9 | 15 | 78 | 10 |
| 34 | 1.21 | 1.4 | 9 | 68 | 7 |
| 36 | 0.60 | 0.5 | 55 | 88 | 4 |

*Ref. 1 Table 2: The comparative compound (reference substance) is the compound, described in Example 10 of WO 1998/34947, (8S,11R,13S,14S,17S)-17-hydroxy-11-[4-(hydroxymethyl)phenyl]-13-methyl-17-pentafluoroethyl-1,2,6,7,8,11,12,13,14,15,16,17-dodecahydrocyclopenta[a]phenanthren-3-one.

The comparative compound has good predicted maximum bioavailability in rats, but not in humans.

Particular preference is therefore given to those compounds which each have a predicted maximum oral bioavailability greater than 50% in different species (rats, humans).

Very particular preference is given to those compounds which each have a predicted maximum oral bioavailability greater than 70% in different species (rats, humans). Examples include compounds of Examples 1, 2, 4, 5, 13A, 16 and 17.

Particular preference is likewise given to compounds with improved solubility. Examples include compounds of Examples 2, 11, 13A, 16 and 17.

EXAMPLE 62

Determination of Clearance and of Half-Life after Intravenous Administration in Rats The determination of the in vivo clearance and half-life of test substances was conducted in female rats with a body weight of approx. 200-250 g. For this purpose, the test substances (in a cassette test up to 3 different substances per animal) were administered intravenously (i.v.) into the tail vein in dissolved form at a dose of 0.3-0.5 mg/kg as a bolus in a volume of 2 ml/kg, using compatible solubilizers such as PEG400 and/or ethanol in a compatible amount. A polyurethane catheter in the jugular vein was used to take approx. 0.2 ml blood samples at the time points of 2 min, 8 min, 15 min, 30 min, 45 min, 1 h, 2 h, 4 h, 6 h, 8 h, 24 h. The blood samples were stored without shaking in lithium heparin tubes (Monovettes® from Sarstedt) and centrifuged at 3000 rpm for 15 min. An aliquot of 100 μl was taken from the supernatant (plasma) and precipitated by adding 400 μl of cold methanol. The precipitated samples were frozen at −20° C. overnight, then centrifuged again at 3000 rpm for 15 min, before 150 μl of the clear supernatant were removed to determine the concentration. The analysis was effected by means of an Agilent 1200 HPLC system with connected LC-MS/MS detection.

Calculation of the PK Parameters (Via Nonlinear Regression by PK Calculation Software):

CLplasma: total plasma clearance of the test substance (in l*kg/h),
where CLplasma=dose/AUCinf;
AUCinf: extrapolated area under the plasma concentration-time curve (in µg*h/l);
CLblood: total blood clearance of the test substance (in l*kg/h), where (CLblood=CLplasma*Cp/Cb);
Cb/Cp: ratio of the blood to plasma concentration distribution of the test substance;
T½: terminal half-life of the test substance (in h).

TABLE 3

| Example | CL$_{blood}$ [l/h/kg] | t$_{1/2}$ [h] |
|---|---|---|
| 1 | 0.9 ± 0.08 | 12.3 ± 0.3 |
| 4 | 3.3 ± 1.3 | 1.1 ± 0.7 |
| 16 | 2.1 ± 0.5 | 2.2 ± 0.4 |
| 17 | 0.7 ± 0.1 | 4.0 ± 0.8 |

Particular preference is given to compounds which have a terminal half-life of at least 1 hour in rats. Examples include compounds of Examples 1, 4, 16 and 17.

Very particular preference is given to compounds which have a terminal half-life of more than 8 hours and at the same time a blood clearance of less than 1.3 l/h/kg in rats. One example is the compound from Example 1.

EXAMPLE 63

Abortion Test on Female Rats

The action of progesterone and of the progesterone receptor is a fundamental precondition for successful pregnancy or gestation in mammals. The progesterone-antagonistic action of the inventive compounds was tested on pregnant rats (6 rats per group) on days 5 to 7 post coitum under conventional housing and feeding conditions.

After successful mating, the pregnant animals (presence of sperm in the vaginal smear on day 1 of pregnancy=d1 p.c.) were randomized and divided into the treatment group and the control group. The animals then each received subcutaneously or orally 0.15; 0.5; 1.5 or 5 mg/kg of the test compound or 1.0 ml/kg of vehicle (benzyl benzoate/castor oil: 1+4 [v/v]) daily from day 5 to day 7 (d5–d7 p.c.).

Autopsy was conducted on day 9 (d9 p.c.). As a characteristic of progesterone receptor-antagonistic action, the uterus was examined for the presence of nidation sites. Complete absence, or else the presence of pathological, haemorrhagic or otherwise abnormal nidation sites, on day 9 (d9 p.c.) was considered as abortion. The results of the tests are shown in Table 4.

TABLE 4

| Test compound | Daily dose [mg/kg] p.o. | Abortion rate [%] |
|---|---|---|
| Vehicle | | 0 |
| Example 1 | 0.5 | 100 |
| | 1.5 | 100 |
| | 5.0 | 100 |
| Example 16 | 0.5 | 0 |
| | 1.5 | 16.7 |
| | 5.0 | 100 |

The invention claimed is:

1. 17-Hydroxy-17-pentafluoroethylestra-4,9(10)-diene 11-ethynylphenyl derivatives of the formula I

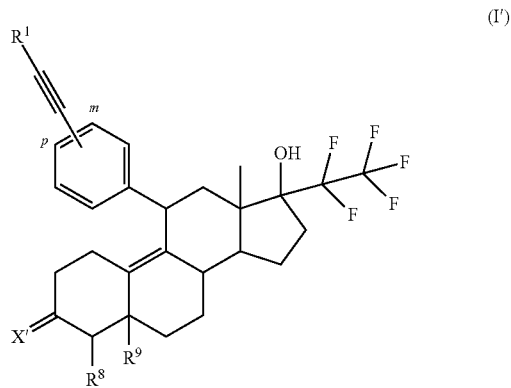

(I')

in which

R$^1$ is joined to the phenyl ring in the m or p position via a C—C triple bond and is a (CH$_1$=CH)$_n$—R$^2$, —(CH$_2$)$_q$—R$^3$ or —CH=NOR$^4$ radical, R$^2$ is hydrogen or an aryl, C$_1$-C$_{10}$-alkyl, —CO$_2$R$^6$ or —CN group, R$^3$ is hydrogen, NH$_2$, N$_3$ or an —NHCONHR$^4$, —OCONHR$^4$, or —OR$^5$ group, R is hydrogen, C$_1$-C$_{10}$-alkyl, C$_2$-C$_{10}$— alkenyl, aryl, C$_7$-C$_{20}$-aralkyl, (CH$_2$)$_s$—R$^6$, CH$_2$—CO—OR$^6$, or

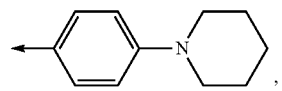

in which

R$^5$ is hydrogen, C$_7$-C$_{20}$-aralkyl, CH$_2$CO$_2$R$^6$, CH$_2$CN, CH$_2$CH$_2$OH,

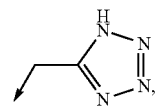

or

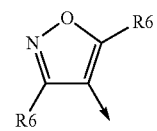

n is 0 to 2,
q is 1 or 2,
s is 1 or 2,
R$^6$ is hydrogen, C$_1$-C$_{10}$-alkyl, aryl, or C$_7$-C$_{20}$-aralkyl, and
X is oxygen, NOR$^6$ or an NNHSO$_2$R$^6$ group where R$^6$ is as defined above, and the salts thereof.

2. Compound according to claim 1 in which X is oxygen.
3. Compound according to claim 1 in which the

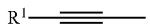

group is joined to the phenyl ring in the para position.

4. Compound according to claim 1, in which $R^1$ is a —(CH=CH)$_n$—$R^2$ or a —(CH$^2$)$_q$—$R^3$ group, where n, q, $R^2$ and $R^3$ are each as defined in claim 1.

5. Compound according to claim 1, in which $R^2$ is a COOH group and $R^3$ is a —OR$^5$ group where $R^5$ is defined as CH$_2$CO$_2$H or CH$_2$CH$_2$OH.

6. Compound according to claim 1, in which the $R^1$ group bears a terminal carboxylic acid group or an alcohol group.

7. Compounds according to claim 1, specifically
- (8S,11R,13S,14S,17S)-17-hydroxy-11-[4-(3-hydroxyprop-1-yn-1-yl)phenyl]-13-methyl-17-pentafluoroethyl-1,2,6,7,8,11,12,13,14,15,16,17-dodecahydrocyclopenta[a]phenanthren-3-one;
- (E)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]pent-2-en-4-ynenitrile;
- (Z)-5-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]pent-2-en-4-ynenitrile;
- (8S,11R,13S,14S,17S)-17-hydroxy-11-{4-[3-(2-hydroxyethoxy)prop-1-yn-1-yl]phenyl}-13-methyl-17-pentafluoroethyl-1,2,6,7,8,11,12,13,14,15,16,17-dodecahydrocyclopenta[a]phenanthren-3-one;
- 3-{(E)-4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]but-1-en-3-ynyl}benzoic acid;
- {3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxy}acetonitrile;
- 4-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenylethynyl]benzoic acid methyl ester;
- (8S,11R,13S,14S,17S)-11-(4-ethynylphenyl)-17-hydroxy-13-methyl-17-pentafluoroethyl-1,2,6,7,8,11,12,13,14,15,16,17-dodecahydrocyclopenta[a]phenanthren-3-one;
- (8S,11R,13S,14S,17S)-11-[4-(3-azidoprop-1-yn-1-yl)phenyl]-17-hydroxy-13-methyl-17-pentafluoroethyl-1,2,6,7,8,11,12,13,14,15,16,17-dodecahydrocyclopenta[a]phenanthren-3-one;
- (E)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-benzyl oxime and (Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-benzyl oxime;
- (E)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-ethyl oxime and (Z)-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-ethyl oxime;
- [4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]propynal O-isobutyl oxime;
- 1-(3,5-dimethylisoxazol-4-yl)-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}urea;
- 1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-isopropylurea;
- 3-(3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}ureido)propionic acid ethyl ester;
- 1-ethyl-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}urea;
- 1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-methoxyphenyl)urea;
- 1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-phenylurea;
- 1-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}-3-(4-fluorophenyl)urea;
- 1-benzyl-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}urea;
- 1-allyl-3-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl}urea;
- allylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester;
- ethylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester;
- phenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester;
- 4-methylphenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester;

4-fluorophenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester;

isopropylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester;

benzylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester;

(8S,11R,13S,14S,17S)-17-hydroxy-11-[4-(3-methanesulphonyl-phenylethynyl)phenyl]-13-methyl-17-pentafluoroethyl-1,2,6,7,8,11,12,13,14,15,16,17-dodecahydrocyclopenta[a]phenanthren-3-one;

4-methoxyphenylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester;

4-{3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyloxycarbonylamino}benzoic acid ethyl ester;

(4-piperidin-1-ylphenyl)carbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester;

(8S,11R,13S,14S,17S)-17-hydroxy-11-[4-(4-methanesulphonylphenylethynyl)phenyl]-13-methyl-17-pentafluoroethyl-1,2,6,7,8,11,12,13,14,15,16,17-dodecahydrocyclopenta[a]phenanthren-3-one;

3-pyridylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester; or tert-butylcarbamic acid 3-[4-((8S,11R,13S,14S,17S)-17-hydroxy-13-methyl-3-oxo-17-pentafluoroethyl-2,3,6,7,8,11,12,13,14,15,16,17-dodecahydro-1H-cyclopenta[a]phenanthren-11-yl)phenyl]prop-2-ynyl ester.

8. Pharmaceutical formulation comprising at least one compound according to claim 1 and pharmaceutically suitable carrier.

9. Method for the treatment of fibroids of the uterus, myomas, uterine leiomyomas, endometriosis, heavy menstrual bleeds, meningiomas, or breast cancer comprising the step of administering a compound according to claim 1 to a patient in need thereof.

10. Method for fertility control or emergency contraception comprising the step of administering a compound according to claim 1 to a patient in need thereof.

* * * * *